United States Patent
Hausen et al.

(10) Patent No.: US 6,869,437 B1
(45) Date of Patent: Mar. 22, 2005

(54) METHOD AND SYSTEM FOR PERFORMING CLOSED-CHEST BYPASS

(75) Inventors: Bernard A. Hausen, Menlo Park, CA (US); Jaime S. Vargas, Menlo Park, CA (US); Stephen A. Yencho, Menlo Park, CA (US); James T. Nielsen, San Francisco, CA (US); Theodore M. Bender, San Francisco, CA (US); Brendan M. Donohoe, San Francisco, CA (US); Philip E. Oyer, Woodside, CA (US); Scott O. Chamness, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 69 days.

(21) Appl. No.: 09/993,438

(22) Filed: Nov. 13, 2001

Related U.S. Application Data
(60) Provisional application No. 60/247,029, filed on Nov. 13, 2000.

(51) Int. Cl.[7] ............................................. A61B 17/08
(52) U.S. Cl. ...................................... 606/153; 600/231
(58) Field of Search .............................. 600/231, 153, 600/128; 604/508; 128/808

(56) References Cited

U.S. PATENT DOCUMENTS

| | | | |
|---|---|---|---|
| 5,104,393 A | * 4/1992 | Isner et al. ................... 606/15 |
| 5,203,776 A | * 4/1993 | Durfee ........................ 604/264 |
| 5,250,038 A | * 10/1993 | Melker et al. ............... 604/264 |
| 5,275,622 A |  1/1994 | Lazarus et al. ................ 623/1 |
| 5,433,700 A | * 7/1995 | Peters ........................ 604/6.14 |
| 5,452,733 A | * 9/1995 | Sterman et al. ............. 128/898 |
| 5,695,504 A |  12/1997 | Gifford, III et al. ......... 606/153 |
| 5,702,412 A | * 12/1997 | Popov et al. ............... 606/159 |
| 5,735,290 A | * 4/1998 | Sterman et al. ............. 128/898 |
| 5,888,247 A |  3/1999 | Benetti |
| 6,026,814 A |  2/2000 | LaFontaine et al. |
| 6,036,641 A | * 3/2000 | Taylor et al. ................ 600/231 |
| 6,066,144 A | * 5/2000 | Wolf et al. .................. 606/139 |
| 6,068,637 A |  5/2000 | Popov et al. |
| 6,083,153 A |  7/2000 | Rullo et al. ................. 600/217 |
| 6,110,187 A | * 8/2000 | Donlon ....................... 606/151 |
| 6,167,889 B1 |  1/2001 | Benetti |
| 6,199,556 B1 |  3/2001 | Benetti et al. |
| 6,248,119 B1 |  6/2001 | Solem |
| 6,253,769 B1 |  7/2001 | LaFontaine et al. |
| 6,254,535 B1 |  7/2001 | Furnish et al. |
| 6,290,644 B1 |  9/2001 | Green, II et al. |

(List continued on next page.)

FOREIGN PATENT DOCUMENTS

| | | |
|---|---|---|
| WO | 99/21491 | 5/1999 |
| WO | 2004/064646 A1 | 1/2004 |
| WO | 2004/064647 A1 | 1/2004 |

OTHER PUBLICATIONS

Korkola, S et al., A Novel Automated Interrupted Suturing Device for Coronary Artery Bypass Grafting, Abstract, The Heart Surgery Forum, 2000.

(List continued on next page.)

*Primary Examiner*—Julian W. Woo
(74) *Attorney, Agent, or Firm*—Brian A. Schar

(57) ABSTRACT

A coronary artery bypass graft procedure is performed through one or more openings made in the patient to create a point of entry to the thoracic cavity. A vein measurement device measures the distance between the proximal and distal anastomotic sites for each graft. A proximal anastomosis tool splits to release a graft vessel after deploying an anastomosis device at the proximal anastomosis site. The tool may be articulated. An integrated stabilizer stabilizes one or more tools relative to the surface of the beating heart at a distal anastomotic site. A distal anastomotic tool may be provided as part of the integrated stabilizer, and connects one end of the graft vessel to a target vessel. An epicardial dissector may be provided as part of the integrated stabilizer, and dissects the epicardium from the target vessel at a distal anastomotic site, as needed.

26 Claims, 71 Drawing Sheets

U.S. PATENT DOCUMENTS

| | | | | |
|---|---|---|---|---|
| 6,296,630 | B1 | * 10/2001 | Altman et al. | 604/508 |
| 6,309,349 | B1 | 10/2001 | Bertolero et al. | |
| 6,325,067 | B1 | 12/2001 | Sterman et al. | 128/898 |
| 6,331,158 | B1 | 12/2001 | Hu et al. | |
| 6,354,994 | B1 | 3/2002 | Rullo et al. | 600/217 |
| 6,475,222 | B1 | * 11/2002 | Berg et al. | 606/108 |
| 6,478,728 | B1 | 11/2002 | Wright | |
| 6,626,920 | B2 | 9/2003 | Whayne | |
| 6,786,898 | B2 | 9/2004 | Guenst | |
| 2002/0082470 | A1 | 6/2002 | Devries et al. | |
| 2002/0095067 | A1 | 7/2002 | Guenst et al. | |
| 2003/0010346 | A1 | * 1/2003 | Paolitto et al. | 128/898 |
| 2003/0078471 | A1 | 4/2003 | Foley et al. | |
| 2003/0167064 | A1 | 9/2003 | Whayne | |

OTHER PUBLICATIONS

Morota, T et al., Proximal One–Shot Anastomotic Device: Short–Term Results, Abstract, The Heart Surgery Forum, 2000.

Matheny, Robert, A Perspective on MIDCAB, Editorial, Heart Surgery Forum, 1999.

Mandke, NV et al., Three Year Follow Up of Minimally Invasive Coronary Artery Surgery, Abstract, Heart Surgery Forum, 2000.

Off–Pump Coronary Artery Bypass Surgery: Wave of the Future, Article, www.ccf.org, 1999.

Solem, Jan et al., European Journal of Cardio–Thoracic Surgery, Abstract, European Journal of Cardio–Thoracic Surgery, Mar. 1, 2000.

Boyd, W et al., Closed–Chest Coronary Artery Bypass Grafting on the Beating Heart with the Use of a Computer–Enhanced Surgical Robotic System, The Journal of Thoracic and Cardiovascular Surgery, 807–809, Oct. 2000.

Kappert, Utz et al., Closed–Chest Coronary Artery Surgery on the Beating Heart with the Use of a Robotic System, The Journal of Thoracic and Cardiovascular Surgery, 809–811, Oct. 2000.

Reichenspurner, Hermann et al., Robotically Assisted Endoscopic Coronary Artery Bypass Procedures Without Cardiopulmonary Bypass, The Journal of Thoracic and Cardiovascular Surgery, 1–4, 11/99.

Falk, Volkmar et al., Total Endoscopic Computer Enhanced Coronary Artery Bypass Grafting, European Journal of Cardio–Thoracic Surgery, 1–15, 2000.

Boyd, W et al., RAVECAB: Improving Outcome in Off-Pump Minimal Access Surgery with Robotic Assistance and Video Enhancement, Canadian Journal of Surgery, 45–50, 2/01.

Chiu, Adeline et al., 3–D Image Guidance for Minimally Invasive Robotic Coronary Artery Bypass, The Heart Surgery Forum, 224–231, Jun. 8, 2000.

Kiaii, Bob et al., Robot–Assisted Computer Enhanced Closed–Chest Coronary Surgery, The Heart Surgery Forum, 194–197, May 28, 2000.

Kappert, Utz et al., Wrist–Enhanced Instrumentation: Moving Toward Totally Endoscopic Coronary Artery Bypass Grafting, The Annals of Thoracic Surgery, 1–8, Jan. 27, 2000.

Kappert, Utz et al., Closed Chest Bilateral Mammary Artery Grafting in Double–Vessel Coronary Artery Disease, The Annals of Thoracic Surgery, 1–4, 2000.

Cichon, Romuald et al., Robotic–Enhanced Arterial Revascularization for Multivessel Coronary Artery Disease, The Annals of Thoracic Surgery, 1060–1062, Jan. 27, 2000.

Kappert, Utz et al., Robotic–Enhanced Dredsden Technique for Minimally Invasive Bilateral Internal Mammary Artery Grafting, The Heart Surgery Forum, 319–321, Jun. 8, 2000.

Tabaie, Harold et al., Endoscopic Coronary Artery Bypass Graft Procedure with Robotic Assistance, The Heart Surgery Forum, 310–316, Sep. 7, 1999.

Damiano, Ralph et al., Initial US Clinical Trial of Robotically Assisted Endoscopic Coronary Artery Bypass Grafting, The Journal of Thoracic and Cardiovascular Surgery, 77–82, Jan. 2000.

Damiano, Jr et al., Initial US Clinical Trial of Robotically Assisted Endoscopic Coronary Artery Bypass Grafting, Journal of Thoracic and Cardiovascular Surgery, 77–82, Jan. 2000.

Falk, Volkmar et al., Total Endoscopic Computer Enhanced Coroanry Artery Bypass Grafting, European Journal of Cardio–thoracic Surgery, 38–45, 2000.

Falk, Volkmar et al., Total Endoscopic Off–Pump Coronary Artery Bypass Grafting, The Heart Surgery Forum, 29–31, Feb. 21, 2000.

Tabaie, Harold et al., Endoscopic Coronary Artery Bypass Graft Procedure with Robotic Assistance, The Heart Surgery Forum, 1–9, Sep. 7, 1999.

Falk, Volkmar et al., Endoscopic Coronary Artery Bypass Grafting on the Beating Heart Using a Computer Enhanced Telemanipulation System, The Heart Surgery Forum, 1/8, Jul. 7, 1999.

Falk, Volkmar et al., Total Endoscopic Off–Pump Coronary Artery Bypass Grafting, The Heart Surgery Forum, 1–4, Feb. 21, 2000.

Kappert, Utz et al., Closed Chest Coronary Artery Bypass on the Beating Heart, The Heart Surgery Forum, 1–4, Jun. 8, 2000.

Farrar, David, Development of a Prosthetic Coronary Artery Bypass Graft, The Heart Surgery Forum, 1–6, Jan. 13, 2000.

Falk, Volkmar et al., Endoscopic Doppler for Detecting Vessels in Closed Chest Bypass Grafting, The Heart Surgery Forum, 1–5, Jun. 24, 2000.

Zamvar, Vipin, et al., Bleeding from the Lung Surface: A Unique Complication of Off–Pump CABG Operation, The Heart Surgery Forum, 1–2, Nov. 30, 2000.

Loulmet, Didier et al., Endoscopic Coronary Artery Bypass Grafting with the Aid of Robotic Assisted Instruments, The Journal of Thoracic and Cardiovascular Surgery, 4–10, Jul. 1999.

Falk, V et al., Quality of Computer Enhanced Totally Endoscopic Coronary Bypass Graft Anastomosis, European Journal of Cardio–thoracic Surgery, 260–265, 1999.

Mohr, Friedrich et al., Computer–Enhanced "Robotic" Cardiac Surgery: Experience in 148 Patients, The Journal of Thoracic and Cardiovascular Surgery, 842–853, 5/01.

Boyd, W et al., A Comparison of Robot–Assisted Versus Manually Constructed Endoscopic Coronary Anastomosis, The Annals of Thoracic Surgery, 1–9, Jan. 31, 2000.

* cited by examiner

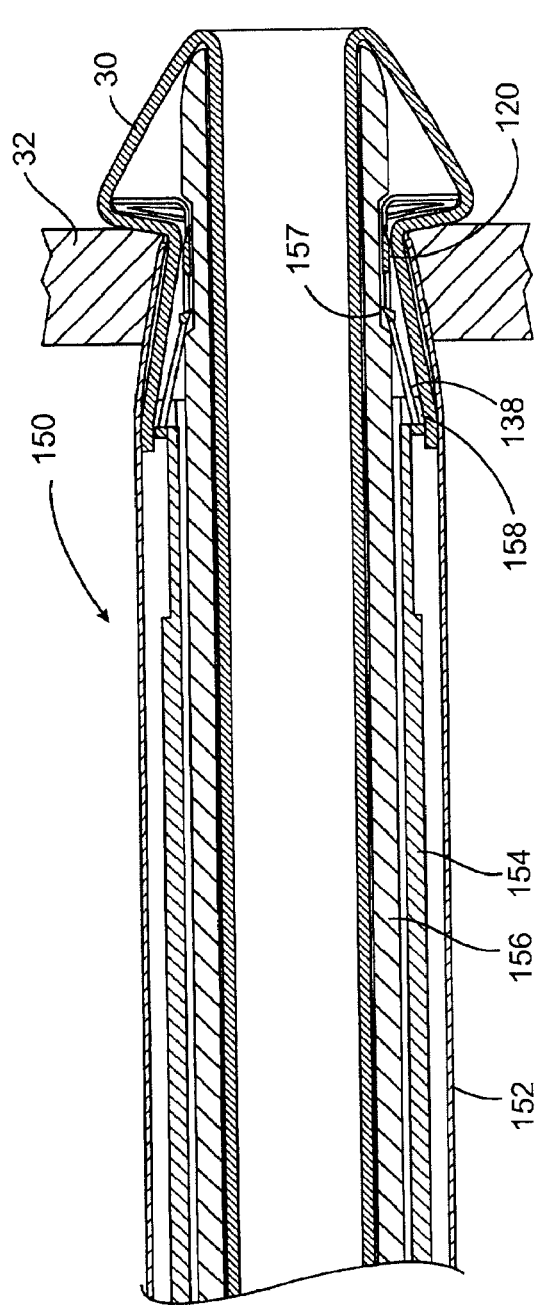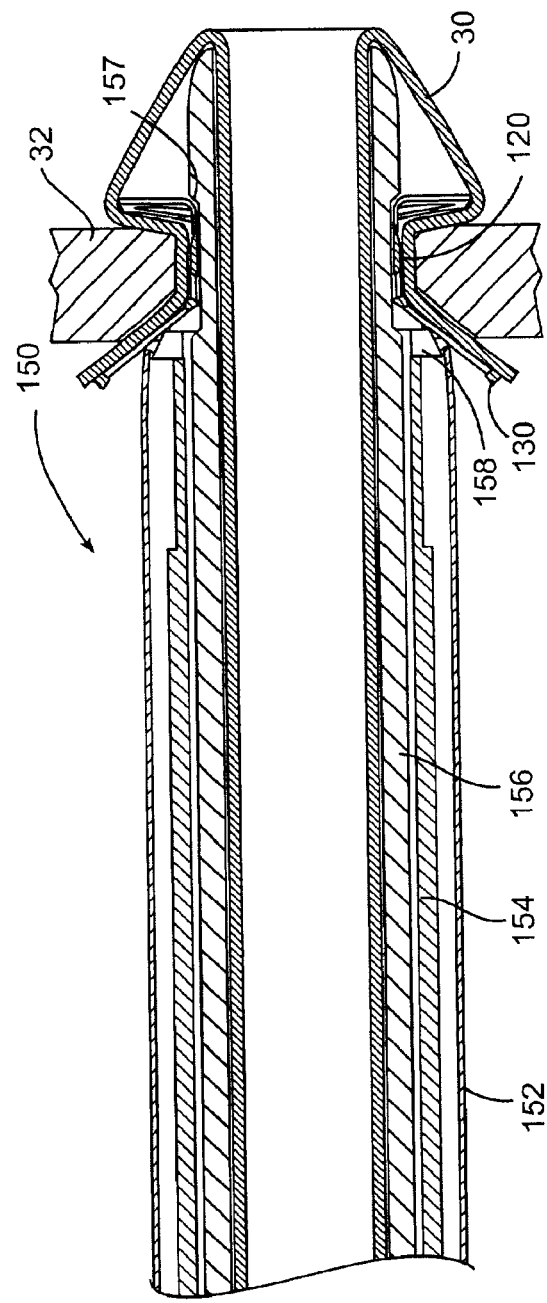

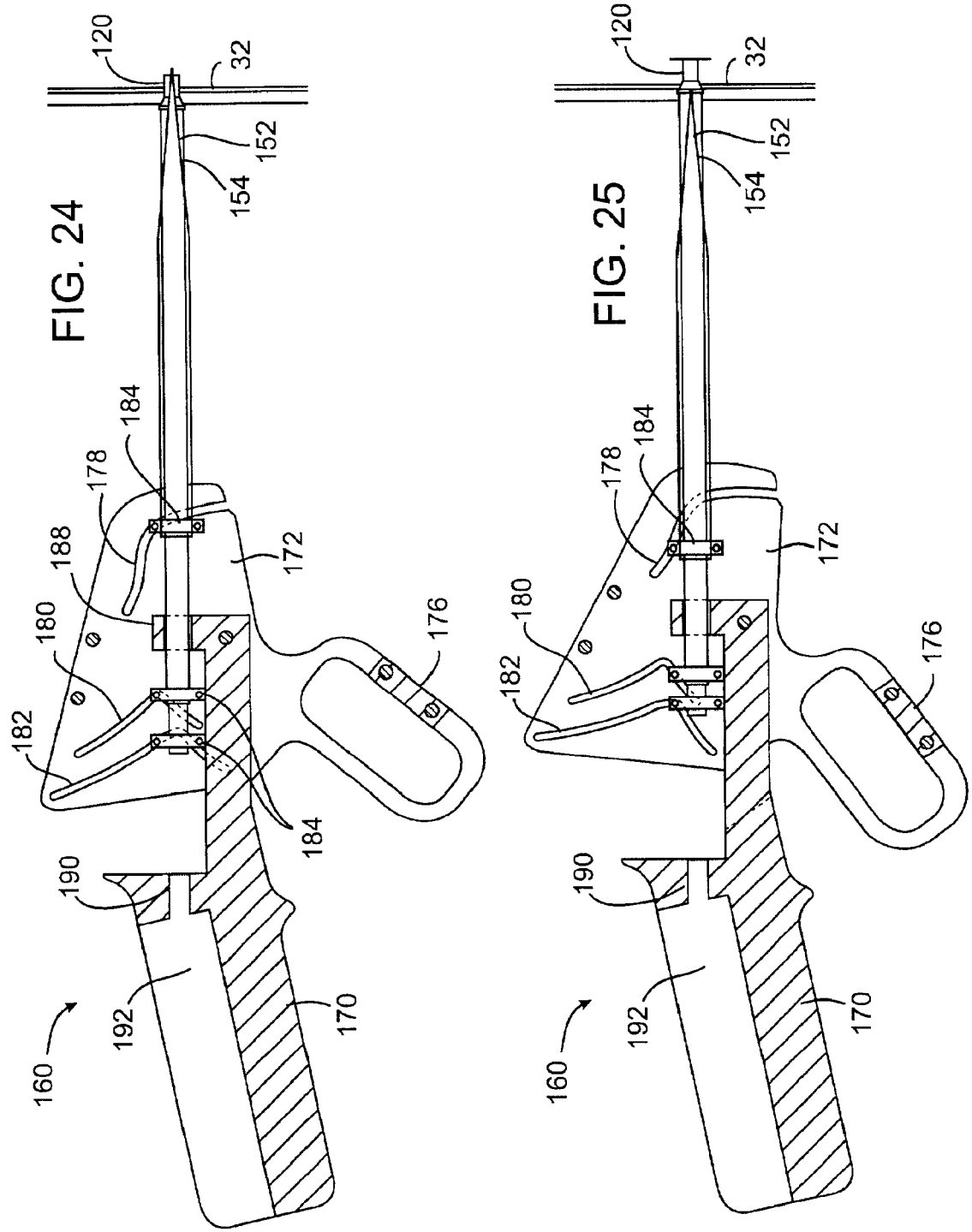

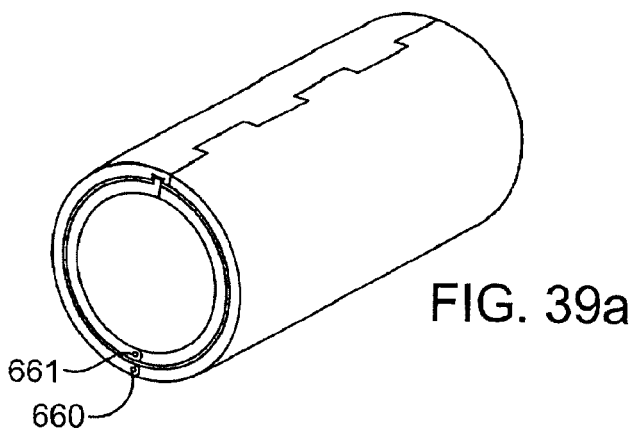
FIG. 39a
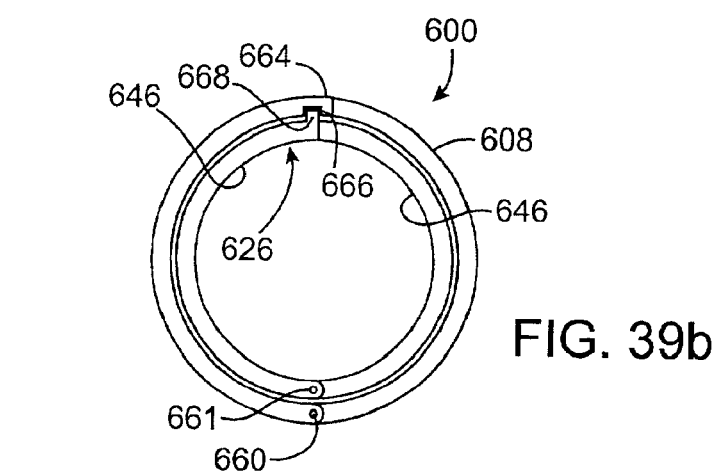
FIG. 39b
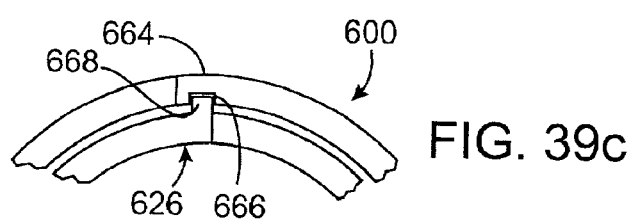
FIG. 39c
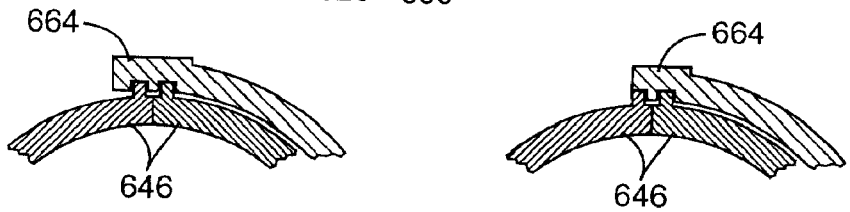
FIG. 39d
FIG. 39e
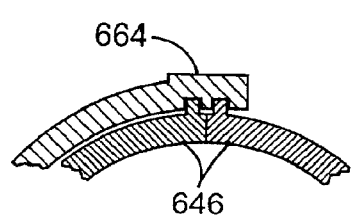
FIG. 39f
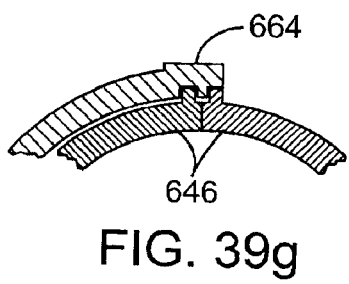
FIG. 39g

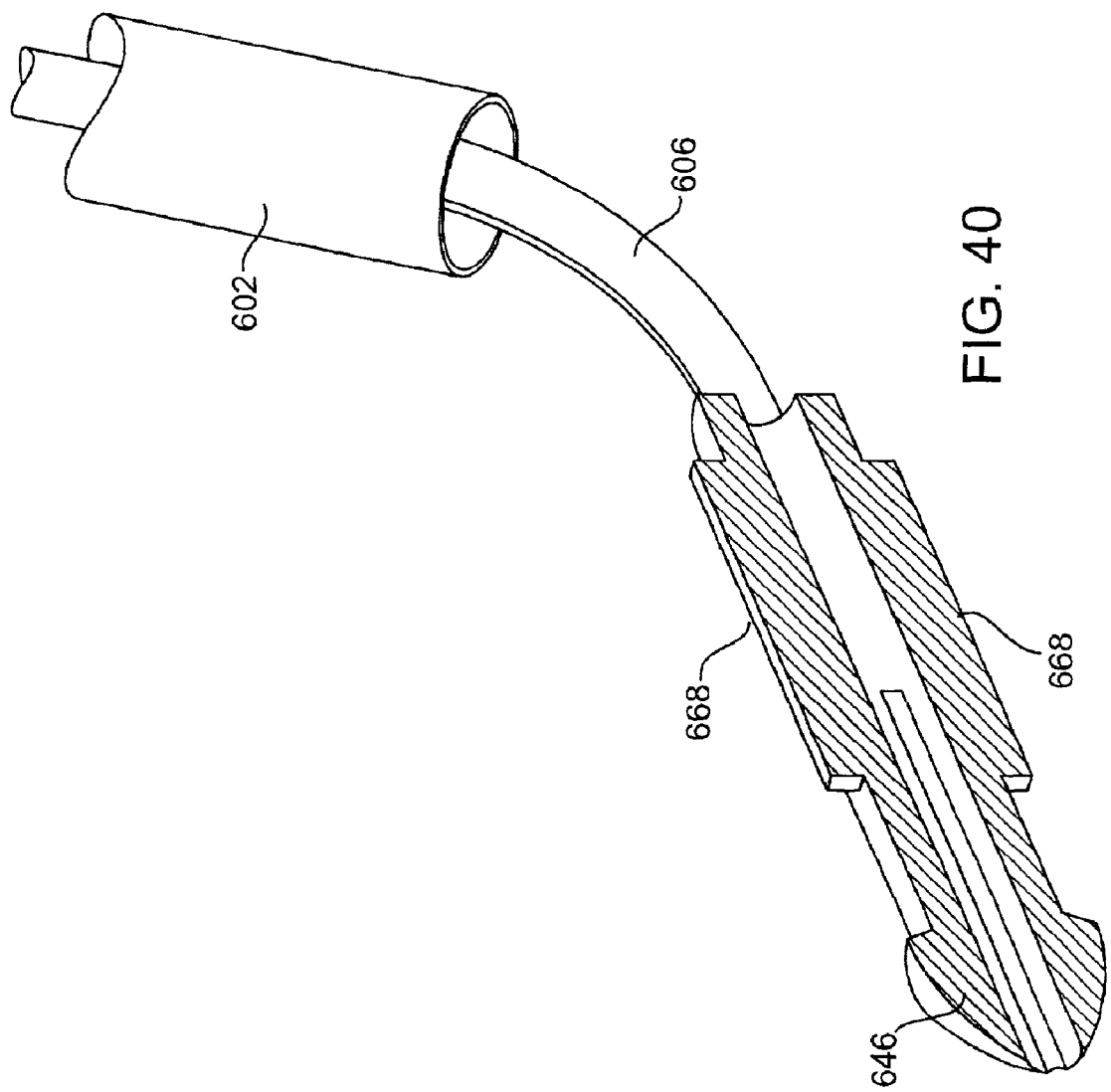

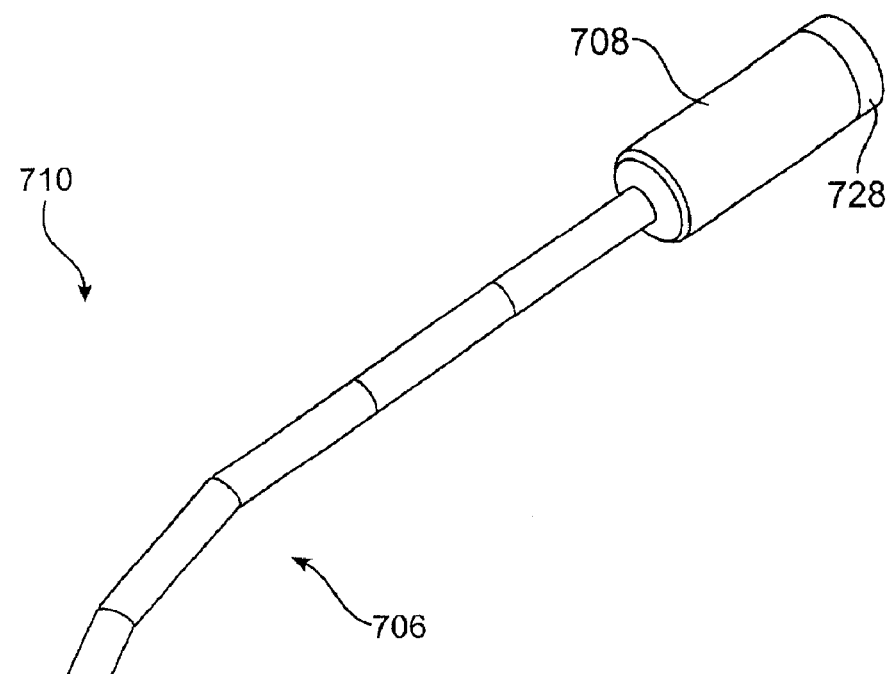
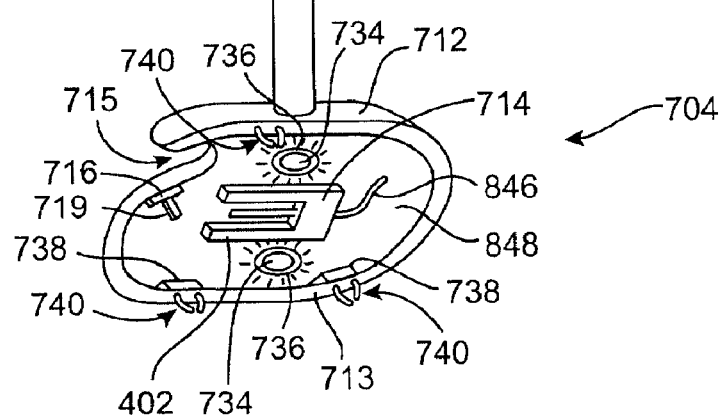
FIG. 49

METHOD AND SYSTEM FOR PERFORMING CLOSED-CHEST BYPASS

This application claims the benefit of U.S. Provisional Application No. 60/247,029, filed Nov. 13, 2000.

FIELD OF THE INVENTION

The present invention relates generally to a system and procedure for performing minimally-invasive coronary artery bypass graft (CABG) surgery.

BACKGROUND

Anastomosis is a procedure where two separate tubular or hollow organs are surgically grafted together to form an intercommunication between them. Vascular anastomosis involves creating an anastomosis between blood vessels to create or restore blood flow. The vascular anastomosis procedure is routinely performed during the treatment of a variety of conditions, including coronary artery disease, diseases of the great and peripheral vessels, organ transplantation, traumatic injury and other vascular abnormalities. When a patient suffers from coronary artery disease (CAD), an occlusion or stenosis in a coronary artery restricts blood flow to the heart muscle. In order to treat CAD, the area where the occlusion occurs is bypassed to reroute blood flow by grafting a vessel in the form of a harvested artery or vein, or a prosthesis. When the vessel is grafted to bypass the blocked coronary artery, the occlusion is circumvented and adequate blood flow is restored to the heart muscle. This treatment is known as a coronary artery bypass graft procedure (CABG).

When a conventional CABG is performed, a large incision is typically made in the chest of a patient and the sternum is sawed apart and separated in order to allow access to the heart of the patient. Moreover, the patient is connected to a heart-lung machine which circulates and oxygenates the blood of the patient. After the heart-lung machine is connected to the patient, the patient's heart is stopped in order to facilitate the vascular anastomosis. Sawing the sternum and stopping the heart are both traumatic events, and require substantial recovery time, particularly in older patients. Further, the patient may experience a variety of physiologic abnormalities after disconnection from the heart-lung machine.

In order to minimize the trauma to the patient induced by the CABG, less invasive techniques have been used. These less invasive techniques include making a series of small incisions in the patient's chest. Once the incisions are made, surgery is performed through the incisions with the aid of visualizing scopes. This procedure is often referred to as closed chest or port-access CABG surgery. The less invasive techniques may be performed on a beating heart without use of the heart-lung machine in order minimize trauma to the patient.

In both conventional and less invasive CABG techniques, a surgeon typically sutures one end of the graft vessel to the coronary artery beyond the narrowed area and the other end of the graft vessel to a blood supplying artery, such as the aorta, in order to bypass the occlusion. Prior to suturing the graft vessel to the coronary arteries, called target vessels, an incision is made in the target vessel to allow suturing of the graft vessel to the target vessel. Typically, the surgeon cuts the incision in the target vessel to an appropriate length depending on a size of the graft vessel in order to suture the graft vessel to the target vessel. However, a great amount of skill and time is required in making the incision, aligning the graft vessel to the incision and performing the anastomosis due to the small size and configuration of the target blood vessel. Closed chest bypass graft surgical procedures using sutured anastomosis techniques are disclosed in U.S. Pat. Nos. 5,452,733 and 5,735,290.

Sutureless techniques for performing anastomosis have also been proposed. Such techniques are disclosed in U.S. Pat. Nos. 3,254,650; 3,774,615; 4,350,160; 4,352,358; 4,368,736; 4,523,614; 4,553,542; 4,593,693; 4,607,637; 4,624,255; 4,624,257; 4,657,019; 4,747,407; 4,907,591; 4,917,087; 4,917,090; 4,917,091; 5,119,983; 5,234,447; 5,336,233; 5,366,462; 5,456,714; 5,571,167; 5,669,918; 5,676,670; 5,695,504; 5,702,412; 5,707,380; 5,725,544; 5,797,920; 5,817,113; and 5,904,697. However, these existing sutureless techniques for performing anastomoses have certain shortcomings that render them less practical or desirable for use in performing coronary bypass surgery in the closed chest.

Consequently, a need still exists for an automated system for performing bypass graft surgery which allows a surgeon to make a precise anastomosis between each end of a graft vessel and a corresponding target vessel.

SUMMARY

In one aspect of the invention, a coronary artery bypass graft procedure is performed via one or more incisions made in the patient to create a point of entry to the thoracic cavity, each incision fitted with a trocar port. One of the trocar ports has an oval cross-section, and is large enough to allow one or more anastomotic tools to pass through it into a patient's chest. By performing the procedure while the patient's chest is closed and the heart is beating, the patient can recover more rapidly than from a conventional open-chest, stopped-heart procedure, and the procedure can be performed more quickly.

In another aspect of the invention, a vein measurement device is used to measure the distance between the proximal and distal anastomotic sites on the target vessels for each graft. Measuring units on the vein measurement device may be marked at their actual size, or at a size scaled to compensate for the expansion of the graft vessel during perfusion. Thus, the surgeon can accurately determine the optimum length for each graft vessel before it is cut and placed.

In another aspect of the invention, a splittable proximal anastomosis tool is adapted to split after deploying an anastomotic device at the proximal anastomosis site. By splitting the tool, the graft vessel can be released within the thoracic cavity of the patient after performing the anastomosis at the proximal site. Also, by splitting the tool, a distal clamp can be placed on the graft vessel before the proximal anastomosis is performed, facilitating the procedure, and allowing the distal anastomosis to be performed first if desired. The splittable proximal anastomosis tool may be articulated to move within the thoracic cavity relative to the aorta within a range of angles. This articulation allows the splittable proximal anastomosis tool to be placed substantially normal to the ascending or descending aorta or other arterial vessel, in order to gain full access to potential proximal anastomosis sites.

In another aspect of the invention, an integrated stabilizer is used to stabilize one or more tools relative to the surface of the beating heart at a distal anastomotic site. The integrated stabilizer includes a stabilizer head connected to a linkage that in turn is connected to a handle. The linkage may include a compliant cable through a center bore of the linkage. The linkage may be rigid upon insertion of the integrated stabilizer into the chest cavity through the oval trocar port. Once the stabilizer head is in position on the heart, the linkage switches to a preselected compliance to track with the motion of the heart. In this way, a stabilized, relatively motion-free portion of the heart is created around the distal anastomotic site.

In another aspect of the invention, a distal anastomotic tool is utilized to connect a distal end of the graft vessel to a target vessel. The distal anastomotic tool is included in the integrated stabilizer. The distal anastomotic tool includes an anvil that enters the target vessel, against which fasteners are pressed to create a compliant anastomosis between the graft vessel and the target vessel. Cables or other actuation mechanisms are connected to the distal anastomotic tool and to a handle or other device extending out of a trocar port, allowing the surgeon to actuate the tool. A cam path defined in the integrated stabilizer that is followed by the distal anastomotic tool may be used to control the pathway of the anvil as it approaches, penetrates and tensions the target vessel in the course of performing distal anastomosis.

In another aspect of the invention, an epicardial dissector is used to remove the epicardium from the target vessel at a distal anastomotic site, as needed. The epicardial dissector may be built into the integrated stabilizer or provided separately from it. By using the epicardial dissector, a surgeon can safely and accurately remove the epicardium, if necessary, from the target vessel at the distal anastomotic site.

In another aspect of the invention, a coronary artery bypass graft procedure is performed utilizing the tools described above. These tools are inserted into and removed from the thoracic cavity of the patient through the appropriate trocar ports.

BRIEF DESCRIPTION OF THE DRAWINGS

FIG. 21 is a side cross sectional view of the anastomosis device deployment system with an expanded first annular flange.

FIG. 22 is a side cross sectional view of the anastomosis device deployment system expanding a second annular flange.

FIG. 24 is a schematic side cross-sectional view of the deployment tool shown during an anastomosis device insertion step.

FIG. 25 is a schematic side cross-sectional view of the deployment tool shown during an anastomosis device expansion step.

FIG. 38b is an exploded view of the tool of FIG. 38a.

FIG. 39a is a perspective view of another embodiment of a splittable anastomosis tool.

FIG. 39b is an end view of the tool of FIG. 39a.

FIG. 39c is a detail view of the end of the tool of FIG. 39a.

FIG. 39d is a detail cross-section view of the tool of FIG. 39a across a notch extending from the right.

FIG. 39e is a detail cross-section view of the tool of FIG. 39a across another embodiment of a notch extending from the right.

FIG. 39f is a detail cross-section view of the tool of FIG. 39a across a notch extending from the left.

FIG. 39g is a detail cross-section view of the tool of FIG. 39a across another embodiment of a notch extending from the left.

FIG. 40 is a perspective view of an expander segment utilized within a splittable anastomosis tool.

FIG. 41b is a side view of an anastomosis tool utilizing the shaft of FIG. 41a.

FIG. 49 is a perspective view of a surgical tool having an integrated stabilizer.

The use of the same reference symbols in different figures indicates similar or identical items.

DETAILED DESCRIPTION

The coronary artery bypass graft surgery (CABG) procedure described herein involves performing two anastomotic procedures, one on each end of a graft vessel. Each end of the graft vessel is attached to a target vessel with an end-to-side anastomosis. The proximal anastomosis is performed on one end of the graft vessel that is attached to the source of blood (e.g. the aorta) and the distal anastomosis is performed on the other end of the graft vessel that is attached to the destination of the blood flowing through it (e.g. a coronary artery). For each graft vessel, the proximal anastomosis procedure generally is performed before the distal anastomosis procedure. Alternately, the distal anastomosis procedure may be performed first for one or more of the grafts. During a single CABG procedure, multiple grafts may be placed, depending on the needs of the patient. For example, the patient may have blockages in three different coronary arteries, in which case three different grafts are placed, one for each coronary artery.

To begin the CABG procedure, one or more openings are made into the patient to gain access to the thoracic cavity. These openings may be keyhole incisions, or other types of incisions or openings. The location and number of the openings depend upon the location of the anastomotic sites for each particular patient, and on the type of approach to the heart. In one embodiment, three incisions are made in the left intercostal spaces. The largest of the three incisions preferably is made in the fourth or fifth intercostal space. The other two incisions are smaller, and are made in the adjacent intercostal spaces. Alternately, the incisions may all be made the same size. Further, the other two incisions may be made in different locations as needed for a particular patient.

Figure 1:
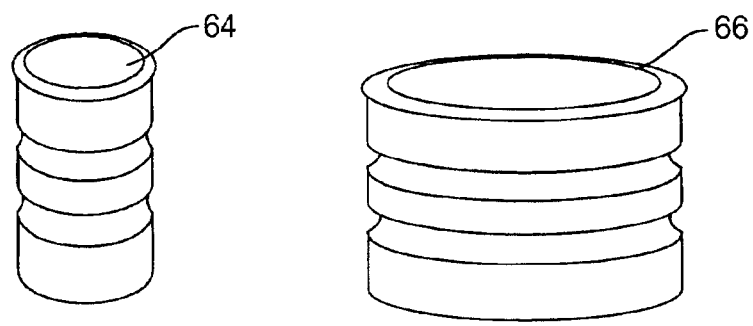
FIG. 1 is a perspective view of two sizes of trocar ports.
Figure 2:
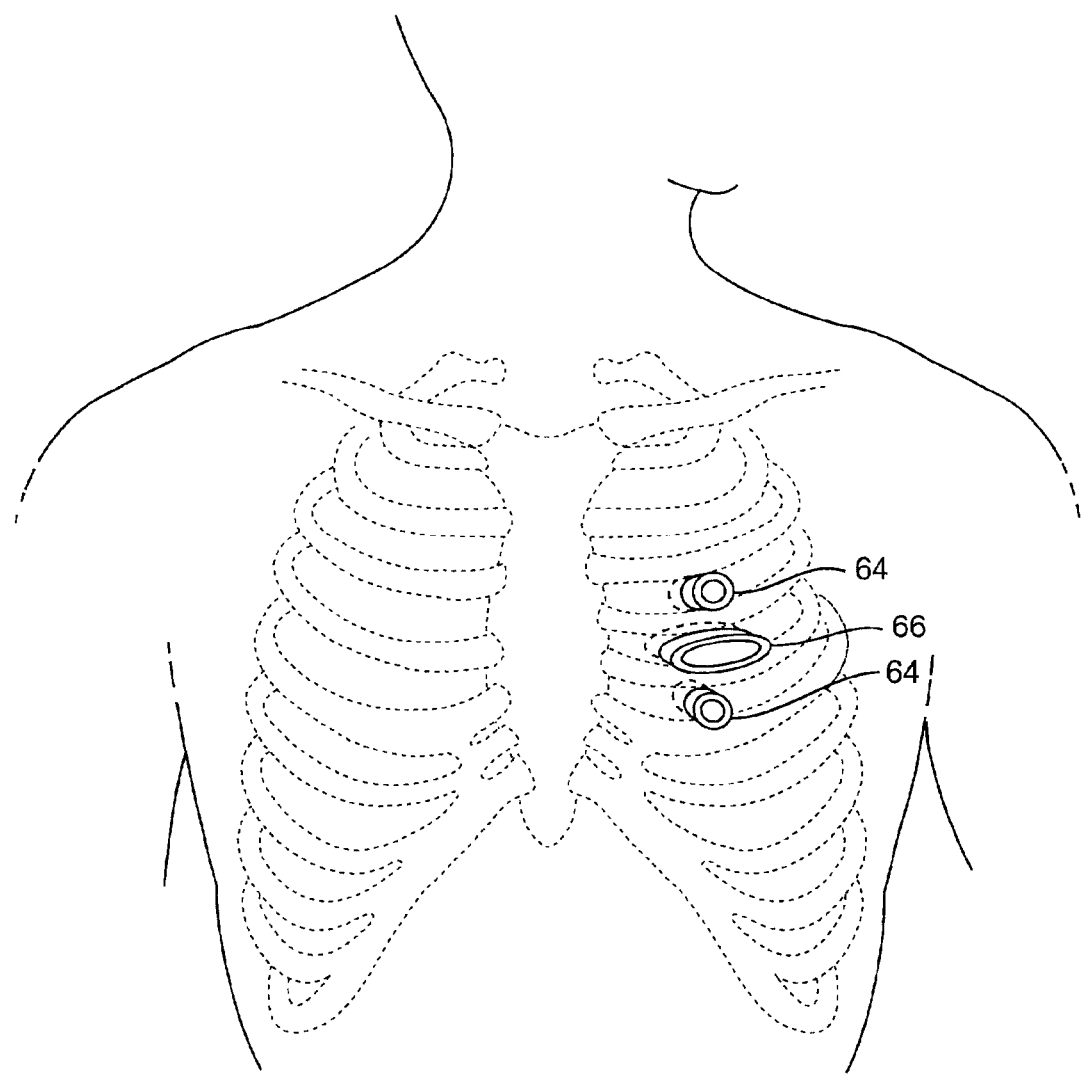
FIG. 2 is a schematic view of a patient having three incisions into the thoracic cavity, each in a different intercostal space, with trocar ports inserted therein.

Referring to FIG. 1, a small trocar port 64 and a large trocar port 66 are shown. Each trocar ports 64, 66 includes a cutting tool (not shown) through its center that makes an opening in the chest while the trocar port 64 is deployed into the chest wall. The cutting tool may be a spike or other cutting or puncturing device, which is removed from the trocar port 64, 66 when the trocar port 64, 66 is in position in the chest wall. The combination of a trocar port 64, 66 and a cutting tool is standard in the art, and such combined devices are manufactured by Guidant and Ethicon, among other manufacturers. Alternately, each opening in the chest is made first, and the trocar port 64, 66 inserted into that opening after. One of the trocar ports 64, 66 is placed in each opening. Referring as well to FIG. 2, the trocar ports 64, 66 are hollow tubes inserted into the incisions to hold them open and to prevent damage to the tissue defining the incision opening that may result from the motion of tools and other objects through the incision. The trocar ports 64, 66 may be made from plastic or any other suitable biocompatible material. The small trocar port 64 is a standard trocar port having a substantially circular cross section, substantially 15 mm to 22 mm in diameter. Other diameters may be used. Further, the small trocar port 64 may have a different cross section. A small trocar port 64 is placed in each of the smaller incisions. The large trocar port 66 has an oval cross section, measuring substantially 45 mm×22 mm along its major and minor axes, respectively. Other dimensions may be utilized if desired. Further, the large trocar port 66 may instead have a different cross-section if desired, as long as adequate space is provided for the movement of the appropriate surgical tools through that trocar port 66. A large trocar port 66 is placed into the largest opening in the chest wall. One of the first trocar ports 64 is dedicated for use with an endoscope or other visualizing device, and the other small trocar port 64 is used as needed for insertion of standard endoscopic tools, such as an endoscopic harmonic scalpel or other cutting tool, an endoscopic clip applicator or other ligation tool, and/or an endoscopic forceps. The large trocar port 66 is used for the insertion of tools utilized for performing anastomosis between a graft vessel and target vessels. The trocar ports 64, 66 may be utilized differently, as needed.

The CABG procedure first may be performed on the left side of the heart. Three openings are made on the left side of the chest in the appropriate left intercostal spaces, and the trocar ports 64, 66 are inserted therein. Alternately, more or fewer openings may be made in the left side of the chest. The patient is intubated with a bifurcated breathing tube that allows for the left lung and right lung to be ventilated or deflated separately. Alternately, another device or method may be used to deflate one lung at a time. The left lung is then deflated. The trocar ports 64, 66 are used without pressurizing the thoracic cavity, because adequate space for performing the procedure is obtained within the thoracic cavity by deflating each lung in turn, as needed. Thus, the trocar ports 64, 66 need not provide pressure seal capability. However, the trocar ports 64, 66 may include seals or other mechanisms for maintaining pressure inside the thoracic cavity during the CABG procedure.

The trocar ports 64, 66 in the left side of the chest may be used to take down the left internal mammary artery (LIMA) and/or the right internal mammary artery (RIMA), if one or both of those arteries are to be used as graft vessels. "Taking down" the LIMA and/or RIMA refers to severing at least one end of the LIMA and/or RIMA in the course of preparing it for use as a graft vessel. The RIMA instead may be taken down through trocar ports 64, 66 on the right side of the chest, as described below. When the LIMA and/or RIMA are taken down, the distal end of the artery is severed and the other remains attached. In this way, the LIMA and/or RIMA can be stored in the chest for anastomosis to a target vessel later in the procedure. The LIMA and/or RIMA are assumed to include a tissue pedicle for handling. However, the LIMA and/or RIMA may be handled without a tissue pedicle, at the choice of the surgeon. The proper length to cut the LIMA and/or RIMA is determined after the distal anastomotic site or sites are selected, as described later in this document. If needed, an additional or different graft vessel or vessels may be harvested from the patient, such as the greater saphenous vein or the radial artery. Harvesting the saphenous vein, radial artery or other blood vessel for use as a graft vessel is standard to one skilled in the art.

In another embodiment, only one large trocar port 66 is utilized. The larger incision is made in the sub-xyphoid area, allowing better access to the entire surface of the heart. A large trocar port 66, or another trocar port specifically designed for the sub-xyphoid approach, is inserted into that incision. By using the sub-xyphoid approach, the surgical tools utilized in the procedure across the entire heart can be inserted through the single sub-xyphoid trocar port 66, minimizing the number of incisions that are made in the patient. One or two incisions may be cut into the left and/or right side of the chest in the intercostal space, as needed, and each is fitted with a small trocar port 64. In other respects, the procedure continues as described with two second trocar ports 66. Alternately, the sub-xyphoid opening is used in conjunction with one or more other openings and trocar ports 64, 66 in the patient's chest. As one example, the sub-xyphoid opening may be used for performing distal anastomosis, while one or more trocar ports 64, 66 in one or more intercostal spaces are used to harvest the LIMA and/or RIMA and to perform proximal anastomosis.

After deflating the patient's left lung, the aorta can be accessed and denuded locally at the proximal anastomosis site, in preparation for the proximal anastomosis. Denuding can be done by conventional endoscopic methods at any time during the procedure after the trocar ports have been placed and before the proximal anastomosis is performed.

The surgeon gains access to the heart by opening the pericardium. Opening the pericardium is a standard procedure to one skilled in the art. The pericardium is preferably opened by incising it longitudinally from the aortic root down to the apex of the heart, to gain access to the coronary arteries. Conventional endoscopic tools may be used. The resulting incision is typically 80–100 mm long. However, a longer or shorter incision may be cut, as needed. Alternately, two substantially parallel incisions are made in the pericardium, one on the left side of the heart and one on the right.

Once the pericardium has been opened, the blockage or obstruction in the target vessel may be located. A number of methods can be used to locate the blockage or obstruction. An experienced cardiovascular surgeon memorizes the angiogram of the patient and the location of the blockage or blockages and key reference points, then mentally compares the memorized image to the visualized surface of the heart using those key reference points. The angiogram may be accessible to the surgeon in some manner during the procedure. Alternately, the location of a blockage can be identified by viewing the target vessel visually through an endoscope and noting slight color differences in it. Alternately, a blockage in the target vessel can be located using a palpitation tool, ultrasound probe or other vibrating tool applied to the target vessel. The presence of atherosclerotic plaque inside the vessel causes the response of the vessel to change in response to the applied vibrations. By observing the response to these vibrations along the length of the vessel, the location of the blockage can be ascertained. Alternately, conventional fluoroscopy of the target vessel is used to locate the blockage or blockages. Alternately, indocyanine green (ICG) dye is injected into the target vessel, causing the target vessel to glow green under an ultraviolet light. The blockage or blockages are then located visually by shining ultraviolet light onto the target vessel and detecting areas of the target vessel from which less light is emitted. Alternately, thermal sensing is used to locate a blockage or blockages in the target vessel. A saline mister, a carbon dioxide blower, or other device or method is used to cool the target vessel. Because the plaque forming the blockage has a different thermal mass than the surrounding tissue, the surrounding tissue cools at a faster rate than the blockage and the target vessel walls adjacent to the blockage. The blockage can then be visualized with a thermal sensor. Alternately, a pulse of carbon dioxide or other gas or gases is transmitted substantially normal to the surface of the target vessel. A receiver measures the amount of energy reflected from the target vessel to determine the amount of damping therein. Because the target vessel is stiffer in the area of blockage, less damping is present in that area. Thus, areas of the target vessel exhibiting less damping are the areas of blockage. Other methods or devices for determining the location of the blockage may be used. After the blockage is located, the distal anastomotic site is selected. This site is located on the target vessel downstream of the blockage. If there is more than one blockage, the distal anastomotic site is selected to be downstream of the most-downstream blockage. However, the distal anastomotic site may be selected to be at a different location, depending on the particular patient. The distal anastomotic site may be marked with dye, ink or a different marker on the surface of the heart, to make it easier to find later in the procedure.

In another embodiment, access to the heart can be obtained without making an incision in the pericardium, by guiding a catheter through one of the incisions in the chest wall into the intrapericardial space. In such an embodiment, the distal anastomotic site may be located prior to or during surgery using noninvasive means such as angiography or ultrasound. Such means are utilized in this embodiment because the pericardium covers the heart, preventing effective direct visualization of the target vessel. Alternately, a visualization device is built into the catheter, such that the surgeon can view the target vessel and locate the blockage, and hence the distal anastomotic site, with that visualization device.

Figure 4:
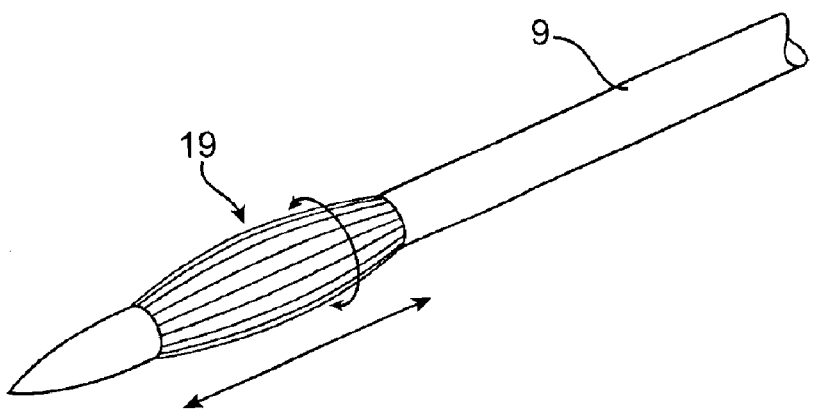
FIG. 4 is a perspective view of a intrapericardial directing tool.
Figure 5:
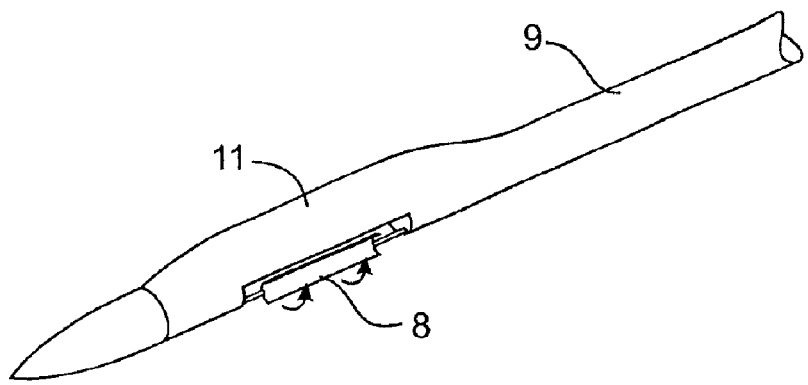
FIG. 5 is a perspective view of another embodiment of a intrapericardial directing tool.
Figure 6:
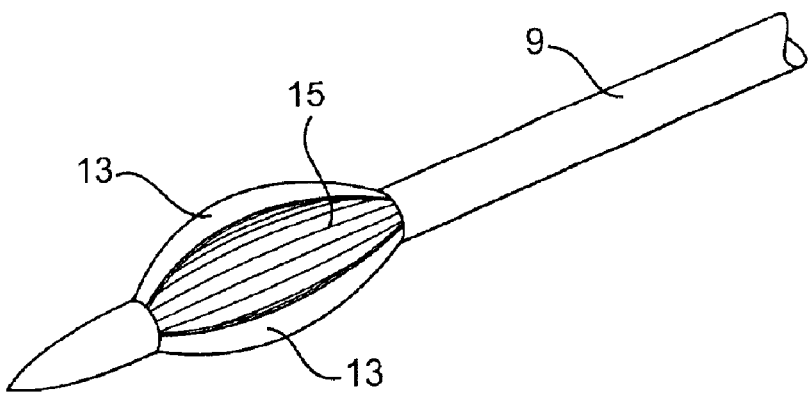
FIG. 6 is a perspective view of another embodiment of a intrapericardial directing tool.

Referring to FIGS. 4–6, in the intrapericardial method, a catheter 9 is inserted into the pericardium through the space along the ascending aorta just above the coronary artery. The catheter 9 may also be inserted through an incision in the pericardium. Alternately, an incision is made in the aorta, and the catheter is guided into the intrapericardial space through the wall of the aorta. Once the catheter 9 is positioned within the pericardial space, the catheter 9 is directed to the distal anastomotic site by pushing and pulling to move the catheter 9 in a first dimension and by rotating a rotary member on an end of the catheter to move the catheter in a second dimension. The catheter 9 is maintained on the heart surface while being maneuvered because it is trapped between the heart and the pericardium.

FIG. 4 shows a intrapericardial directing tool comprising a rotary member 19 that can be rotated remotely through a catheter 9. FIG. 5 shows an alternative embodiment of a intrapericardial directing tool comprising a rotary member 8 that can rotate freely in a radial insertion space created by a tissue separating member 11. The separating member creates a space between the heart tissue and the pericardium thus allowing the rotary member to freely rotate along the surface of the heart. FIG. 6 shows an alternative embodiment of the intrapericardial directing tool including two separating members 13 and a rotary member 15.

Figure 7:
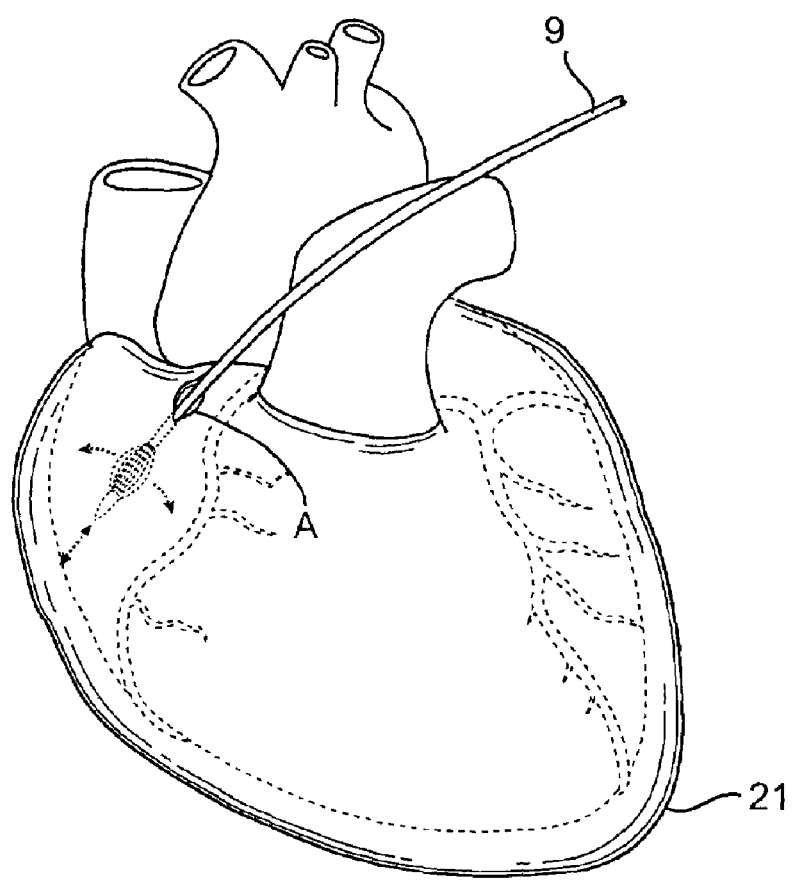
FIG. 7 is a perspective view of the heart through the intact pericardium, showing a catheter inserted into the intrapericardial space.
Figure 8:
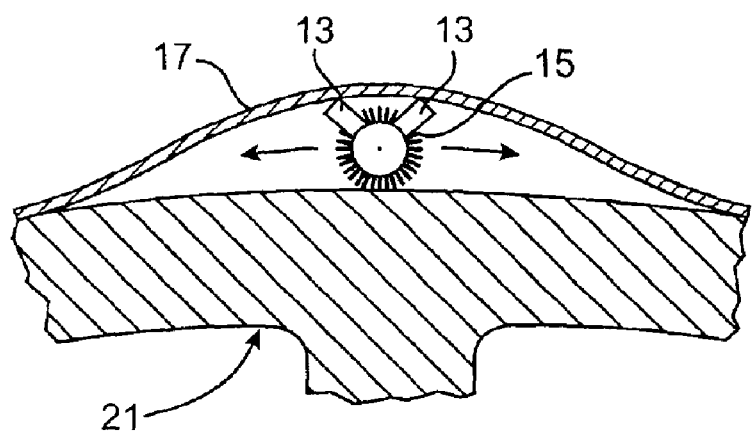
FIG. 8 is a cross-section view of the tool of FIG. 6 inserted into the intrapericardial space.

FIG. 7 shows the intrapericardial directing tool of FIG. 6 being inserted into the intrapericardial space. The catheter 9 is threaded under the pericardium through an exposed area or incision A located near the ascending aorta just above the coronary artery. FIG. 8 shows a cross-section of the intrapericardial directing device of FIG. 6 inserted between the pericardium 17 and the surface of the heart 21. During insertion, the pericardium keeps the catheter 9 closely approximated to the surface of the heart thus allowing accurate positioning of the catheter in the intrapericardial space. Lateral (side-to-side) movement is achieved by rotating the rotary member 15 remotely through the catheter 9 whereas forward and backward movement can be achieved by pushing or pulling the catheter 9. The catheter 9 can be guided to the intended anastomosis sites using a visualization method such as fluoroscopy. Once the catheter 9 is in position, the anastomosis procedure can be performed by a intrapericardial method with various tools. By using the intrapericardial method, the proximal anastomosis and distal anastomosis can be performed while making only a small opening in the pericardium or leaving the pericardium intact.

The graft vessel can be routed in one of several different ways where a intrapericardial approach is used. In one embodiment, the graft vessel is kept entirely within the pericardium. That is, both the proximal and distal anastomoses are performed inside the pericardium, and remain inside the pericardium. The graft vessel is pulled into the intrapericardial space via the incision described above through which the catheter is inserted. This method of handling the graft vessel provides additional protection to the anastomosis sites and to the graft vessel, but limits the mobility of tools utilized to perform the anastomoses, and is therefore a more difficult procedure to perform. In another embodiment, a small incision is made at each distal anastomotic site, and the graft vessel is pulled into the intrapericardial space via the incision described above through which the catheter is inserted. The distal end of the graft vessel is led out of the incision at the distal anastomotic site, then curved in back through that incision. In this way, the size of the individual incisions to the pericardium is minimized. In another embodiment, a small incision is made at each distal anastomotic site. The tools are navigated through the intrapericardial space, and the graft vessel is kept outside the pericardium.

The pericardium can be handled in other ways. In another embodiment, a small incision is made in the pericardium at each distal anastomotic site. Each graft vessel is led through that small incision to the distal anastomotic site, where distal anastomosis is performed. In this way, the graft vessel need not traverse the intrapericardial space. Tools can be moved, and anastomosis can be performed, more readily than via a intrapericardial approach, because the tools are not navigated through the intrapericardial space.

Once the distal anastomotic site is reached, a guidewire is passed through the catheter and fixed to the tissue at the anastomosis site. This guidewire is then used for insertion and removal of tools for subsequent procedures.

Figure 3:
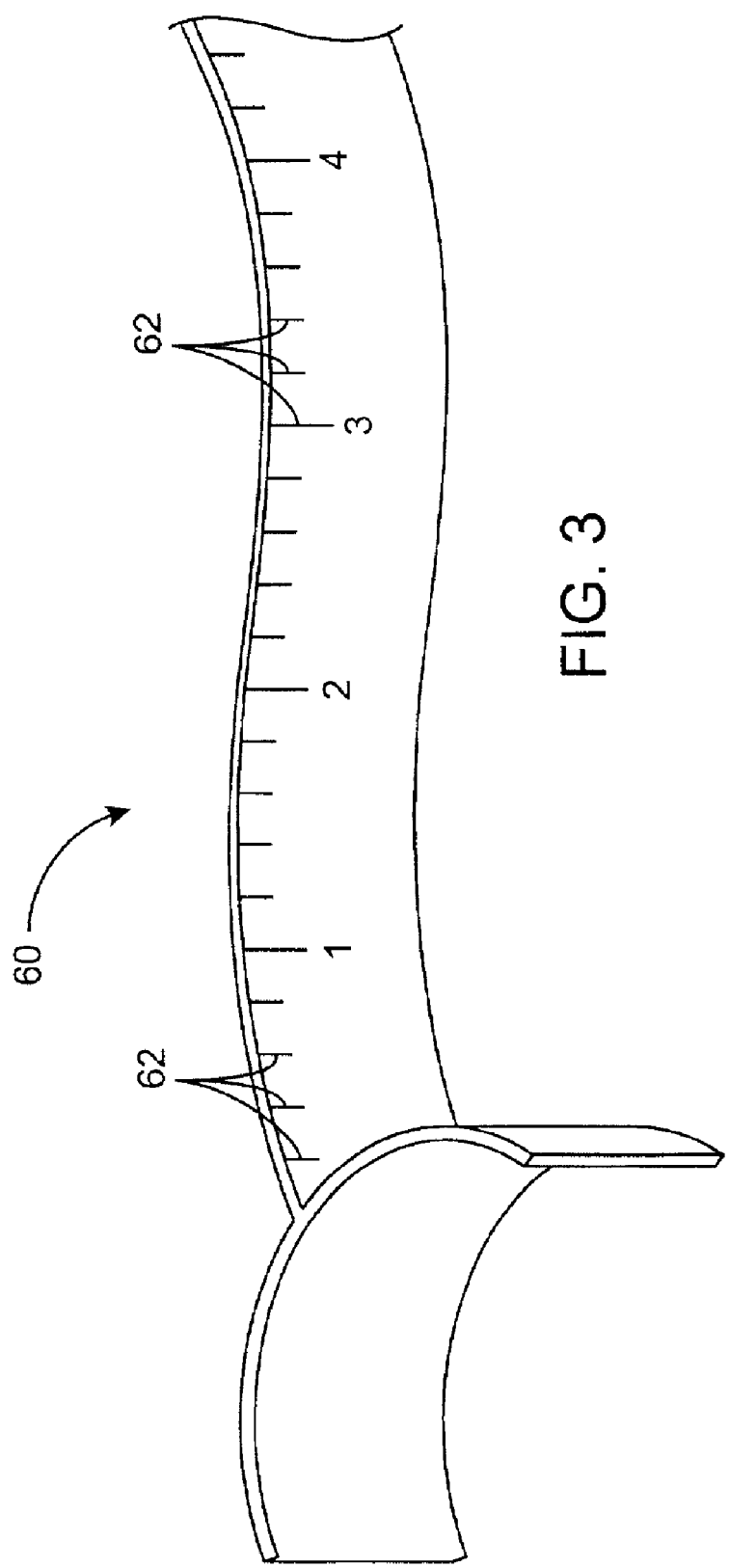
FIG. 3 is a perspective view of a vein measurement device.

After locating the blockage, the location of the intended distal anastomotic site on the target vessel (coronary artery) can then be determined, and subsequently the length of graft vessel required for the bypass graft can be determined. The graft vessel should be long enough to span the distance between the distal and proximal target sites but not so long as to become kinked during the graft bypass procedure. Referring to FIG. 3, a vein measurement device 60 is used to measure the distance between the proximal and distal anastomotic sites for each graft, in order to determine the proper length for each graft vessel before the graft vessel is cut and placed. The vein measurement device 60 is flexible and substantially non-stretchable, and is made of a sterilizable material that is safe for use within the chest cavity of the patient. This material may be a polymer such as nylon or polyester, or may be another material having the desired properties. The vein measurement device 60 is placed and held between the intended proximal and distal anastomotic sites using an aorta clip or holder that holds the vein measurement device 60 at the proximal anastomosis site. Alternately, the vein measurement device 60 may be placed and held with endoscopic forceps or other instruments operated through one or more trocar ports 64, 66. Alternately, the vein measurement device 60 may include a wire, handle or other protrusion that extends through a trocar port 64, 66, such that the surgeon may directly control the vein measurement device 60 without the need for endoscopic forceps or other intermediary tools. The particular instrument or instruments utilized to place and hold the vein measurement device 60 are not critical to the invention.

The vein measurement device 60 has distance markers 62 placed at discrete increments along its length in any desired units, such as English units or metric units. The distance markers 62 are readable through an endoscope that is operated through one of the incisions, and may be color-coded for ease in identifying them. The distance markers 62 may be provided on the vein measurement device 60 at their actual size. Alternately, the distance markers 62 may be scaled to compensate for expansion of the graft vessel upon perfusion. As is known to those skilled in the art, a graft vessel shrinks when harvested from the patient, then expands again when perfused with blood or other appropriate fluid before connecting that graft vessel to the target vessels. Thus, the distance markers 62 on the vein measurement device 60 may be scaled to indicate the length of graft vessel needed where the graft length is measured before the graft vessel is perfused.

In another embodiment, the graft vessel length can be determined prior to surgery using non-invasive imaging techniques such as ultrasound. A topographical representation of the heart can be obtained via such non-invasive imaging and a graft vessel length determined therefrom (e.g., by using software to calculate the desired length along a contour of the surface of the heart). Such an embodiment may be utilized both in surgery in which the pericardium is opened, and in surgery in which the intrapericardial space is accessed in a minimally-invasive manner, as described below.

Once the desired graft vessel length has been determined, a graft vessel can be cut to length. The graft vessel may be perfused, then cut to the length determined with the vein measurement device 60. Alternately, as described above, the length determined with the vein measurement device 60 may be scaled to correspond to the shrunken state of an graft vessel that is not perfused, which is then cut in accordance with the scaled length. Alternately, the graft vessel can be a vessel harvested from another part of the patient's body or a synthetic material (prosthesis). Once cut, a free graft vessel has two free ends: a distal end for attachment to a blood receiving vessel and a proximal end for attachment to a blood supplying vessel. If a LIMA and/or RIMA are harvested for use as graft vessels, one end of the vessel remains connected until it is ready for anastomosis. The graft vessel may be marked with a longitudinal dye line before or after cutting it to the appropriate length, in order to prevent twisting of the graft vessel later in the procedure.

Once the graft vessel has been cut to length, the distal end of the graft vessel can be prepared for the distal anastomosis procedure. The end of the graft vessel can be prepared using a graft vessel preparation device. The distal end of the graft vessel can be prepared for the distal anastomosis procedure by one person away from the patient, while another person denudes the aorta, incises the epicardium at the distal anastomotic site, measures the desired length of the graft vessel, or incises the pericardium. In this way, the surgery can be performed more efficiently. However, the distal end of the graft vessel can be prepared for the distal anastomosis procedure before or after the aorta is denuded and/or the epicardium is incised at the distal anastomotic site. Further, the graft vessel can be prepared for the distal anastomosis procedure either before or after the proximal anastomosis is performed.

The graft vessel preparation device allows the surgeon to accurately and precisely cut the graft vessel to ensure a proper fit with the target vessel. The graft vessel preparation device includes a clamp which holds the graft vessel. In one embodiment, the clamp has alignment holes which allow it to be mounted on corresponding alignment pins on a distal anastomotic tool such that the end of the graft vessel is held in proper orientation with respect to the target vessel during the distal anastomosis. An embodiment of this device is described below with reference to FIGS. 9–14.

Figure 9:
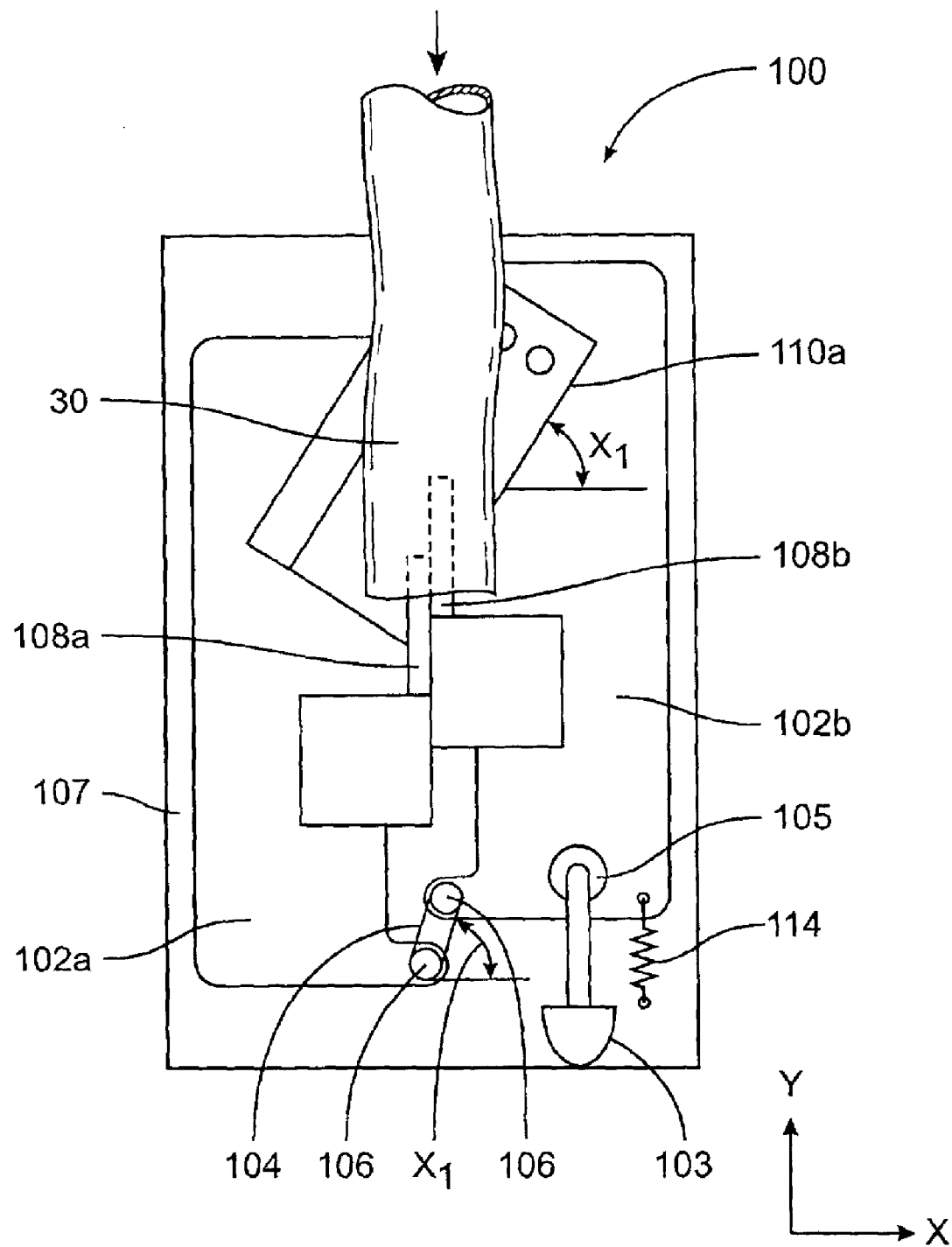
FIG. 9 is a top view of a graft vessel preparation device having a graft vessel inserted over spreader arms in preparation for grafting.

FIG. 9 shows one embodiment of a graft vessel preparation device 100, having a first base plate 102a rigidly mounted on a base 107, a second base plate 102b movably mounted on the base 107, spreader arms 108a and 108b, and an extension link 104. The graft vessel preparation device 100 also includes a first clamp portion 110a which is rotatably attached to the first base plate 102a and the second base plate 102b. A graft vessel 30 is shown inserted over spreader arms 108a and 108b in preparation for grafting to a target vessel 124. Spreader arm 108a and 108b are rigidly attached to first and second base plates 102a and 108b respectively. The extension link 104 is rotatably attached to the first and second base plates 102a and 102b with fasteners 106. The fasteners 106 may be any suitable type which allows a rotatable connection between the extension link 104 and the first and second base plates 102a and 102b. The first clamp portion 110a is rotatably connected to both the first base plate 102a and the second base plate 102b in the same manner as the extension link 104. The base plates 102a and 102b, the extension link 104 and the first clamp portion 110a together form a parallelogram linkage.

As shown in FIG. 9, the first clamp portion 110a and the extension link 104 are substantially parallel to one another such that the angle of the extension link 104 with respect to the X axis is substantially the same as the angle of the first clamp portion 110a with respect to the X axis. This angle, which both the first clamp portion 110a and the extension link 104 form with respect to the X axis, is designated X1.

The spreader arms 108a and 108b initially are held adjacent to each other with a lock, which may be a clamp 103 or other fastener. The clamp 103 includes a grommet 105 which is in contact with the second base plate 102b when the graft vessel preparation device 100 is in the locked position. When the clamp 103 releases the second base plate 102b, the spreader arms 108a and 108b separate from one another, as shown with reference to FIG. 10.

Figure 10:
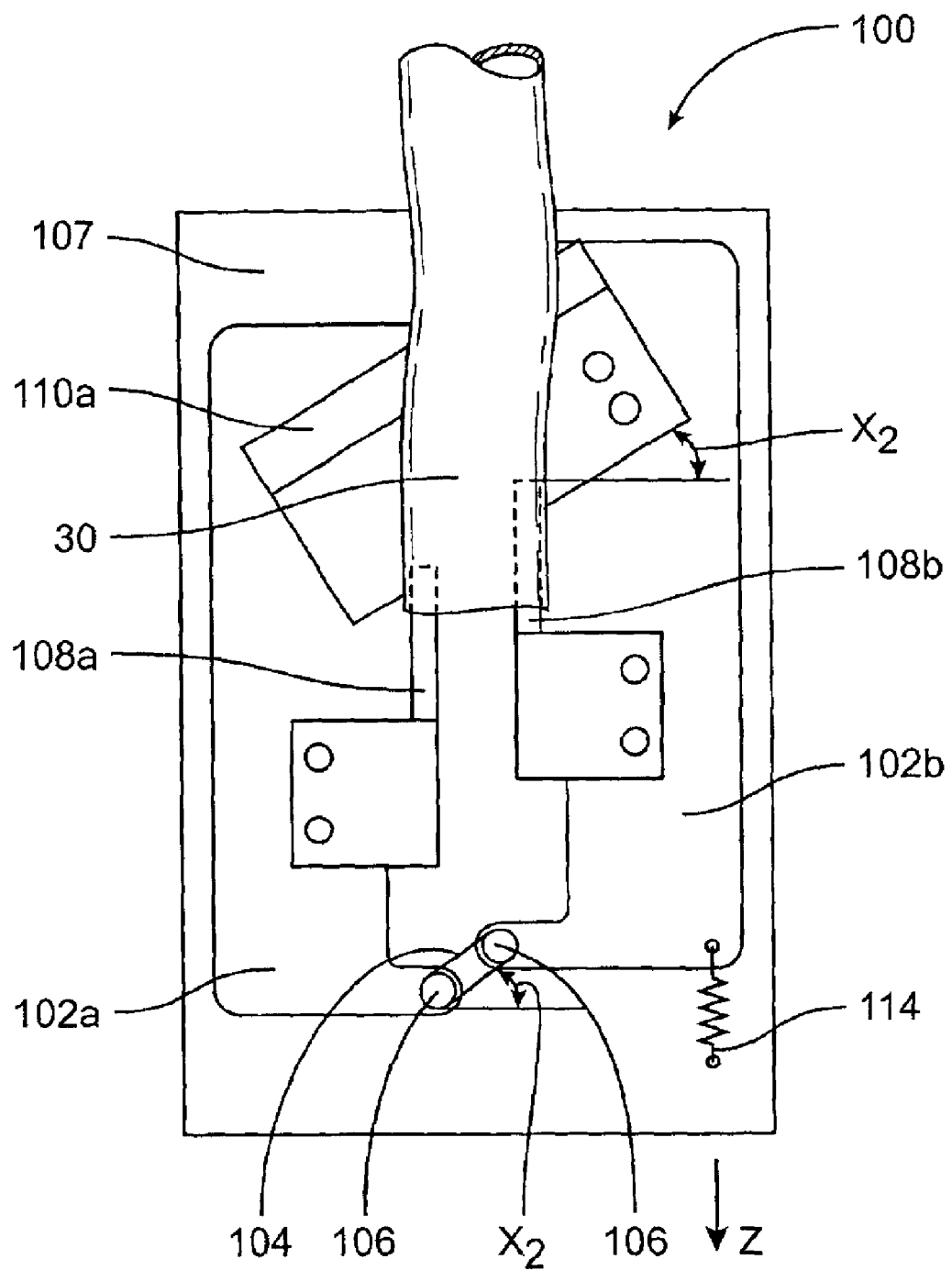
FIG. 10 is a top view of the graft vessel preparation device, wherein the spreader arms are separated by a tension spring.

In FIG. 10, the spreader arms 108a and 108b are shown separated by a spring 114. The spring 114 is attached to the second base plate 102b at one end and anchored at the opposite end to the base 107. When the lock is disengaged, the spring 114 pulls the second base plate 102b in a downward direction, thereby separating the spreader arms 108a and 108b from one other. The force generated by the spring 114 can be selected such that the spreader arms exert a force within the graft vessel 30 which is substantially equivalent to the force exerted on the graft vessel 114 by the normal blood pressure of the patient. This allows the graft vessel 30 to be stretched by the graft preparation device to a condition which mimics the condition of the pressurized graft. As the spreader arms 108a and 108b separate, the extension link 104 rotates to form an angle X2 with respect to the X axis. Once the spreader arms are separated within the graft vessel, the spreader arms may be pushed further into the interior of the graft vessel to fully support the end of the graft vessel.

Figure 11:
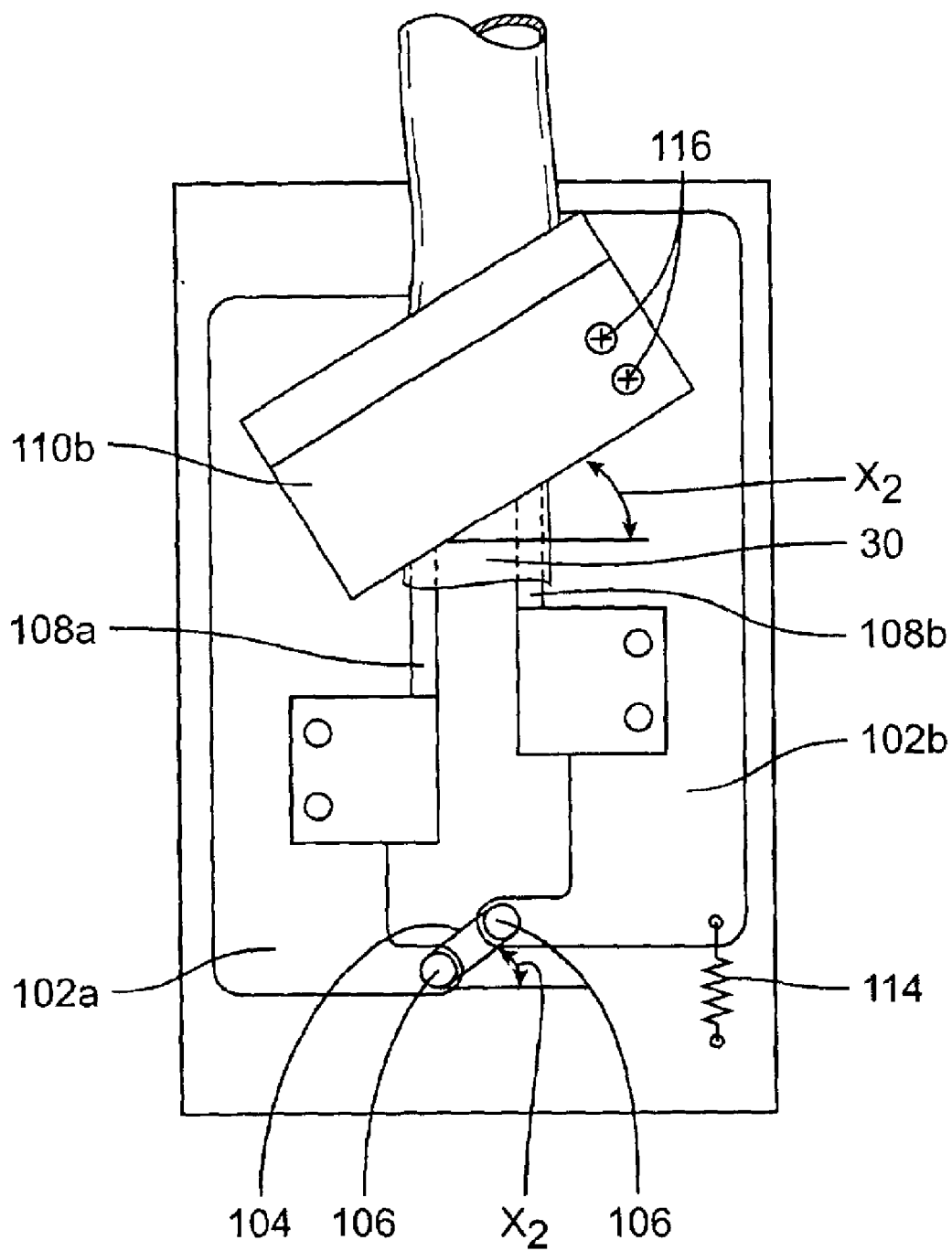
FIG. 11 is a top view of the graft vessel preparation device, showing a second clamp portion attached to a first clamp portion.

Referring also to FIG. 11, after the graft vessel is stretched 30 a desired amount, a second clamp portion 110b is attached to the first clamp portion 110a, to trap the graft vessel 30. The second clamp portion 111b is attached to the first clamp portion 110a using fasteners 116 such as threaded fasteners or the like. When the second clamp portion 110b is attached to the first clamp portion 110a, the angle X2 is maintained such that the second clamp portion 110b is substantially aligned with the extension link 104. The trapped graft vessel 30 is flattened sufficiently by the clamp 110 to hold the graft vessel 30 in place without damaging the graft vessel 30.

Figure 12:
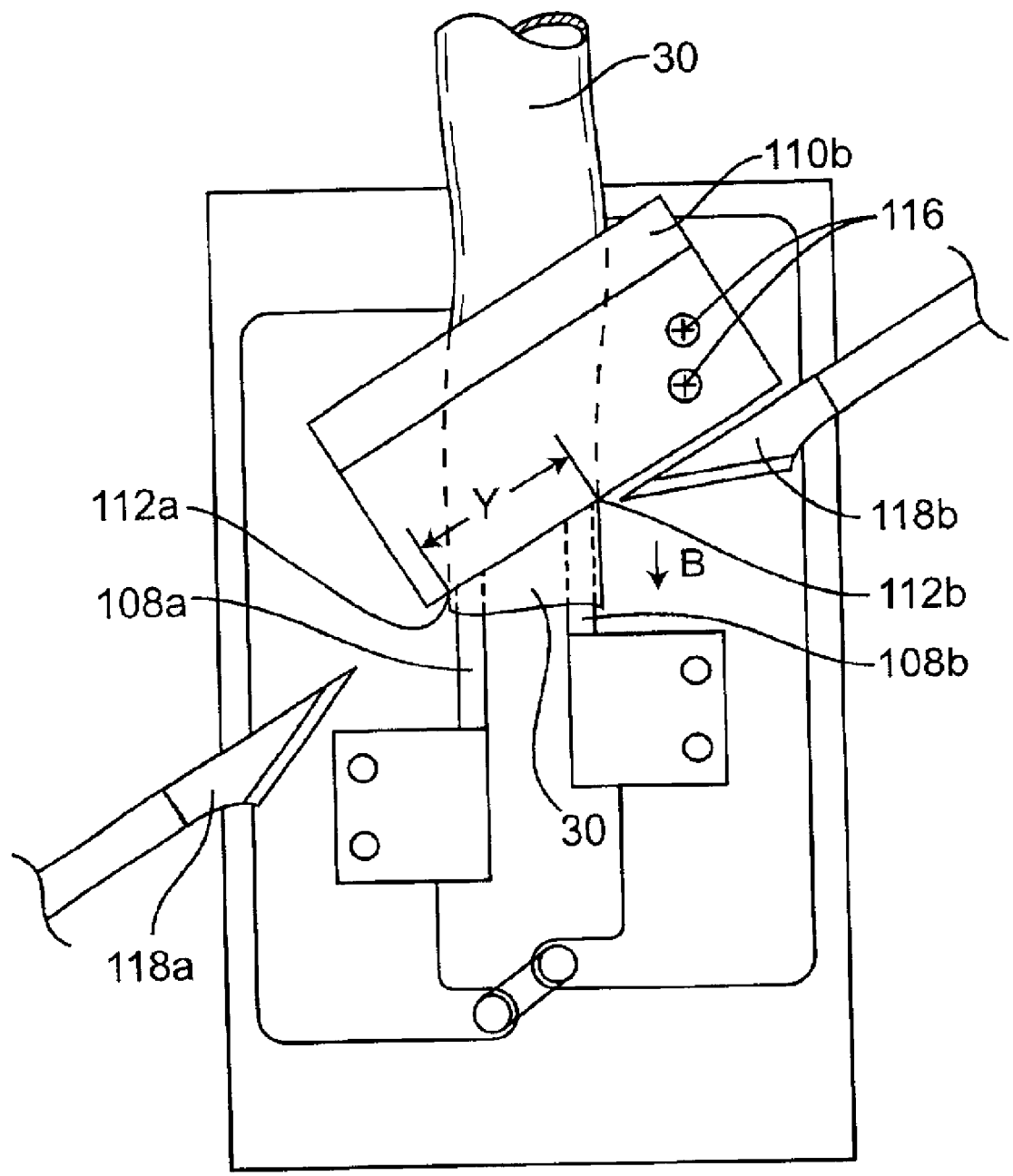
FIG. 12 is a top view of the graft vessel preparation device, showing incisors slicing or splitting the free end of the graft vessel.

FIG. 12 illustrates a method for slicing a graft vessel 30. As shown, the clamp 110 defines incision points 112a and 112b on the graft vessel where the graft vessel and the clamp intersect. The incision points define a critical dimension of the graft vessel. The clamped graft can be sliced or split using incisors 118a and 118b. The spreader arms can contain grooves on their outer or incisor contacting surfaces (not shown) which act as guides for the incisors as the incisors slice the graft vessel.

Figure 13:
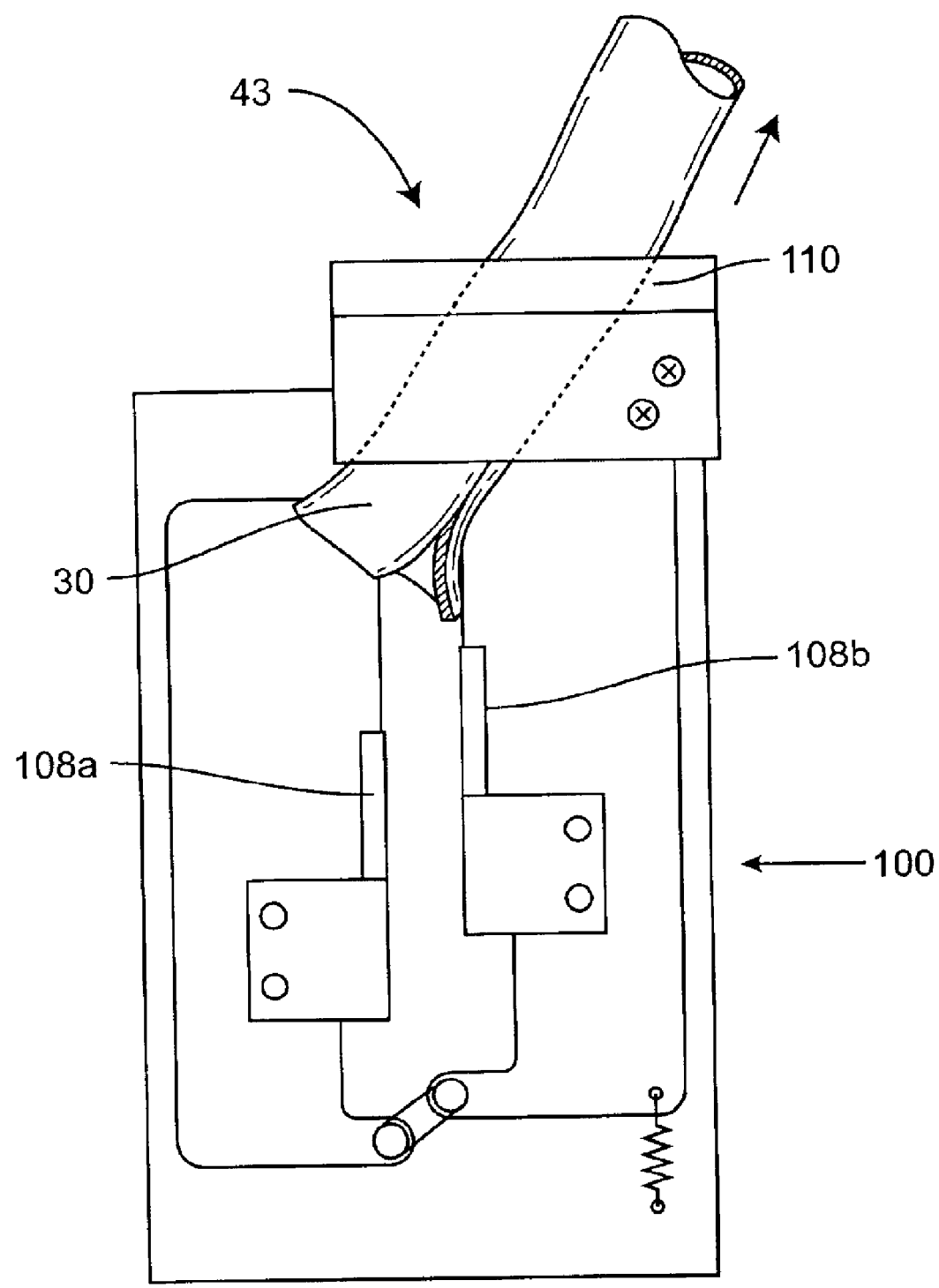
FIG. 13 is a top view of the graft vessel preparation device, showing the removal of the graft vessel/clamp assembly from the graft vessel preparation device.

FIG. 13 illustrates removal of the graft vessel/clamp assembly 43 from the graft vessel preparation device. The graft vessel/clamp assembly 43 is removed from the graft vessel preparation device 100 by disengaging the clamp 110 from the graft preparation device 100 and sliding the graft vessel/clamp assembly 43 off of the spreader arms 108a and 108b.

Figure 14:
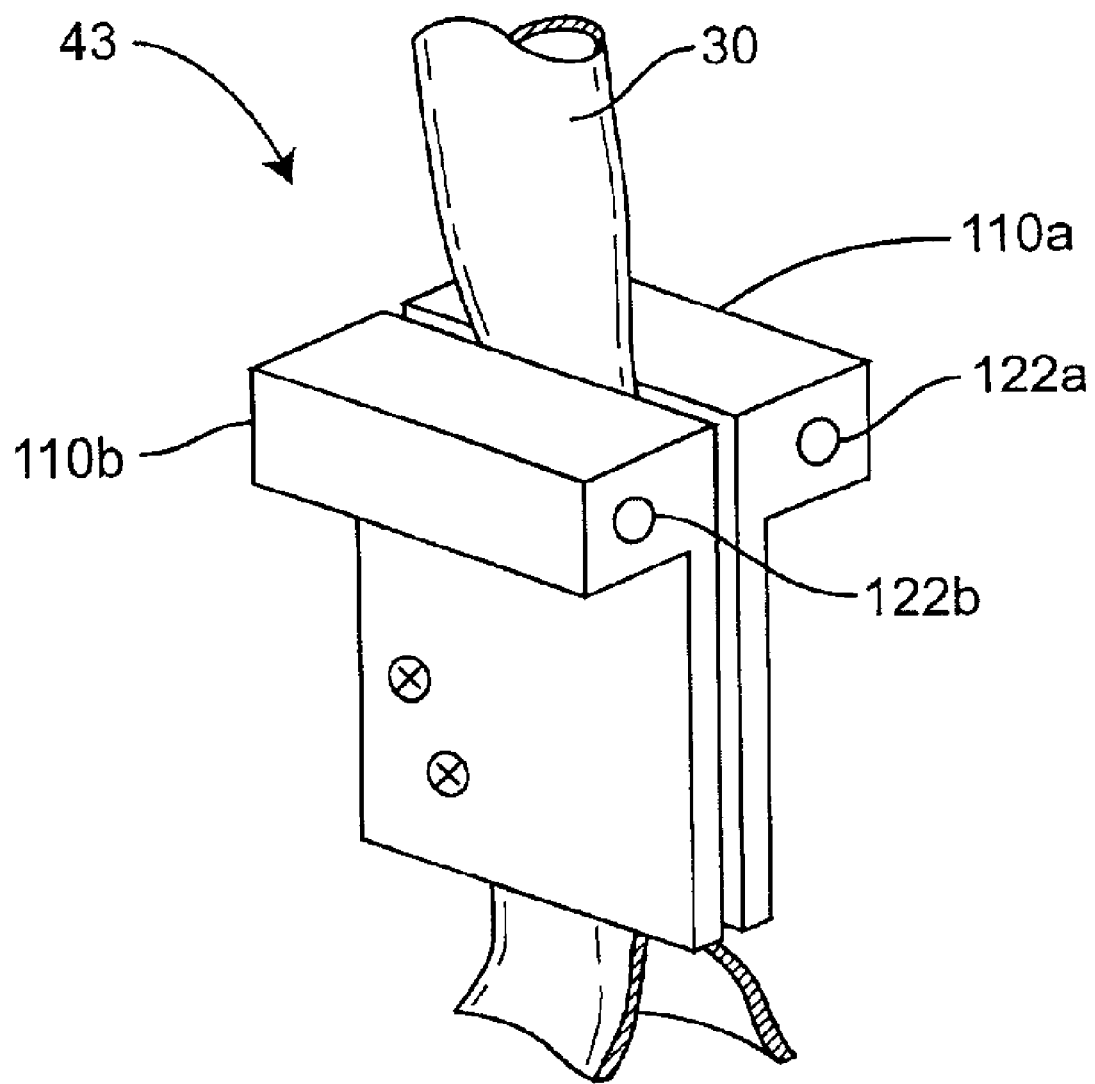
FIG. 14 is a perspective view of the graft vessel/clamp assembly.

FIG. 14 shows a perspective view of the graft vessel/ clamp assembly 43. The graft vessel 30 is shown secured between opposite halves of the clamp assembly 110a and 110b. Alignment holes 122a and 122b for mating with the distal anastomotic tool are also shown. The graft vessel/ clamp assembly 43 is now ready for attachment to a distal anastomotic tool in preparation for grafting.

The graft vessel preparation device 100 is only one embodiment of a device which can be used to establish a critical dimension and locate a graft vessel in a clamp. Other preparation devices may instead be used. As with the clamp disclosed above, the flapper clamp can also have alignment holes or other alignment means for attachment to a distal anastomosis deployment tool.

The proximal anastomosis procedure may be performed with an anastomosis device comprising a first linkage formed of a plurality of struts and a plurality of axial members. The first linkage is expandable from a first configuration in which the first linkage is a substantially cylindrical shape to a second configuration in which the first linkage includes a first radially extending flange. The device further comprises a substantially cylindrical central connecting portion extending from the first linkage and a second linkage configured to form a second radially extending flange spaced from the first radially extending flange. Various embodiments of this device and a deployment tool for performing the proximal anastomosis are shown in FIGS. 15–28.

Figure 15:
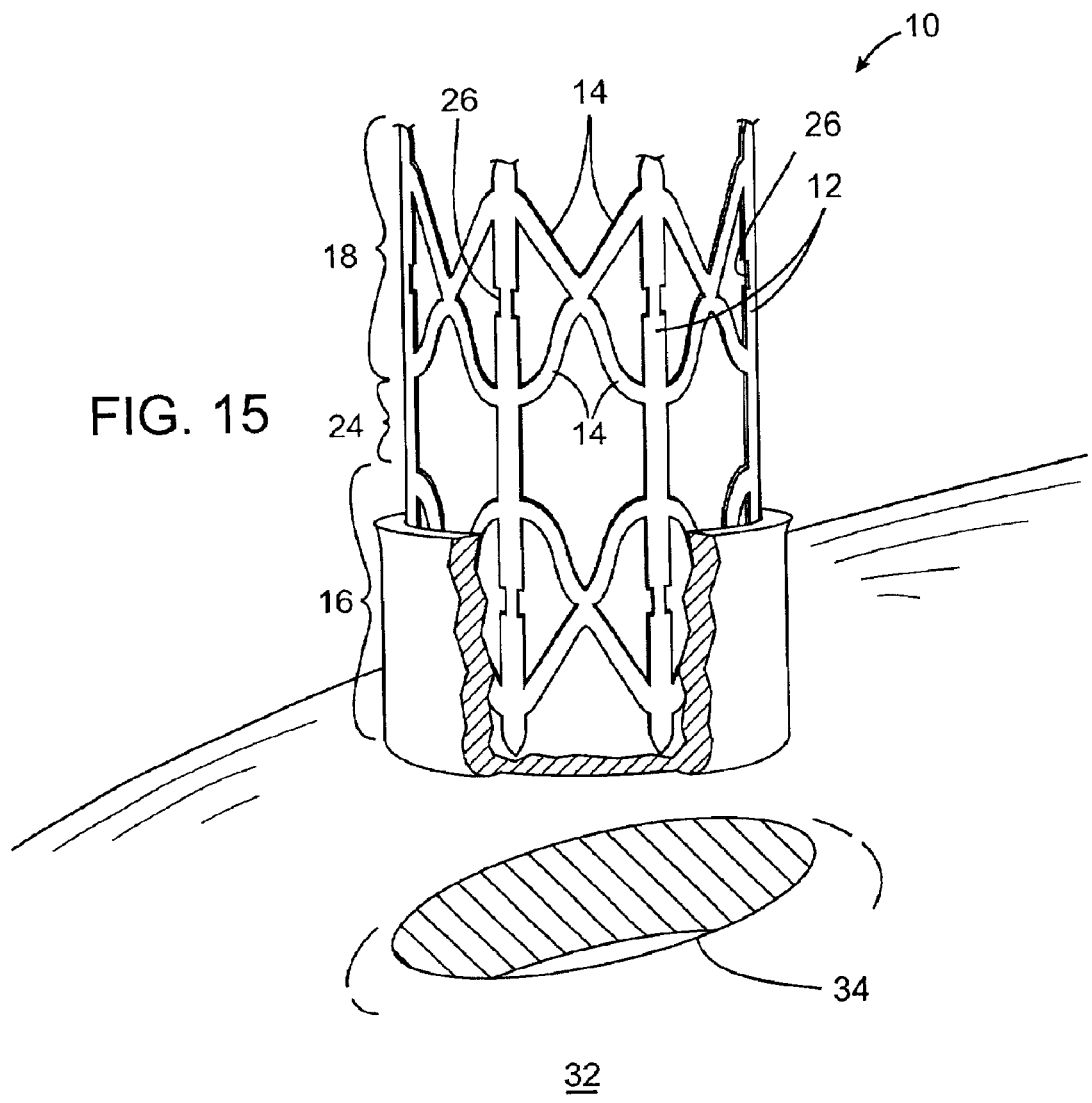
FIG. 15 is a perspective view of an anastomosis device in a configuration prior to use with a graft vessel everted over the device.
Figure 16:
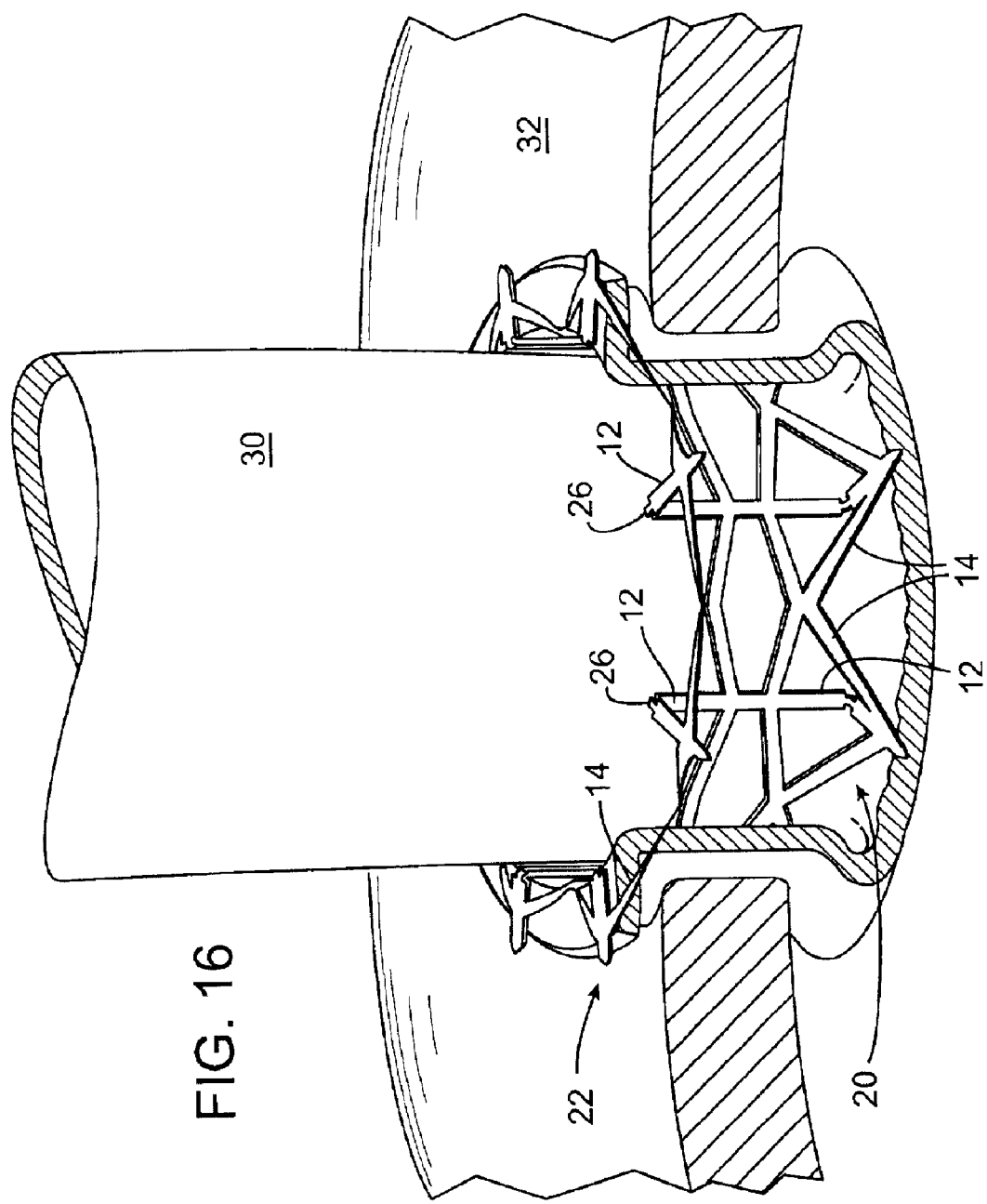
FIG. 16 is a perspective view of the anastomosis device of FIG. 15 in a deployed configuration.
Figure 17:
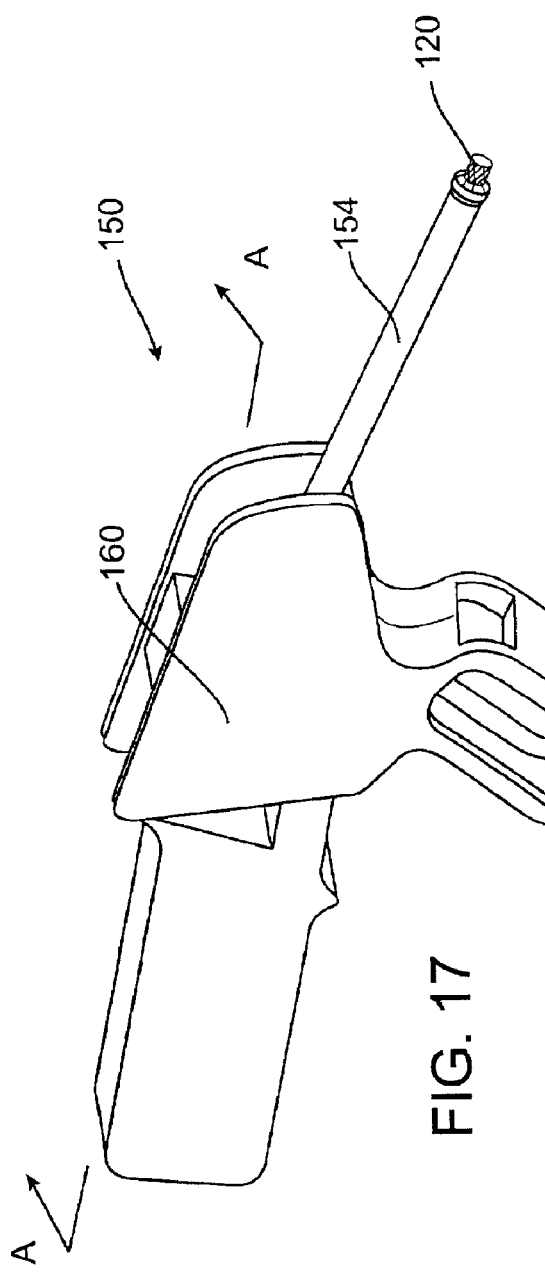
FIG. 17 is a perspective view of an anastomosis device deployment system.

FIG. 15 illustrates one embodiment of an anastomosis device 10. The anastomosis device 10 includes a plurality of axial members 12 and a plurality of struts 14 interconnecting the axial members. The axial members 12 and struts 14 form a first linkage 16 at a first end of the device and a second linkage 18 at a second end of the device. The first and second linkages 16, 18 are connected by a central connecting portion 24. Referring also to FIG. 16, the first and second linkages 16, 18 form inner and outer flanges 20, 22 when the anastomosis device 10 is deployed. The deployed flanges 20, 22 may be annular ring shaped or conical in shape. In use, a graft vessel 30 is inserted through a center of the tubular anastomosis device 10 and is everted over the first linkage 16 at the first end of the device. The first end of the device may puncture part way or all the way through the graft vessel wall to hold the graft vessel 30 on the device. An opening 34 is formed in the target vessel 32 to receive the graft vessel 30 and anastomosis device 10. Once the anastomosis device 10 with everted graft vessel 30 are inserted through the opening 34 in the target vessel 32, the inner and outer flanges 20, 22 are formed to secure the graft vessel to the target vessel by trapping the wall of the target vessel between the two flanges. The anastomosis device 10 forms a smooth transition between the target vessel 32 and the graft vessel 30 which helps to prevent thrombi formation.

The inner and outer flanges 20, 22 are formed by radial expansion of the anastomosis device 10 as follows. The first and second linkages 16, 18 are each made up of a plurality of axial members 12 and struts 14. The struts 14 are arranged in a plurality of diamond shapes with adjacent diamond shapes connected to each other to form a continuous ring of diamond shapes around the device. One axial member 12 extends through a center of each of the diamond shapes formed by the struts 14. A reduced thickness section 26 or hinge in each of the axial members 12 provides a location for concentration of bending of the axial members. When an expansion member of a deployment tool such as a rod or balloon is inserted into the tubular anastomosis device 10 and used to radially expand the device, each of the diamond shaped linkages of struts 14 are elongated in a circumferential direction causing a top and bottom of each of the diamond shapes to move closer together. As the top and bottom of the diamond shapes move closer together, the axial members 12 bend along the reduced thickness sections 26 folding the ends of the device outward to form the inner and outer flanges 20, 22 with the result that the wall of the target vessel 32 is trapped between the flanges and the everted graft vessel 30 is secured to the target vessel.

In the anastomosis device 10 shown in FIGS. 15–16, the struts 14 may be straight or curved members having constant or varying thicknesses. In addition, the axial members 12 may have the reduced thickness sections 26 positioned at a center of each of the diamond shapes or off center inside the diamond shapes. The positioning and size of the reduced thickness sections 26 will determine the location of the flanges 20, 22 and an angle the flanges make with an axis of the device when fully deployed. A final angle between the flanges 20, 22 and longitudinal axis of the device 10 is about 40–100 degrees, preferably about 50–90 degrees.

Figure 18:
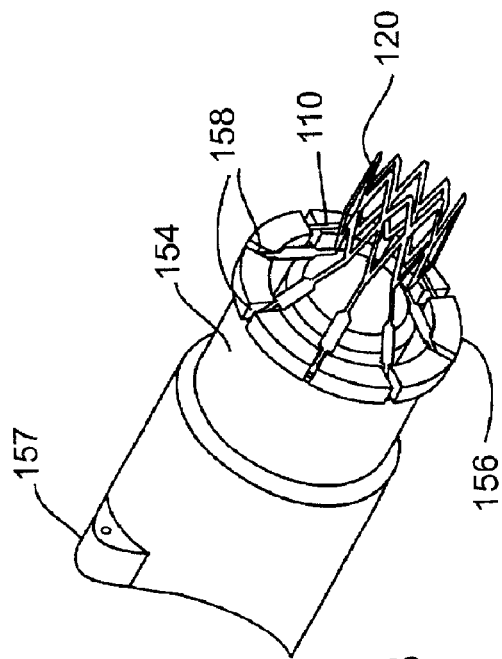
FIG. 18 is an enlarged perspective view of the distal end of the anastomosis device deployment system of FIG. 17 with an anastomosis device prior to deployment.

FIGS. 17–22 illustrate a deployment system 150 and sequence of deploying an anastomosis device 120 with the deployment system 150. In FIGS. 17–20 the graft vessel 30 has been eliminated for purposes of clarity. The deployment system 150 includes a hollow outer trocar 152 (not shown in FIGS. 17 and 18), a holder tube 154 positioned inside the trocar, and an expander tube 156 slidable inside the holder tube. Referring also to FIG. 18, the anastomosis device 120 is attached to a distal end of the holder tube 154 by inserting T-shaped ends of pull tabs 110 in slots 158 around the circumference of the holder tube. A camera 157 may be provided on the outer surface of the trocar 152, for monitoring the proximal anastomosis more clearly. A device handle 160 is provided for moving the tubes with respect to one another will be described in further detail below with respect to FIGS. 22–25.

Figure 19:
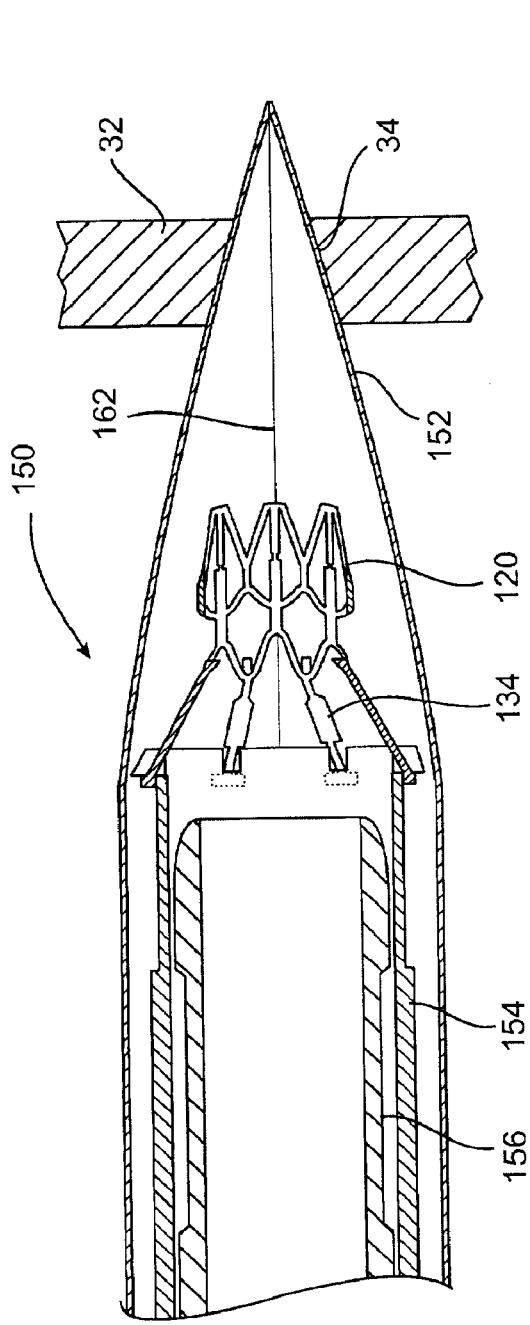
FIG. 19 is a side cross sectional view of the anastomosis device deployment system puncturing the target vessel to advance the anastomosis device into the target vessel wall.
Figure 20:
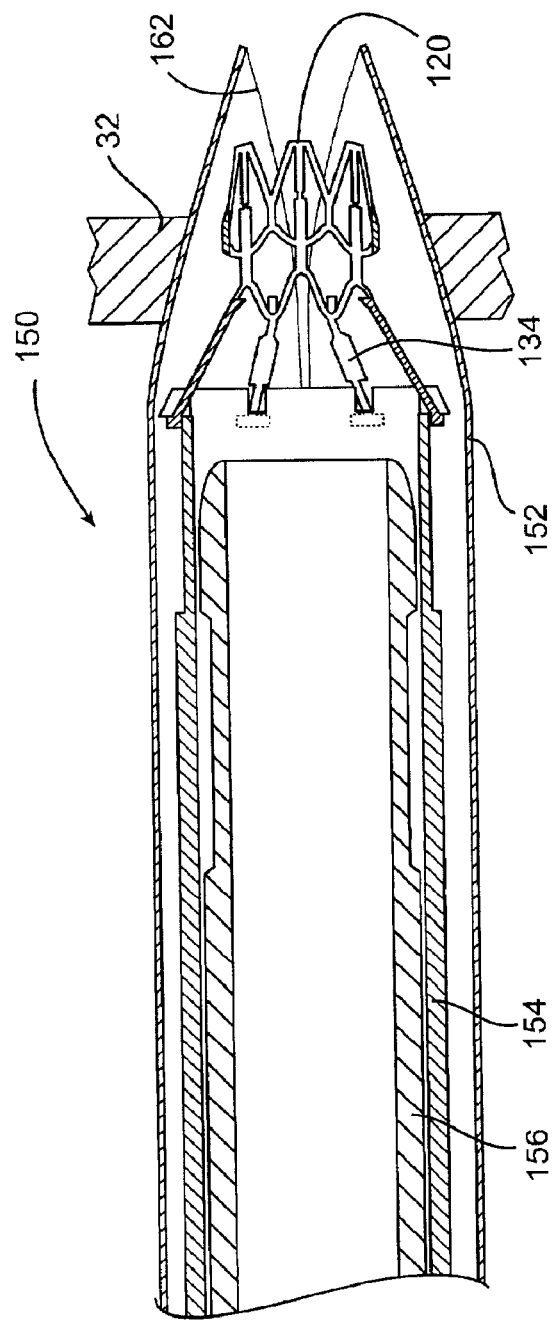
FIG. 20 is a side cross sectional view of the anastomosis device deployment system advancing the anastomosis device into the target vessel wall.

As shown in FIG. 19, initially, the holder tube 154, expander tube 156, and the anastomosis device 120 are positioned within the trocar 152 for insertion. The trocar 152, holder tube 154, and expander tube 156 are all slidable with respect to one another during operation of the device. The trocar 152 has a hollow generally conical tip with a plurality of axial slots 162 which allow the conical tip to be spread apart so that the anastomosis device 120 can slide through the opened trocar. The trocar 152, acting as a tissue retractor and guide, is inserted through the wall of the target vessel 32 forming an opening 34. As shown in FIG. 20 the anastomosis device 120 is then advanced into or through the target vessel wall 32 with the holder tube 154. The advancing of the holder tube 154 causes the distal end of the trocar 152 to be forced to spread apart. Once the anastomosis device 120 is in position and the trocar 152 has been withdrawn, the inner annular flange 20 is deployed by advancing the expander tube 156 into the anastomosis device. The advancing of the expander tube 156 increases the diameter of the anastomosis device 120 causing the inner flange to fold outward from the device. This expanding of the inner flange may be performed inside the vessel and then the device 120 may be drawn back until the inner flange abuts an interior of the target vessel wall 32.

As shown in FIG. 22, after the inner flange has been deployed, the holder tube 154 is advanced forming the outer flange. As the holder tube 154 is advanced, the anastomosis device 120 butts against a circumferential groove 157 on an exterior of the expander tube 156 which holds the anastomosis device stationary on the expander tube 156. The holder tube 154 is then moved forward to detach the entire anastomosis device by disengaging the pull tabs 130 from the slots 158 in the holder tube and causing the outer flange to be deployed. During deployment of the outer flange, shoulders 134 on the device engage a tapered distal end of the holder tube 154 causing the pull tabs 130 to be released from the slots 158. Alternatively, and as will be explained in connection with a frangible anastomosis device according to the invention, movement of the holder tube 154 can detach a deployed portion of the device from a discard portion of the device which remains attached to the holder tube.

One alternative embodiment of the holder tube 154 employs a plurality of flexible fingers which receive the pull tabs 130 of the anastomosis device 120. According to this embodiment each pull tab 130 is received by an independent finger of the holder tube 154. To deploy the second or outer flange of the anastomosis device 120, the flexible fingers flex outward bending the pull tabs 130 outward. For instance, the flexible fingers can be designed to flex when the pull tabs and fingers are put under axial compression in which case the fingers and tabs buckle outwards together to deploy the outer flange and release the anastomosis device from the holder tube.

FIGS. 23–26 illustrate the operation of one embodiment of the handle 160 to move the trocar 152, the holder tube 154, and the expander tube 156 with respect to one another to deploy the anastomosis device 120. The handle 160 includes a grip 170 and a trigger 172 pivotally mounted to the grip at a pivot 174. The trigger 172 includes a finger loop 176 and three contoured cam slots 178, 180, 182 corresponding to the trocar 152, holder tube 154, and expander tube 156, respectively. Each of these tubes has a fitting 184 at a distal end thereof. A pin 186 connected to each of the fittings 184 slides in a corresponding one of the cam slots 178, 180, 182. A fourth cam slot and tube may be added to control deployment of the outer flange 22. Alternatively, the handle 160 can be modified to include fewer cam slots for deployment of the inner and outer flanges 20, 22.

Figure 23:
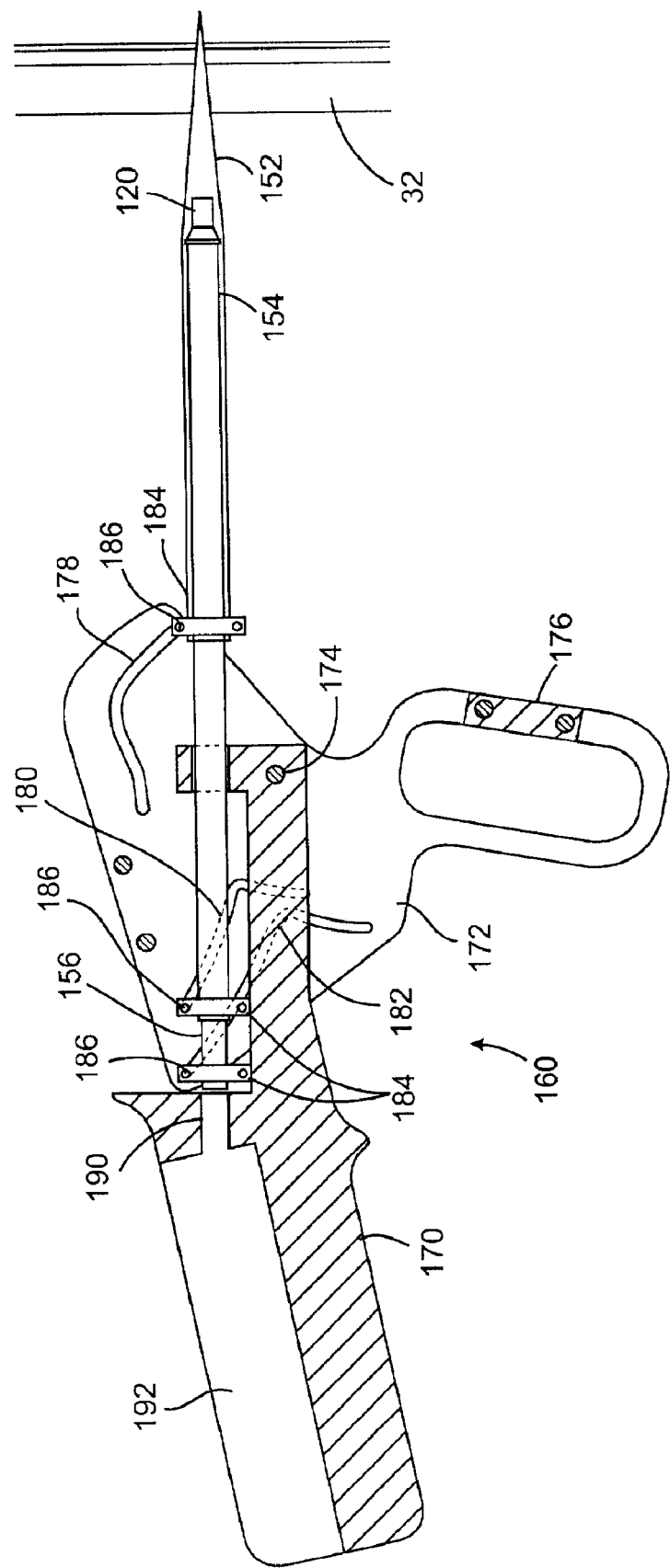
FIG. 23 is a schematic side cross-sectional view of a deployment tool taken along line A—A of FIG. 17, where the deployment tool is shown during a vessel puncturing step.

The handle 160 is shown in FIG. 23 in an insertion position in which the trocar 152 extends beyond the holder tube 154 and the expander tube 156 for puncturing of the target vessel wall 32. Optionally, a flexible seal (not shown) such as heat shrinkable plastic or elastomeric tubing can be provided on the outer surface of the trocar 152 such that the seal covers the axial slots 162 at a location spaced from the tip of the trocar to prevent leaking of blood from the target vessel after the incision is formed. In one embodiment, the trocar 152 is actuated by a mechanism which causes the trocar 152 to penetrate the aorta wall 32 at a high rate of speed to minimize deformation of the aorta and maintain a fluid tight seal at the puncture site in a manner similar to biopsy gun. For instance, the spring mechanism attached to the trocar 152 and/or the handle 160 can be used to fire the trocar 152 at the incision site. Any suitable actuating mechanism can be used to fire the trocar 152 in accordance with the invention. As the trigger 172 is rotated from the position illustrated in FIG. 23 to the successive positions illustrated in FIGS. 24–26, the pins 186 slide in the cam slots 178, 180, 182 to move the trocar 152, holder tube 154 and expander tube 156.

FIG. 24 shows the handle 160 with the trigger 172 rotated approximately 30 degrees from the position of FIG. 23. This rotation moves the holder tube 154 and expander tube '156 forward into the wall of the target vessel 32 spreading the trocar 152. The anastomosis device 120 is now in position for deployment. FIG. 25 shows the trigger 172 rotated approximately 45 degrees with respect to the position of FIG. 23 and the cam slot 182 has caused the expander tube 156 to be advanced within the holder tube 154 to deploy the inner flange. The trocar 152 has also been withdrawn.

Figure 26:
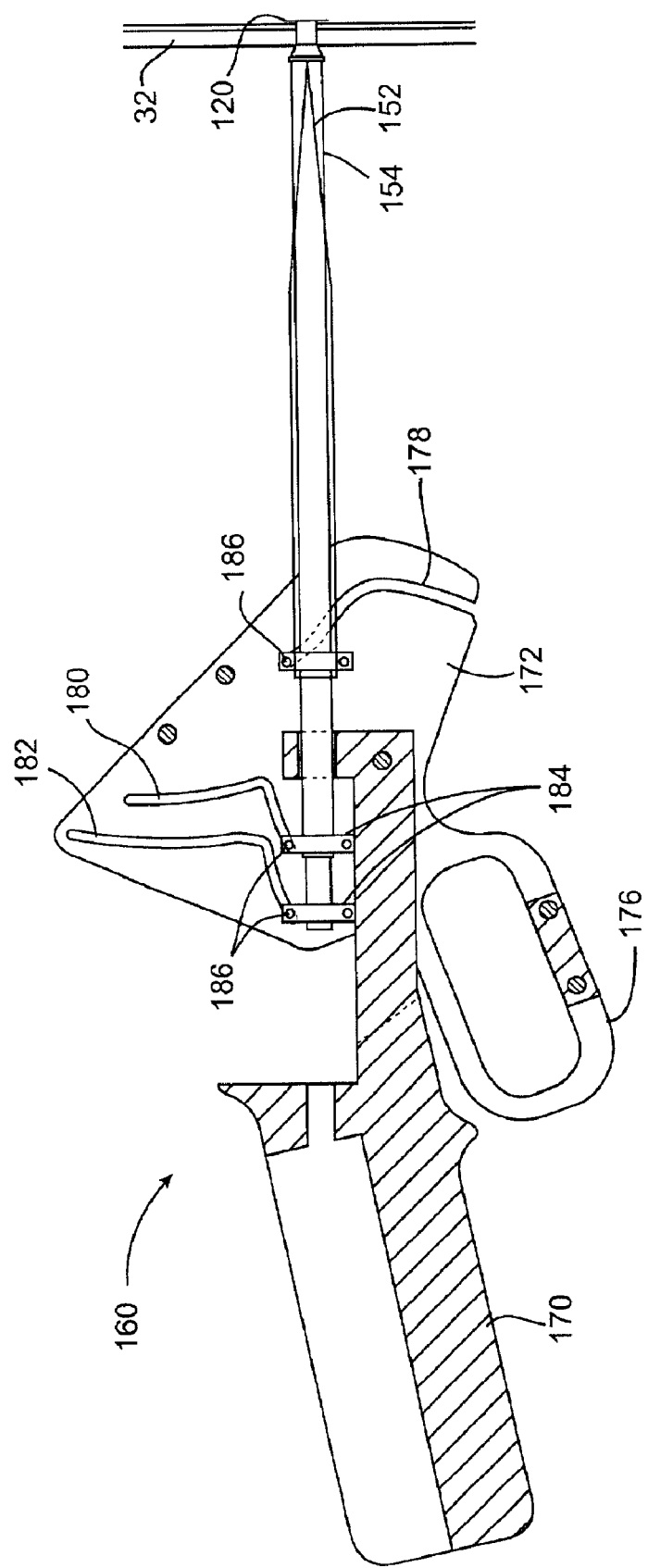
FIG. 26 is a schematic side cross-sectional view of the deployment tool shown after the anastomosis device has been fully deployed.

FIG. 26 shows the handle 160 with the trigger 172 pivoted approximately 60 degrees with respect to the position shown in FIG. 23. As shown in FIG. 26, the expander tube 156 has been partially retracted to pull the inner flange 20 against the vessel wall 32 and the holder tube 154 is moved forward to deploy the outer flange 22 and disengage the holder tube 154 from the anastomosis device 120.

The handle 160 also includes a first channel 188 and a second channel 190 in the grip 170 through which the graft vessel (not shown) may be guided. The grip 170 also includes a cavity 192 for protecting an opposite end of the graft vessel from the attachment end. Once the anastomosis is completed, the anastomosis device deployment system 150 is removed from the graft vessel.

Figure 27:
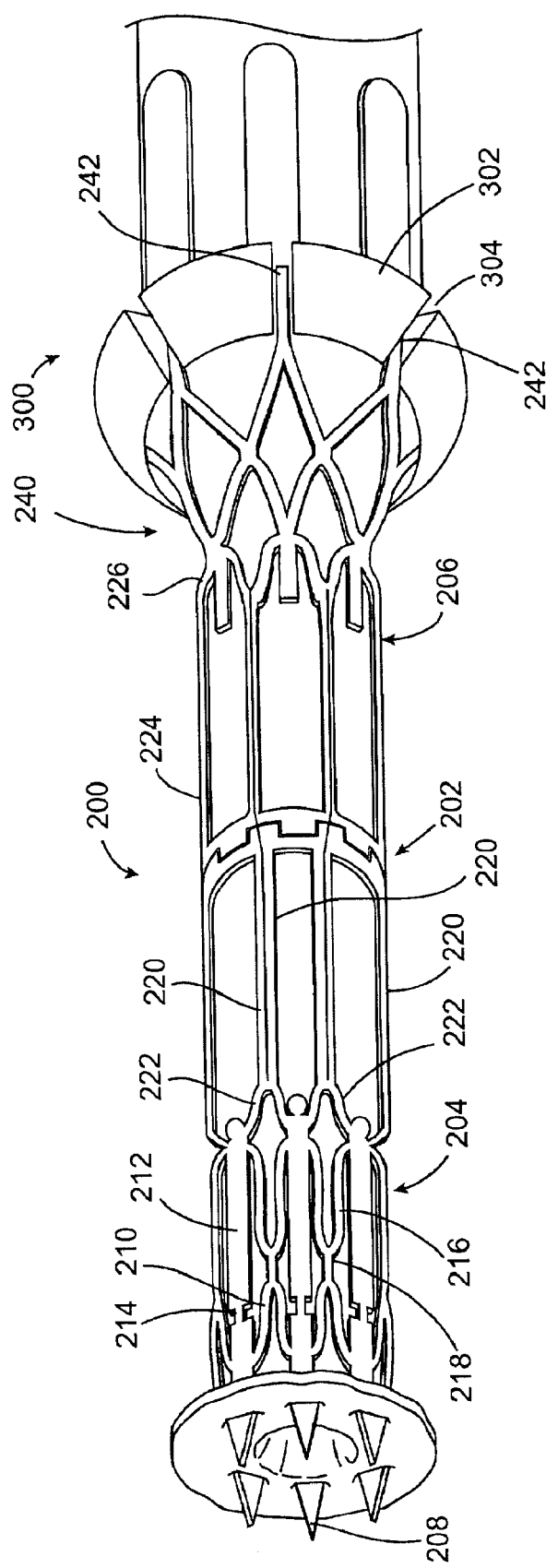
FIG. 27 is a perspective view of a frangible anastomosis device in a configuration prior to use.
Figure 28:
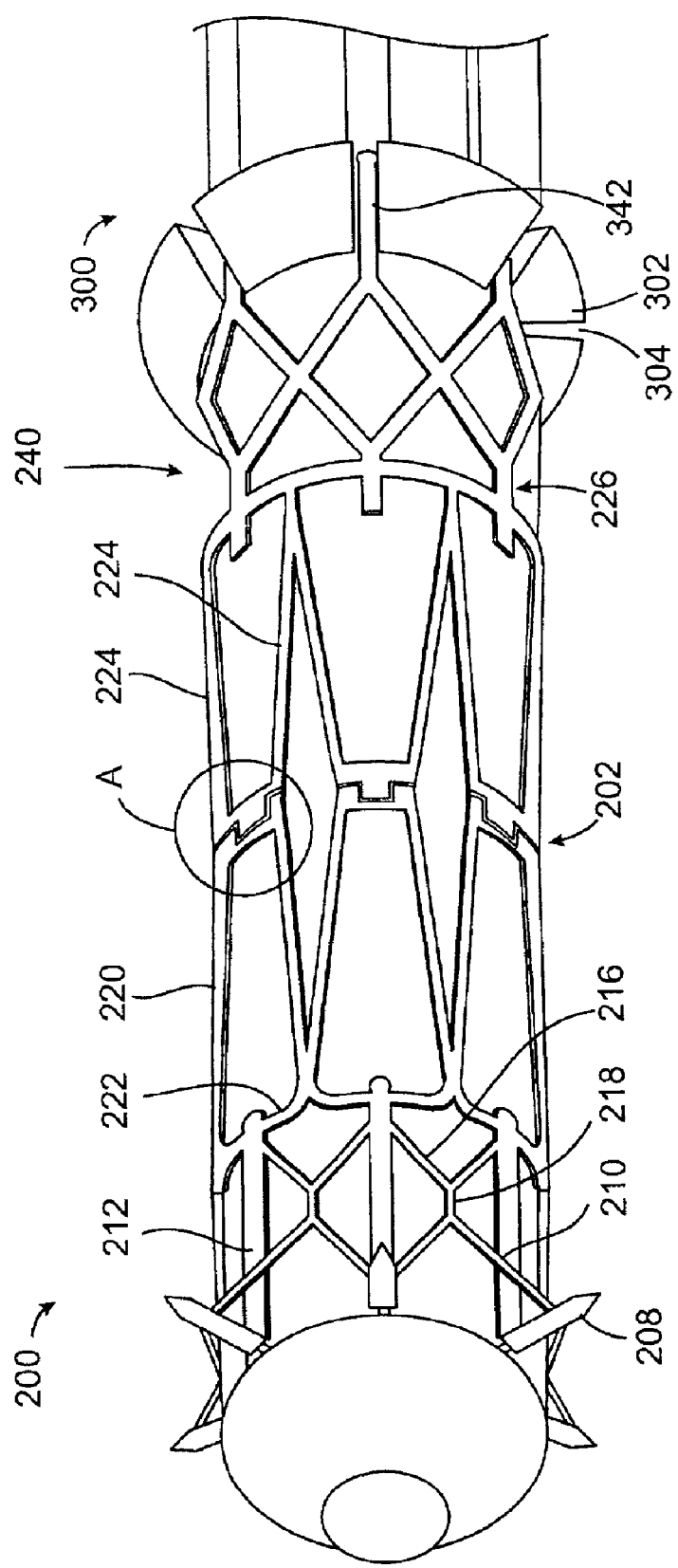
FIG. 28 is a perspective view of the device shown in FIG. 27 after radial expansion thereof.

Referring to FIGS. 27–28, in another embodiment, a device 200 includes a frangible linkage 202 which allows an anastomosis device 204 to separate from the remainder of the device 200 upon formation of the outer flange 22. The frangible linkage 202 connects the anastomosis device 204 to a discard portion 206. In one embodiment of a linkage design, the frangible linkage 202 is radially expanded and axially compressed to fracture the frangible linkage 202. The inner flange 20 is formed during radial expansion of the device 200 and the anastomosis device 204 can be severed while forming the outer flange 22. The device 200 cooperates with the deployment tool 300 for delivering and deploying the anastomosis device 204 at a site in a living body. As explained below, after the device 200 is positioned at a desired location, the anastomosis device 204 can be expanded to deploy an inner flange 20 and subsequently axially compressed to deploy an outer flange 22 while severing the anastomosis device 204 from the discard portion 206. The deployment tool 300 can then be withdrawn along with the discard portion 206 which remains attached to the distal end of the deployment tool 300.

FIG. 28 shows the device 200 in the radially expanded condition but prior to being axially compressed. During radial expansion of the device, axially extending barbs 208 (FIG. 27) are pivoted outwardly by struts 210 such that the outwardly extending barbs 208 and struts 210 form the inner flange. To facilitate bending of the barbs, the barbs 208 comprise points on the ends of axially extending members 212 which have narrow sections 214 located a desired distance from the free ends of the barbs 208. For instance, the narrow sections 214 can be located at axial positions along the device corresponding approximately to the axial midpoint of the struts 210 connecting adjacent members 212 when the device is in the pre-expanded condition shown in FIG. 27.

To facilitate easier bending of the struts 210 during radial expansion of the device, the distal ends of the struts can be curved at their points of attachment to the members 212. Likewise, a curved bend can be provided at the intersection where the proximal ends of the struts are attached together. When the device is radially expanded, the members 212 move radially outward and circumferentially apart as the struts 210 move radially outward until a force on the barbs 208 by the struts 210 causes the struts to become bent at the narrow sections 214, after which the barbs extend outwardly to form the inner flange. In this deployed condition, the struts 210, 216 provide out-of-plane stiffness for the barbs 208 due to their triangulated final configuration. The struts 216 are similar in configuration to the struts 210 with respect to how they are shaped and attached to the members 212. Short axially extending members 218 connect the intersection of the struts 210 to the intersection of the struts 216.

The frangible section 202 is located at the proximal ends of axially extending members 220 which are connected to the members 212 by U-shaped links 222. The members 220 are arranged in pairs which are attached together at only their distal ends. In particular, the distal ends of the links 222 are attached to proximal ends of the members 212 and the midpoint of each link 222 is attached to the distal ends of a respective pair of members 220. As shown in FIG. 28, during radial expansion of the device, the individual links 222 are plastically deformed from their U-shaped configuration to form segments of a circumferentially extending annular ring. As a result, the device becomes shorter in the axial direction as links 222 form the annular ring and the distal ends of the members 220 move radially outward but not apart in the circumferential direction. At the same time, the proximal ends of the members 220 move radially outward and circumferentially apart.

After deployment of the proximal anastomotic device into the target vessel, the integrity of the device 200 is verified via direct observation through an endoscope. A standard bulldog clamp or other similar device is then placed on the graft vessel, using an endoscopic forceps or other appropriate tool. The bulldog clamp is placed on the graft vessel near the proximal end, to prevent blood loss through the graft vessel. Alternately, the bulldog clamp may be placed on the graft vessel before the proximal anastomosis is performed.

In the method set forth above, the proximal anastomosis is performed before the graft vessel clamp 43 is attached to the distal end of the graft vessel. Depending on the length of the graft vessel, attachment of the clamp 43 to the distal end of the graft vessel may be done inside or outside the chest cavity after the proximal anastomosis tool has been removed from the graft.

Figure 29:
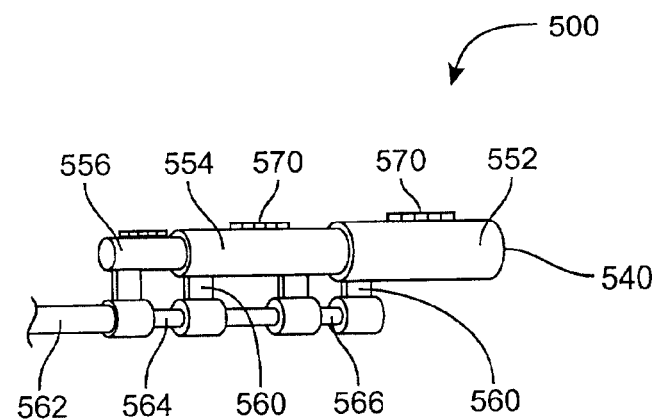
FIG. 29 is a perspective view of a splittable anastomosis tool.
Figure 30:
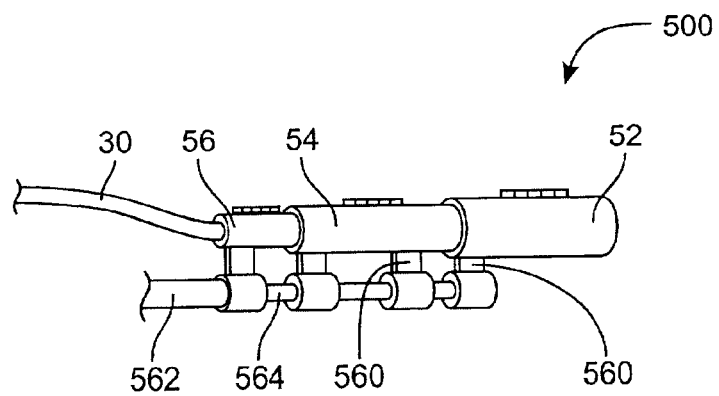
FIG. 30 is a perspective view of the splittable anastomosis tool with a graft vessel positioned in the tool.
Figure 31:
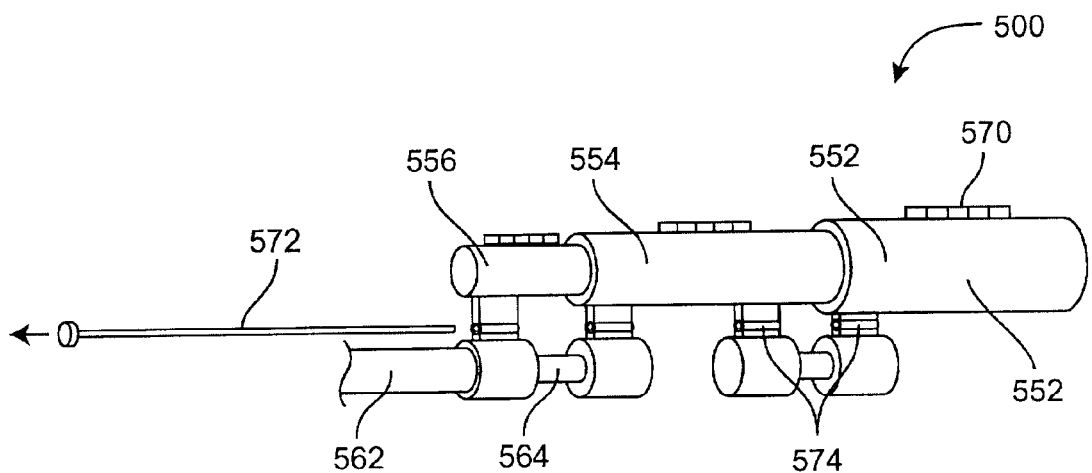
FIG. 31 is a perspective view of the splittable anastomosis tool showing a pin removed from the tool.

Referring to FIGS. 29–31, a proximal anastomosis device is deployed using a splittable proximal anastomosis tool 500. As used in this document, the term "splittable" refers to a tool that releases a graft vessel without requiring the graft vessel to be pulled through the tool. As one example, the splittable proximal anastomosis tool 500 may be configured to split into two or more separate pieces to allow removal of the tool 500 from the graft vessel after the proximal anastomosis has been performed. As another example, the splittable proximal anastomosis tool 500 may be configured to open at its distal end, rather than split into two separate pieces, to release the graft vessel. In use, the end of the anastomosis deployment tool with the graft vessel attached thereto is inserted into an incision in the chest cavity such that the proximal end of the graft vessel is positioned at the proximal anastomosis site. The anastomosis device can then be deployed. Afterwards, the splittable proximal anastomosis tool 500 can be opened to allow its removal from the graft vessel. By using a splittable proximal anastomosis tool 500, the end of the graft vessel destined for the distal anastomotic site can be prepared for connection to the target vessel before the proximal anastomosis is performed. For example, a distal clamp and/or cartridge can be connected to the end of the graft vessel destined for the distal anastomotic site before the proximal anastomosis is performed, thus allowing the surgeon to prepare both ends of the graft vessel for anastomosis before inserting the graft vessel into the thoracic cavity. The distal clamp and/or cartridge holding the distal end of the graft vessel may be too large to fit through the interior of the proximal tool 500, so by splitting the tool 500 into two or more pieces, the distal clamp and/or cartridge can be attached before proximal anastomosis and easily released by the tool 500. In this way, the end of the graft vessel destined for the distal anastomotic site need not be pulled back out of the thoracic cavity after the proximal anastomosis is performed. Further, the splittable proximal anastomosis tool 500 also allows the distal anastomosis to be performed before the proximal anastomosis.

A crown 540 is provided at the distal end of the splittable tool 500, where the crown 540 includes a shortened outer trocar tube 552, a shortened holder tube 554, and a shortened expander tube 556. The tubes 552, 554, 556 are coaxially arranged and operate in the manner described above with respect to the proximal anastomosis tool of FIGS. 17–25. For clarity, the proximal ends of the tubes are not shown. Each of the tubes 552, 554, 556 are connected by connecting elements 560 to associated actuation tubes 562, 564, 566. The actuation tubes 562, 564, 566 are used to move the trocar, holder, and expander tubes 552, 554, 556 with respect to one another. Alternately, the actuation tubes 562, 564, 566 are not used, and the trocar, holder and expander tubes 552, 554, 556 themselves transmit axial forces. In such an embodiment, the trocar tube 552 need not be split, because it can be retracted relative to the holder and expander tubes 554, 556 during release of the graft vessel.

As shown in FIG. 30, the graft vessel 30 extends through the center of the trocar, holder, and expander tubes 552, 554, 556. The tubes 552, 554, 556 are all splittable tubes that can be split or opened longitudinally along hinges 570 to remove the graft vessel 30. Referring to FIG. 31, a pin 572 is removed from a plurality of channels 574 in the connecting elements 560 to allow the tubes 552, 554, 556 to open at the hinges 570 for removal of the graft vessel 30. The combination of the pin 572 and channels 574 is only one example of a type of splitting mechanism which can be used.

Figure 32A:
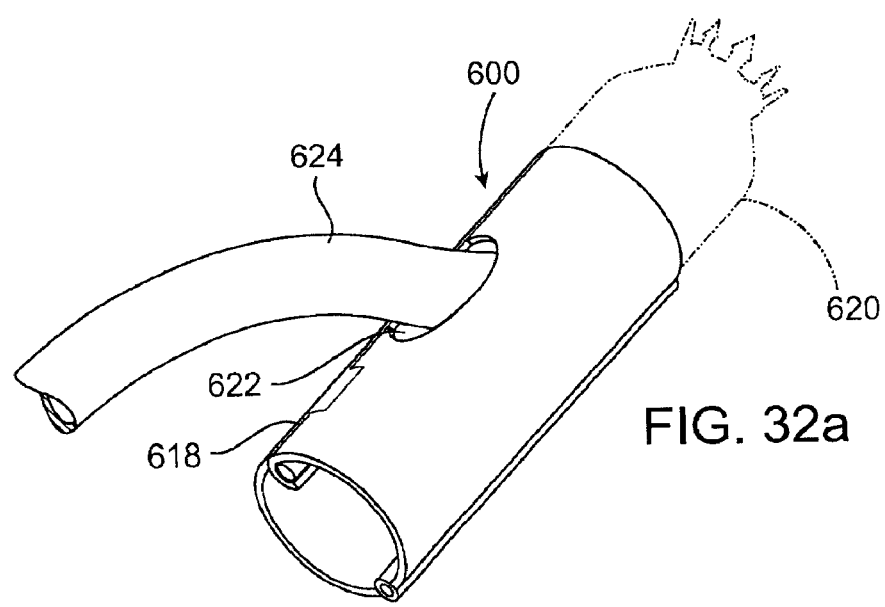
FIG. 32a is a perspective view of the end effector of another embodiment of a splittable anastomosis tool
Figure 32B:
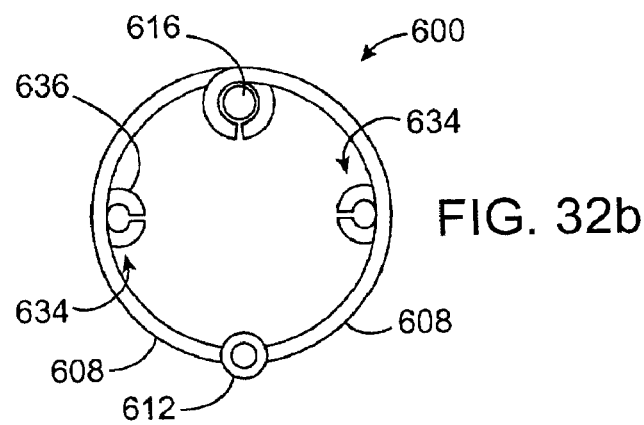
FIG. 32b is a cross-section view of the end effector of FIG. 32a in a closed position.
Figure 32C:
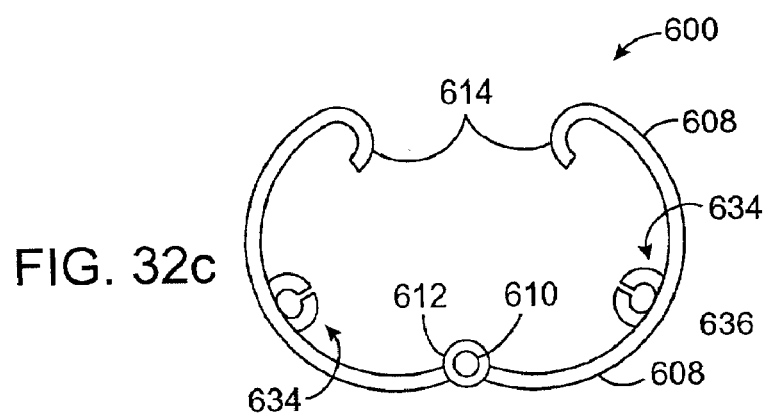
FIG. 32c is a cross-section view of the end effector of FIG. 32a in an open position.

Referring to FIGS. 32a–c, another embodiment of a proximal anastomosis tool 500 is shown. This tool 500 includes a end effector 600 connected to a shaft 602. As shown, the end effector 600 is articulated relative to the shaft 602 via a tower 606 and socket 866 arrangement, as is described in greater detail below. However, the end effector 600 may be fixed to the shaft 602. Further, the end effector 600 and shaft 602 may be articulated in a different manner, as described below. Further, the end effector 660 may be integral with the shaft 602. If so, the term "end effector" refers to the distal end of the shaft 602.

The end effector 600 includes a crown tube 607 that is split into two crown segments 608, movably connected to one another via a first pin 610 extending through hinge elements 612 defined through both crown segments 608. The hinge elements 612 are cylindrical elements extending along at least part of an edge of each crown segment 608. Alternately, the hinge elements 612 take another shape that allows for rotary motion of those hinge elements 612 about the first pin 610. Further, the hinge elements 612 may be positioned on each crown segment 608 at a location other than an edge. The two crown segments 608 form a hinge rotating around the axis defined by the first pin 610. The two crown segments 608 may be connected in a different manner, if desired.

The two crown segments 608 each have a substantially semicircular cross-section that extends substantially linearly along at least a portion of the length of the end effector 600, each cross-section having substantially the same radius of curvature. The radius of curvature of the crown segments 608 may vary along their length. Alternately, each crown segment 608 may have a substantially semicircular cross-section that has a different radius of curvature. Alternately, the radius of curvature of the cross section of each crown segment 608 may vary along at least a portion of the length of the crown 607, where the variation may be the same or different along each crown segment 608. Alternately, the cross-section of each crown segment 608 may be another curved shape, such as a segment of an ellipse, or a more complex curve. Alternately, the shape of the cross-section of each crown segment 608 may vary along the length of the crown 607.

One of the crown segments 608 extends behind the other, having a rear portion 618 that has a substantially circular cross-section with a radius of curvature substantially the same as that of the substantially semicircular portions of the crown segments 608. The rear portion 618 may have a different cross-section, if desired. Alternately, neither of the crown segments 608 extends behind the other. Alternately, the radius of curvature of the rear portion 618 of a crown segment is different the radius of curvature of the semicircular portions of the crown segments 608.

Locking elements 614 are provided on each crown segment 608. Where the hinge elements 612 are positioned on a mating edge of each crown segment 608, the locking elements 614 are positioned on the opposite mating edge. A second pin 616 extends through the locking elements 614. Insertion of the second pin 616 into the locking elements 614 locks the crown 607 closed, and removal of the second pin 616 from the locking elements 614 allows the crown 607 to split, as shown most clearly in FIG. 32c. The crown segments 608 may be preloaded and/or compliant, in order to spring open upon removal of the second pin 616 from the locking elements 614. However, the crown segments 608 need not be preloaded or compliant. If they are not, then motion of the expander 626 (shown in FIG. 33) or other component of the tool separates the freed crown segments 608 from one another an appropriate amount. The second pin 616 is connected to the expander 626. Thus, the motion of the expander 626 removes the second pin 616 from the locking elements 614 when the expander 626 has reached the appropriate position. Further, the second pin 616 is retained safely on the expander 626 such that it does not become lost within the thoracic cavity of the patient after it is removed from the locking elements 614. The expander 626 is splittable as well. Alternately, the second pin 616 is connected to a wire or other element (not shown) extending out of the patient along the tool 500, and is thereby retracted by pulling that wire or other element. In this way, the second pin 616 is retained by the tool 500 or the surgeon. Other structures or mechanisms may be used to remove and retain the second pin 616.

An anastomosis device 620 is connected to the distal end of the end effector 600. For clarity in illustrating the end effector 600, the anastomosis device is shown schematically in FIG. 32a. Referring also to FIG. 27, as described above, the anastomosis device 620 includes an implant 204 deployed within the patient, and a discard portion 206. The discard portion 206 is fixed to the crown 607, and is not implanted in the patient. To be compatible with the splittable tool 500, the discard portion 206 is itself designed to split. That is, each crown segment 608 is fixed to a portion of the discard portion 206. When the crown segments 608 are separated, the discard portion 206 of the implant splits as well, and each portion of the discard portion 206 remains connected to its associated crown segment. Splitting of the discard portion 206 may be accomplished in a number of ways. For example, the discard portion 206 may be weakened during deployment of the implant 204 such that the radial or hoop stress induced by separation of the crown segments 608 causes the discard portion 206 to fracture. As another example, the discard portion 206 may include weakened or narrowed struts 210, 216 and/or links 222. The discard portion 206 may be made splittable in other ways, as well. For example, the discard portion 206 may include several discrete segments that are connected only through the implant 204 before the implant 204 is deployed. Upon deployment of the implant 204 and its separation from the discard portion 206, those discrete segments of the discard portion 206 are no longer connected to one another. Thus, the discard portion 206 splits at the moment the implant 204 is deployed, because the implant 204 that previously held it together has separated from it.

A passage 622 is defined through at least one crown segment 608, and a graft vessel 624 extends through the passage 622. The passage 622 is located as close as possible to the distal end of the end effector 600, thereby minimizing the stretch of the graft vessel 624 when the distal anastomosis is performed before the proximal anastomosis. Alternately, the passage 622 is positioned at any distance from the distal end of the end effector 600, where the proximal anastomosis will be performed before the distal anastomosis, and stretching of the graft vessel 624 is not a concern. The passage 622 opens to one side of the crown segment 608, such that the graft vessel 624 can easily slide out of the passage 622 after the crown 607 is split. Alternately, the passage 622 extends to one end of the crown segment 608. Alternately, the passage 622 extends across two crown segments 608, such that splitting of the crown 607 opens the slot and releases the graft vessel 624. Alternately, the passage 622 is sized to allow a distal clamp or other device attached to the opposite end of the graft vessel to pass through.

Figure 33:
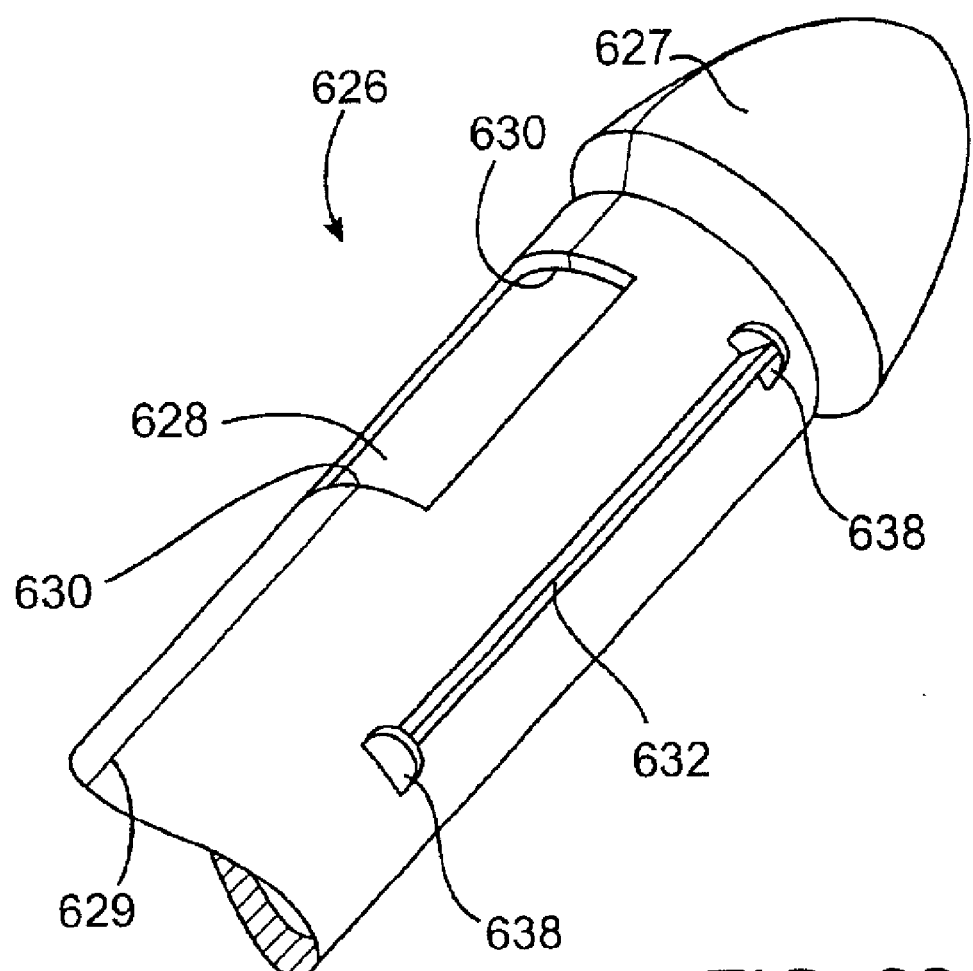
FIG. 33 is a perspective view of an expander utilized within the end effector.

Referring as well to FIG. 33, the expander 626 fits within and is substantially coaxial with the crown 607. The expander 626 slides relative to the crown 607 to deploy the device 620, as described above. The expander 626 is a hollow tubular structure. An expander slot 628 is defined through a portion of the expander 626. The expander slot 628 is located on the expander 626 in a position that corresponds to the passage 622 on one of the crown segments 608. More than one expander slot 628 may be provided in the expander 626 if more than one passage 622 is provided in the crown 607. The expander slot 628 is large enough to allow the graft vessel 624 to pass through it. Additionally, the expander slot 628 is long enough to prevent either end 630 of the slot 628 from contacting the graft vessel 624 during the travel of the expander 626 through the crown 607. The ends 630 of the slot 628 are constructed to substantially prevent damage to the graft vessel 624 in the event that one or both of those ends 630 does contact the graft vessel 624. For example, the ends 630 of the slot 628 may be sanded, machined or otherwise formed to a dull edge that will not damage the graft vessel 624. The expander 626 is splittable into two or more segments to release the graft vessel 624. In one embodiment, the expander 626 splits along a line 629 that extends through the slot 628, in order to open the slot and free the graft vessel 624.

The expander 626 also includes at least one rail 632 for interfacing with a corresponding guide 634 located on the inner surface of at least one crown segment 608. Two or more guides 634 may be provided for additional stability. Each guide 634 includes two members 636 spaced apart from one another. Those members 636 retain the associated rail 632 and provide a space through which the rail 632 can travel. The guides 634 can take a different form, if desired, as can the rails 632, as long as the rails 632 and guides 634 are able to translate relative to one another. Further, the guides 634 may be provided on the expander 626 and the rails 632 on the crown segments 608, if desired. The rails 632 include a stop 638 at each end. Each stop 638 limits the travel of the associated rail 632 along its corresponding guide 634 by contact with an end of the guide 634. In this way, travel of the expander 626 along the crown 607 is limited. Alternately, the stops 638 instead are provided at the ends of the guides 634, thereby trapping the rails 632 within and limiting the travel of the expander 626.

Figure 34:
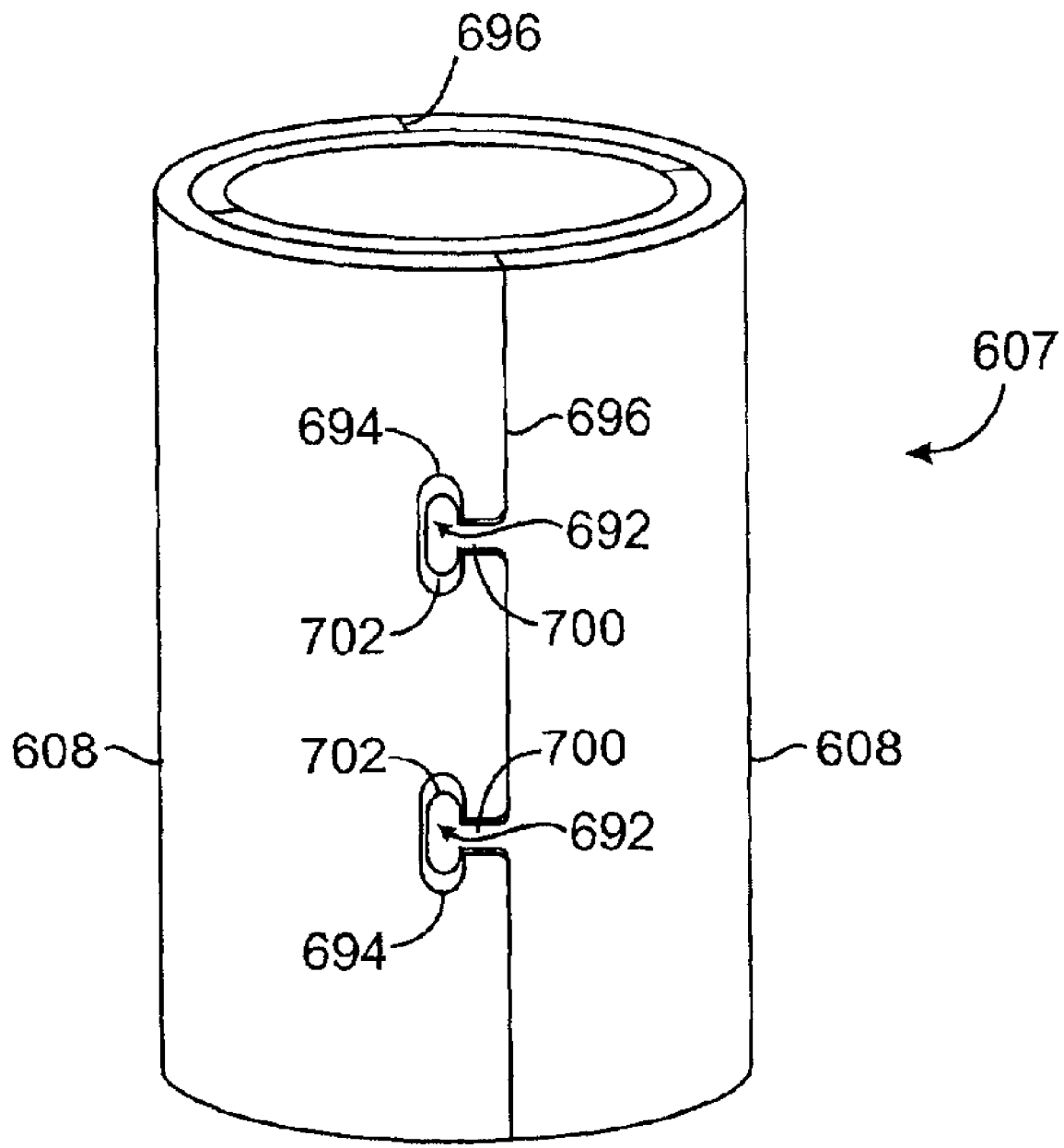
FIG. 34 is a perspective view of another embodiment of a splittable anastomosis tool.

Referring to FIG. 34, in another embodiment the crown segments 608 are held together by locking tabs 692 that interlock with locking recesses 694. The crown segments 608 also abut at seams 696 along at least a portion of their length. Alternately, the crown 607 has a unitary outer surface with a seam 696 cut through it, where locking tabs 692 connected to the surface on one side of the seam 696 interlock with locking recesses 694 formed in the surface on the other side of the seam 696. The locking tabs 692 and locking recesses 694 may be laser-cut into the crown segments 608, or formed in another way. The locking tabs 692 are smaller than the corresponding locking recesses 694. Alternately, the locking tabs 692 are substantially the same size as the corresponding locking recesses 694. The locking tabs 692 and locking recesses 694 both substantially define a "T" shape having a narrow neck 700 and a broader head 702. However, the locking tabs 692 and the locking recesses 694 may take another shape, and may be shaped differently from one another.

Each locking segment 692 releases from its corresponding locking recess 694 when the hoop stress on that locking segment 692 exceeds its tensile holding force against the locking recess 694. This hoop stress can be generated by any structure, mechanism or method. As one example, the expander 626 may include one or more flanges 698 corresponding to the location of one or more seams 696. The flange 698 extends at least partially radially to the expander, and moves along the seam 696 as the expander 626 slides relative to the crown segments 608. As the flange 626 moves closer to a position substantially underneath a particular locking segment 692, the flange 626 exerts an increasingly larger outward force on the crown segments 608 that is expressed as hoop stress within the crown 607. The size of the flange 626 and the holding force of each locking segment 692 and corresponding locking recess 694 are selected such that the hoop stress generated by the passage of a flange 626 near or under a locking segment 692 is sufficient to release it from its corresponding locking recess 694. Each locking segment 692 is flexible enough and strong enough to be retained on the crown segment 608 to which it is attached after separation from its associated locking recess 694.

Figure 35A:
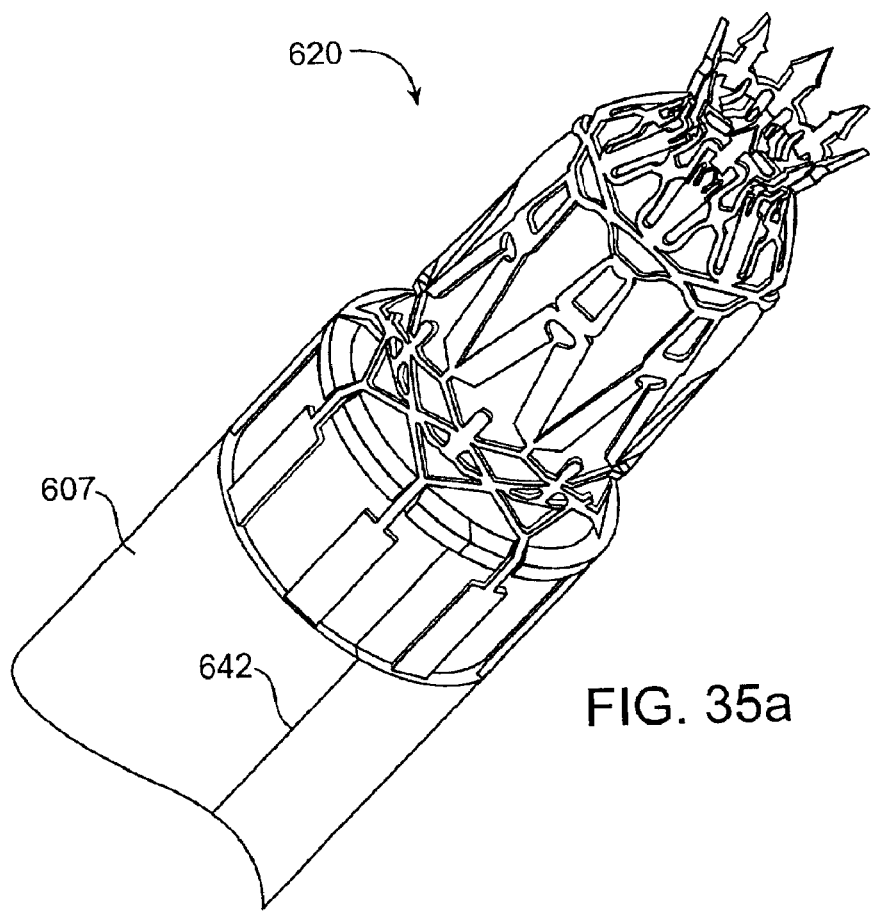
FIG. 35a is a perspective view of another embodiment of a splittable anastomosis tool.
Figure 35B:
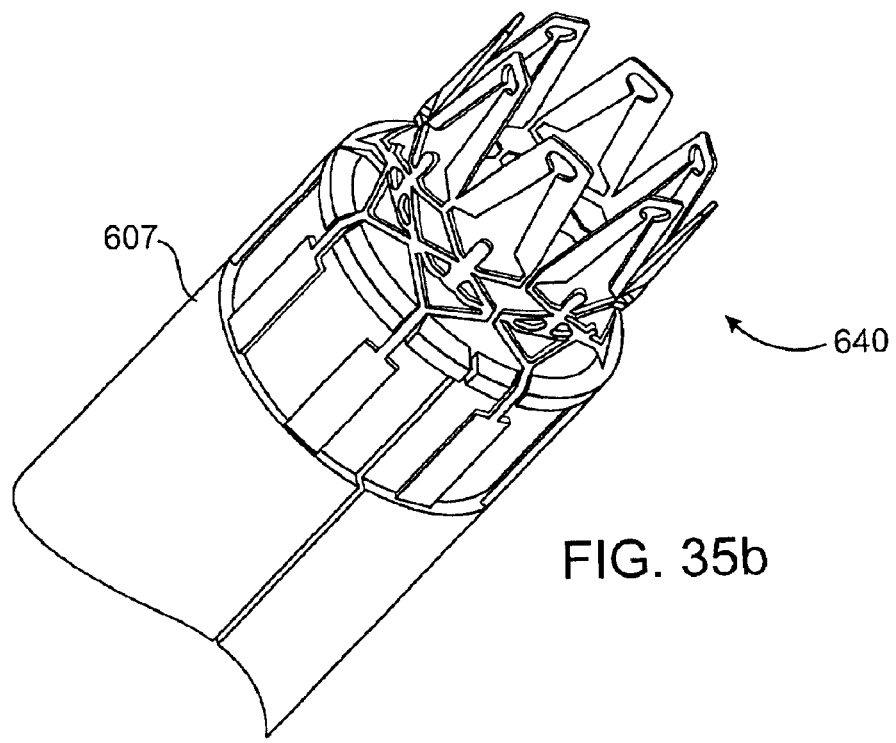
FIG. 35b is a perspective view of the tool of FIG. 35a, showing the discard section split into more than one piece.

Referring to FIG. 35a, in another embodiment the crown 607 is constructed from a single piece of plastic or similar material. The crown 607 is reduced in thickness along one or more lines 642 extending along the axial direction, such that the crown 607 is weakened along those one or more lines 642. The device 620 is mounted onto the crown 607 by ultrasonic welding, tack welding, insert molding, or other process by which a metallic part may be connected to a plastic part. The line or lines 642 split upon the application of sufficient hoop stress to the crown 607. This hoop stress is generated by the motion of the tip of the expander (not shown) as it deploys the device 620, because the tip of the expander is wider than the internal diameter of the crown 607. Referring as well to FIG. 35b, as the crown 607 splits, the discard section 640 of the device 620 splits as well, pulled apart by the hoop stress generated by the motion of the tip of the expander (not shown) and/or by the motion of the crown 607 as it splits. The expander may be configured to protrude from the end of the crown 607 at the end of its motion to release the graft vessel.

Figure 36:
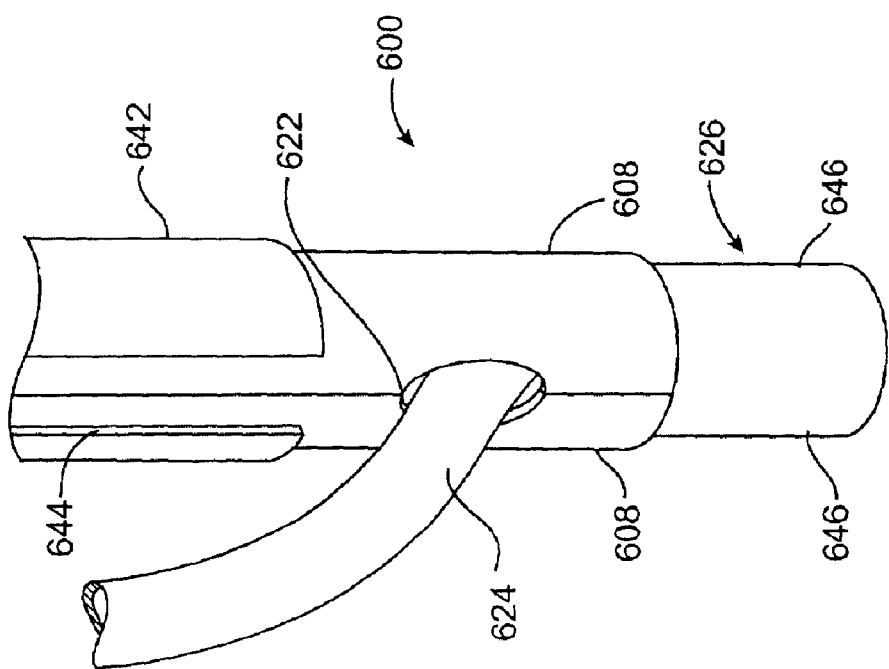
FIG. 36 is a perspective view of another embodiment of a splittable anastomosis tool.

Referring to FIG. 36, in another embodiment an outer tube 642 of the end effector 600 is coaxial with and outside of the crown 607 and the expander 626. A slot 644 extends from the distal end of the outer tube 642 along a portion of the length of the outer tube 642. The slot 644 is positioned on the outer tube 642 such that it passes over the passage 622 in the crown 607 and does not interfere with the graft vessel 624. Thus, the outer tube 642 can translate along the crown 607 without injuring the graft vessel 624. The crown 607 is separable into two or more crown segments 608 that slide within and are held together by the outer tube 642. Similarly, the expander 626 is separable into two or more expander segments 646, which are held together by the crown 607. As the outer tube 642 is retracted past a particular point at the proximal end of the crown 607, it no longer holds the crown segments 608 together, and the crown 607 splits. Consequently, the crown 607 no longer holds the expander 626 together, and the expander 626 splits. The crown 607 and/or the expander 626 may be preloaded to spring open upon retraction of the outer tube 642 to a particular point relative to the crown 607.

Figure 37:
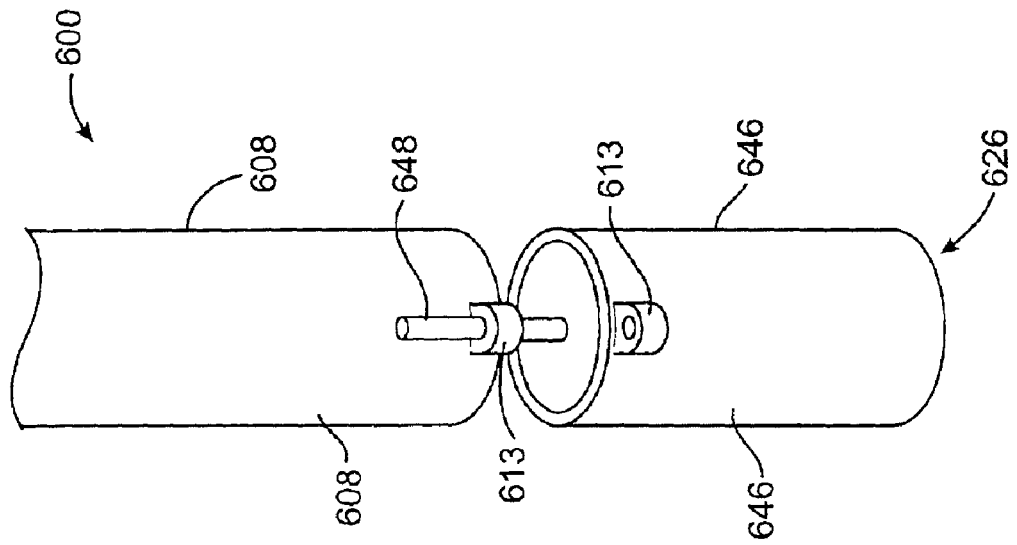
FIG. 37 is a perspective view of another embodiment of a splittable anastomosis tool.

Referring to FIG. 37, in another embodiment, a pin 648 extends through one or more locking features 613 on each crown segment 608, holding them together. When the pin 648 is removed, the crown segments 608 are freed relative to one another. The crown segments 608 may be preloaded to spring open upon removal of the pin 648. The expander 626 is separable into two or more expander segments 646, which are held together by the crown 607. When the pin 648 is removed from the locking features 613 on the crown segments 608, the crown 607 separates, and no longer holds the expander 626 together. Thus, the expander 626 splits. The expander 626 may be preloaded to spring open upon splitting of the crown 607.

Referring to FIGS. 38a–d, in another embodiment, the crown 607 includes at least two crown segments 608 separated by seams 650. At least one seam 650 defines one or more notches 652 along the interfacing edges of the crown segments 608. Alternately, the seam 650 extends substantially straight in the axial direction along the crown 607. Underneath and adjacent to the seam 650, a slot 654 extends axially along the inner surface of the crown 607, passing through the underside of the notches 652. The expander 626 is separable into two or more expander segments 646. Each expander segment 646 has a rib 656 extending from it. One dimension of the rib 656 extends radially outward from the expander segment 646, and the rib 656 additionally extends axially along at least a portion of the expander segment 646. Each rib 656 is sized to fit into and slide within a corresponding slot 654 in the crown 607. The ribs 656 on the different expander segments 646 need not be the same size, as long as they fit into and slide within the corresponding slot 654. Each expander segment 646 includes at least one expander rail 658. The expander rail 658 rides inside a guide 659 inside the crown 607. Where each expander segment 646 has an expander rail 658 on each mating side, the two adjacent expander rails 658 may slide within the guide 659. The use of the expander rails 658 in conjunction with guides 659 allows the expander 626 to smoothly translate in a substantially linear motion along the crown 607. Alternately, rails are present on the inner surface of the crown 607 and the corresponding guides are provided on the expander 626. Alternately, another structure or mechanism is used to guide the translation of the expander 626 relative to the crown 607. Alternately, the expander rails 658 and their corresponding guides 659 are not used.

Figure 38A:
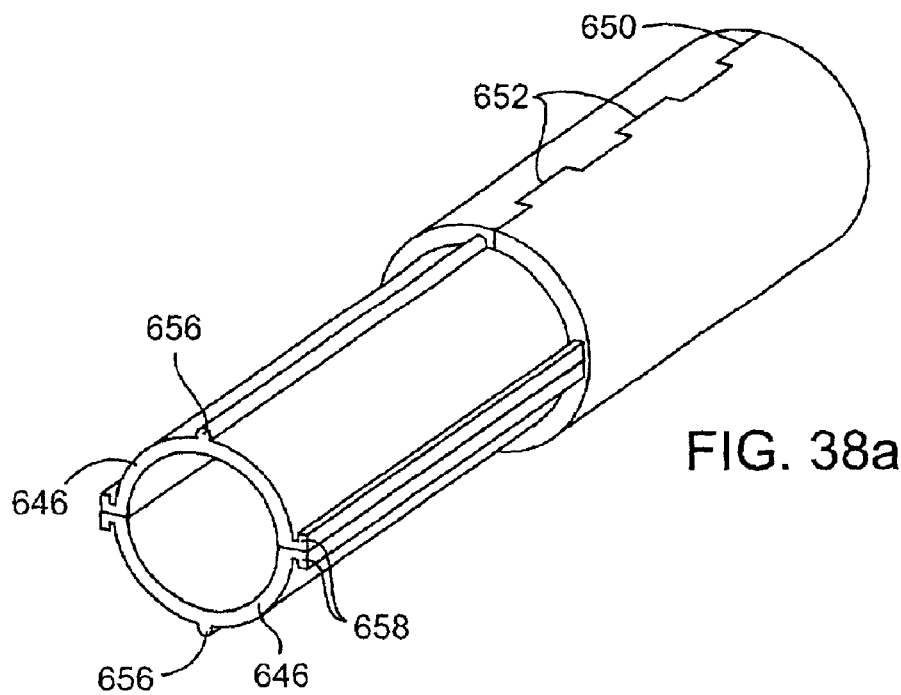
FIG. 38a is a perspective view of another embodiment of a splittable anastomosis tool.
Figure 38B:
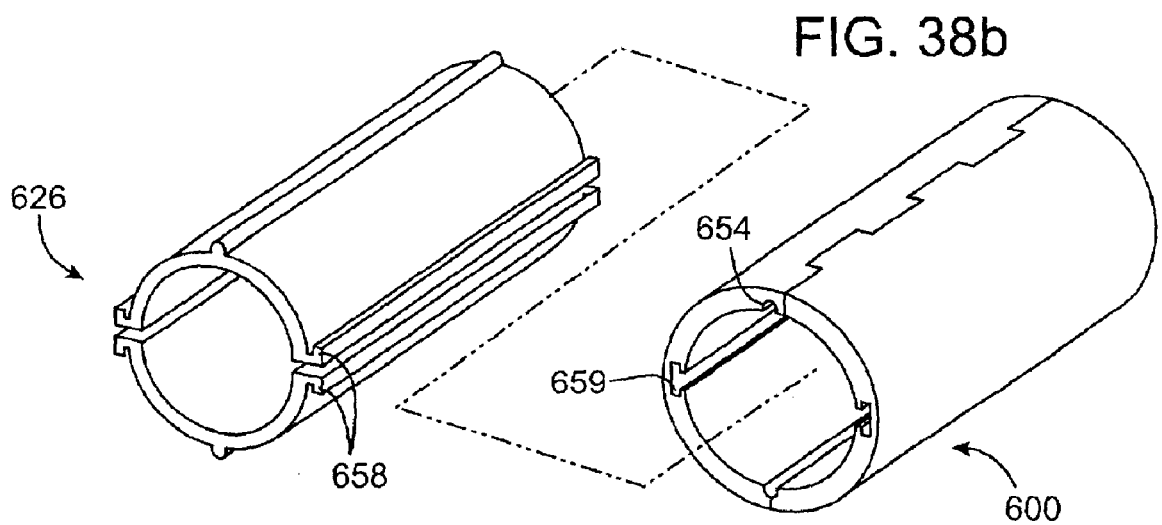
Figure 38C:
FIG. 38c is an end view of the crown of FIG. 38a in an open position.
Figure 38D:
FIG. 38d is an end view of the crown of FIG. 38a in a closed position.

The ribs 656 on the expander 626 interlock the two crown segments 608 by occupying the slots 654 passing through adjoining notches 652. Thus, the ribs 656 hold the notches 652 together in an closed position, as illustrated in FIGS. 38a and 38d. As the expander 626 is withdrawn from the crown 607 after deploying the implant (not shown), the ribs 656 travel through the slots 654, eventually passing out of the notches 652. At that time, the crown segments 608 are no longer held together, and separate to an open position, as illustrated in FIG. 38c. Thus, the axial placement of the notches 652 along the crown 607 determines the point of separation between the crown segments 608. When the expander 626 has reached the point where the ribs 656 have exited their corresponding notches 652, the expander rails 658 have also exited the corresponding guides 659. Thus, once the crown segments 608 have separated, the crown 607 in turn no longer holds the expander 626 together, and the expander 626 is free to split into separate expander segments 646. The crown 607 and the expander 626 split on different planes. That is, where the crown 607 has two substantially symmetrical crown segments 608 and the expander 626 has two substantially symmetrical expander segments 646, the crown segments 608 meet along two lines that together define a plane, and the expander segments 646 meet along two lines that together define a separate plane.

Referring to FIGS. 39a–g, in another embodiment, the crown 607 and the expander 626 split in the same plane. The crown 607 includes two crown segments 608 joined by a hinge 660. The crown 607 may be preloaded such that the crown segments 608 are forced apart from one another about the hinge 660 unless they are held together. Each crown segment 608 includes at least one notch 662 at its edge, where each notch 662 has a lip 664 with a slot 666 defined in it, the slot 666 extending in an axial direction. The notches 662 from adjoining crown segments 608 are adjacent to one another. The expander 626 is located within the crown 607 and is slidable relative to it. The expander 626 includes two expander segments 646. The expander segments 646 may be connected by a hinge 661 as well, or may be independent from one another. Each expander segment 646 includes at least one rib 668 extending outward from its edge, and extending in the axial direction along at least a portion of the expander segment 646. Each expander segment 646 is sized to fit into a corresponding slot 666 in a lip 664. As the expander 626 is withdrawn from the crown 607 after deploying the implant (not shown), the ribs 668 travel through the slots 666, eventually passing out of the notches 662. At that time, the crown segments 608 are no longer held together, and separate. Thus, the placement of the notches 662 axially along the crown 607 determines the time of separation between the crown segments 608. Correspondingly, the expander segments 646 are no longer held together, and the expander 626 splits as well. The crown segments 608 and/or expander segments 646 may be preloaded or biased to separate from one another when freed. The expander segments 646 meet along a line that is substantially parallel to and adjacent a line along which the crown segments 608 meet, where both lines are also substantially parallel to and in substantially the same plane as the axis 680 of the crown 607. Thus, the expander 626 and the crown 646 may be said to split along substantially the same plane. As shown in FIGS. 39d and 39f, in one embodiment each expander segment 646 includes a rib 668, and each notch 662 includes two slots 666, one for each rib. In this embodiment, the crown segments 608 split when both ribs 668 slide out of both slots 666 in the notches 662. As shown in FIGS. 39e and 39g, in another embodiment each expander segment 646 includes a rib 668, and each notch 668 includes a single slot 666. Thus, adjacent notches 662 each hold a rib 668 attached to a different expander segment 646.

Referring also to FIG. 40, an actuator 606 is connected to at least one expander segment 646. The actuator 606 pushes and pulls the expander segment 646, and thus the expander 626 as a whole, along the axis of the crown 607. The actuator 606 is a piece of flexible plastic or other biocompatible material connected to the expander 626, and extending within the crown 607 and the shaft 602. The use of spring steel for the actuator 606 allows the actuator 606 to move the expander 626 even when the end effector 600 is at an angle to the shaft 602, as described in greater detail below. Alternately, the actuator 606 may be one or more cables, pushrods, or any other mechanism or mechanisms configured to transmit force from the handle 830 to the distal anastomotic tool 41.

One or more of the embodiments of the end effector 600 described above may be combined in whole or in part to produce a end effector 600 that is splittable at the site of the proximal anastomosis.

The end effector 600 may be articulated relative to the shaft 602. That is, the end effector 600 may be configured to form an angle relative to the shaft 602, under the control of a user. This articulation allows the tool 500 to place the axis of the end effector 600 substantially normal to the surface of the aorta at the proximal anastomosis site. Due to the relative locations of the trocar port 64 and the heart, the end effector 600 articulates to place its axis substantially normal to the aorta, because a rigid tool extending through the trocar port 64 may not be able to easily place the axis of the end effector 600 substantially normal to the aorta within the range of anatomical geometries that may be encountered within the patient. This relationship between the end effector 600 and the aorta is optimal for punching through the aortic wall and for deploying the implant 204. Further, articulation of the end effector 600 relative to the shaft 602 allows the tip of the end effector 600 to be placed beneath either the ascending or descending aorta to provide access to a full range of potential proximal anastomosis sites. The range of articulation needed varies by patient. However, the range of articulation angles required to encompass most of the patient population is approximately 45 degrees. Thus, the articulation range provided for the end effector 600 relative to the shaft 602 is approximately 45 degrees. By initially positioning the end effector 600 relative to the shaft 602 substantially in the middle of the articulation range, the end effector 600 need only be articulated 22.5 degrees, at most, from its initial position. Alternately, greater flexibility in articulation may be provided. Alternately, the end effector 600 may initially be positioned relative to the shaft 602 at an angle other than in the middle of the articulation range. Any appropriate structure or mechanism may be used to articulate the end effector 600 relative to the shaft 602. Several examples of such structures and mechanisms are described below.

Figure 41B:
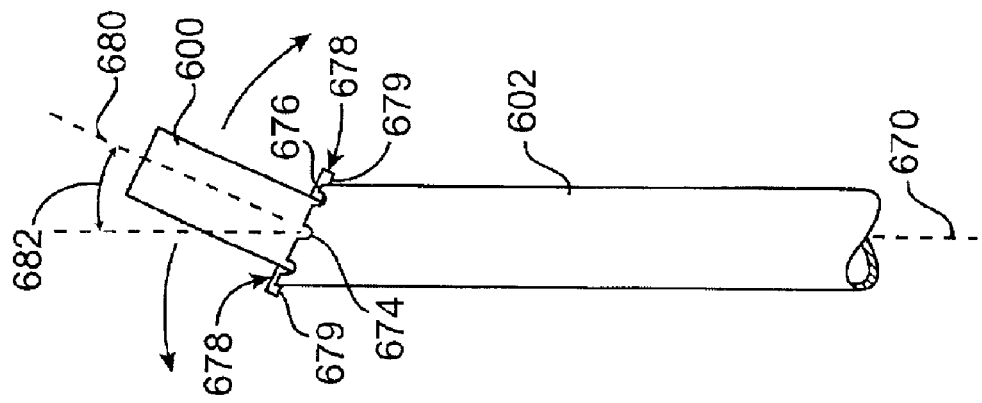
Figure 41A:
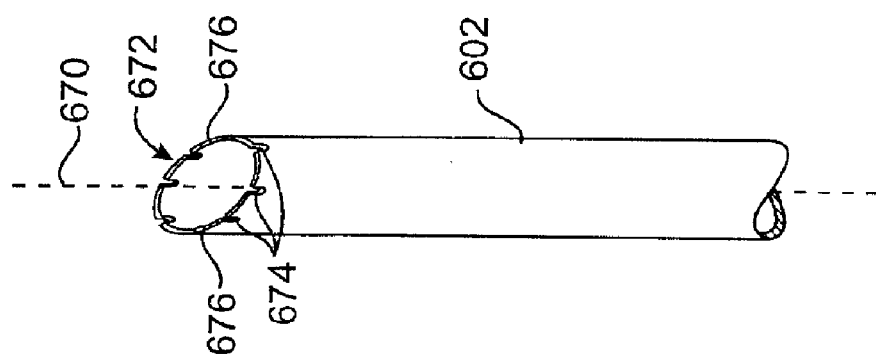
FIG. 41a is a side view of one embodiment of the shaft of an anastomosis tool having an articulated end effector.

Referring to FIGS. 41a–b, in one embodiment, the distal tip of the shaft 602 forms a plane that is angled at other than a right angle relative to the axis 670 of the shaft 602. A cam 672 is defined in the distal tip of the shaft 602. Alternately, the cam 672 is a separate item that is attached to the distal tip of the shaft 602. The cam 672 is castellated. That is, the cam 672 has a number of indentations 674 or other depressions relative to an upper surface 676. The cam 672 can be seen most clearly in FIG. 41a. The end effector 600 includes a corresponding cam follower 678. The cam follower 678 includes at least two rods 679 or other structures extending radially outward from the end effector 600, in a plane substantially normal to the axis 680 of the end effector 600. Where two rods 679 are used, they are substantially coaxial. The rods 679 are long enough such that they extend outward to the cam 672. Further, the cross-section of each rod 679 of the cam follower 678 is sized to seat within each of the indentations 674 of the cam 672. Advantageously, the bottom of each indentation 674 is also angled relative to the axis 670 of the shaft 602 to provide for seating of the cam follower 678 within selected indentations 674.

Because the cam 672 is in a plane angled relative to the axis 670 of the shaft 602, and the cam follower 678 is in a plane substantially normal to the axis 680 of the end effector 600, the angle 682 of the end effector 600 relative to the shaft 602 is substantially constant as the end effector 600 is rotated relative to the shaft 602. The rotary motion of the end effector 600 relative to the shaft 602 thus substantially defines a conic surface about the axis 670 of the shaft 602. Consequently, the distal tip of the end effector 600 defines a substantially circular range of motion. Therefore, motion of the shaft 602, and motion of the end effector 600 relative to the shaft 602, moves the distal tip of the end effector 600 through a range of motion and changes the angle of the axis 680 relative to the surface of the aorta. In this way, the distal tip of the end effector 600 can be manipulated to the proximal anastomosis site more easily. Alternately, the cam follower 678 is in a plane other than one normal to the axis 680 of the end effector 600. This plane may be selected to provide a desired range of motion for the distal tip of the end effector 600 as the end effector 600 moves relative to the shaft 602. When the end effector 600 has reached a selected position, the cam follower 678 seats into the appropriate indentations 674.

The end effector 600 may be rotated by any structure or mechanism configured to transmit torque to the end effector 600. For example, a tube (not shown) outside the end effector 600 may be utilized to transmit torque to the end effector 600 and drive its rotary motion. Further, the end effector 600 may be moved axially by any structure configured to transmit axial forces to the end effector 600. For example, such a structure may be a tube (not shown) outside the end effector 600, or a separate actuator (not shown) such as described above. The end effector 600 is moved axially in a distal direction to allow rotation of the cam follower 678 relative to the cam 672, and is moved proximally to seat the cam follower 678 into two or more indentations 674 in the cam 672. When the end effector 600 has been rotated to a selected position, the end effector 600 can be locked into that position by holding the cam follower 678 into the two or more indentations 674 in which it is seated.

Figure 42C:
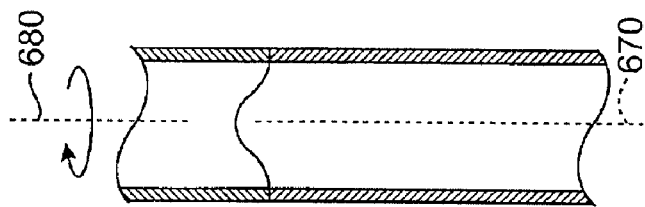
FIG. 42c is a side cross-section view of the tool of FIG. 42a where the end effector and shaft have a second relationship to one another.
Figure 42B:
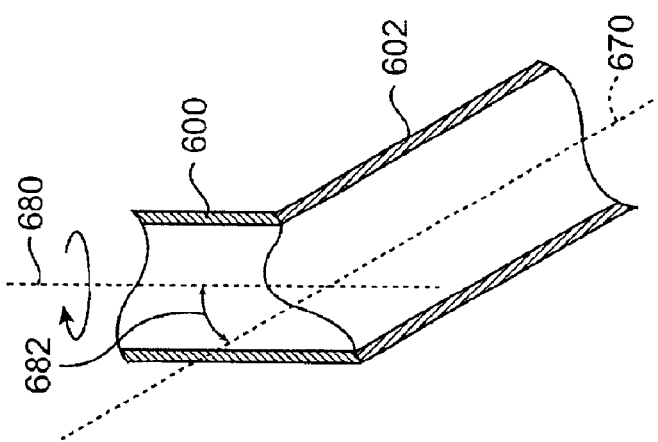
FIG. 42b is a side cross-section view of the tool of FIG. 42a where the end effector and shaft have a first relationship to one another.
Figure 42A:
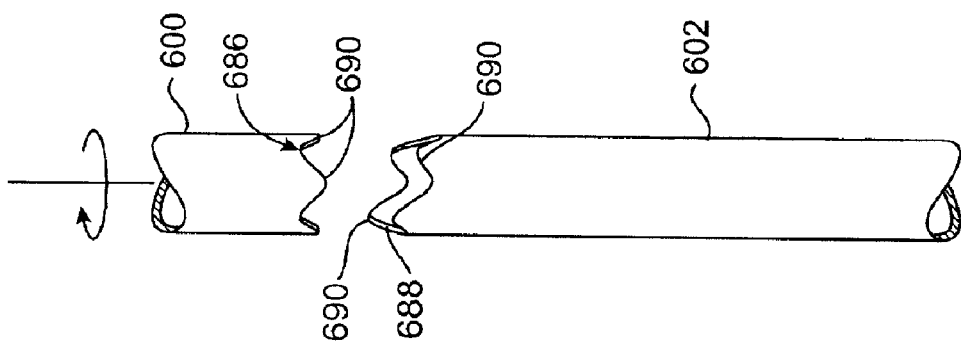
FIG. 42a is a side view of another embodiment of an anastomosis tool having an articulated end effector.

Referring to FIGS. 42a–c, in another embodiment, a first cam 686 is provided on the proximal end of the end effector 600, and a second cam 688 is provided on the distal end of the shaft 602. The cams 686, 688 each have at least one lobe 690. The cams 686, 688 are asymmetrical. That is, the lobe or lobes 690 are not cut identically on each cam 686, 688, but rather differ in number, size, shape or other characteristics. However, the lobes 690 are cut on each cam 686, 688 to allow for stable seating of the end effector 600 against the shaft 602 in two or more different positions. Because the cams 686, 688 are asymmetrically, the angle 682 of the end effector 600 relative to the shaft 602 can vary as the end effector 600 is rotated relative to the shaft 602. The angle 682 may be configured to vary from a minimum of zero degrees, where the axis 670 of the shaft 602 is coaxial with the axis 680 of the end effector 600, to a selected maximum. The rotary position of the distal tip of the end effector 600 relative to the shaft 602 can be adjusted by rotating the shaft 602 while holding the end effector 600 stationary relative to it, or by other means. Thus, the rotary motion of the end effector 600 relative to the shaft 602 defines an asymmetrical cone. In this way, the distal tip of the end effector 600 can be manipulated to a selected one of a large number of orientations quickly and easily. As described above, the end effector 600 can be moved relative to the shaft 602 by any appropriate structure or mechanism.

Figure 43:
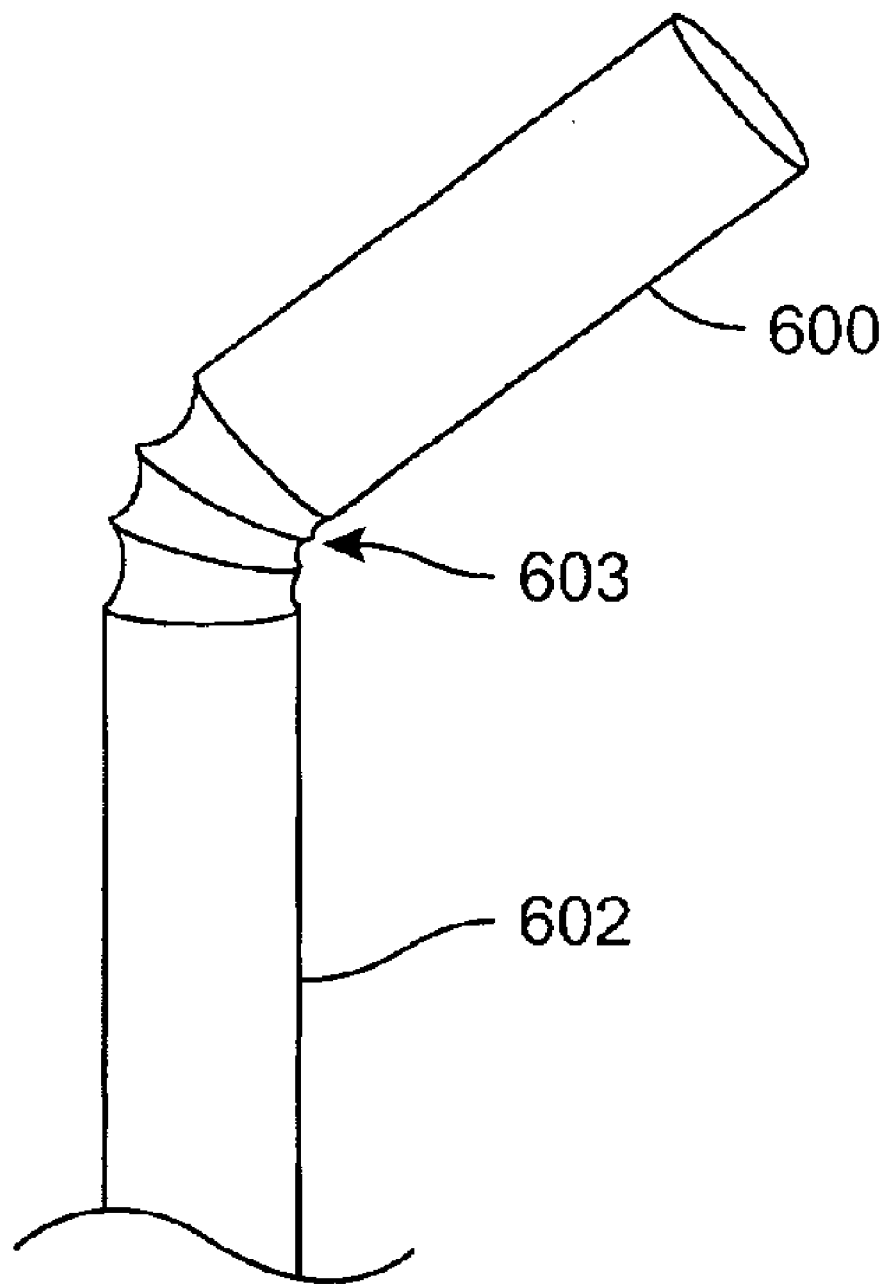
FIG. 43 is a side view of another embodiment of an anastomosis tool having an articulated end effector.

Referring to FIG. 43, in another embodiment, the end effector 600 and shaft 602 are connected by a flexible joint 603. The flexible joint 603 is a wire or plastic winding having substantially the same diameter as the end effector 600 and the shaft 602, covered by Dacron or other flexible biocompatible material. The end effector 600 can then be moved relative to the shaft 602 manually, by adjusting the end effector 600 by hand. Alternately, the end effector 600 can be moved by the use of cables or other structures or mechanisms connected to the end effector 600 that extend out of the patient. For example, a number of cables maybe connected to the end effector 600 along its inner periphery, where those cables extend through the interior of the shaft 602 out of the patient. By tensioning one or more of the cables relative to the others, the end effector 600 can be angled relative to the shaft 602 due to the flexibility provided by the flexible joint 603. Alternately, the flexible joint 603 may simply be constructed from flexible material. In this way, the joint 604 provides for motion of the end effector 600 and shaft 602 relative to one another. The flexible joint 603 may be another structure or mechanism, if desired.

Figure 43A:
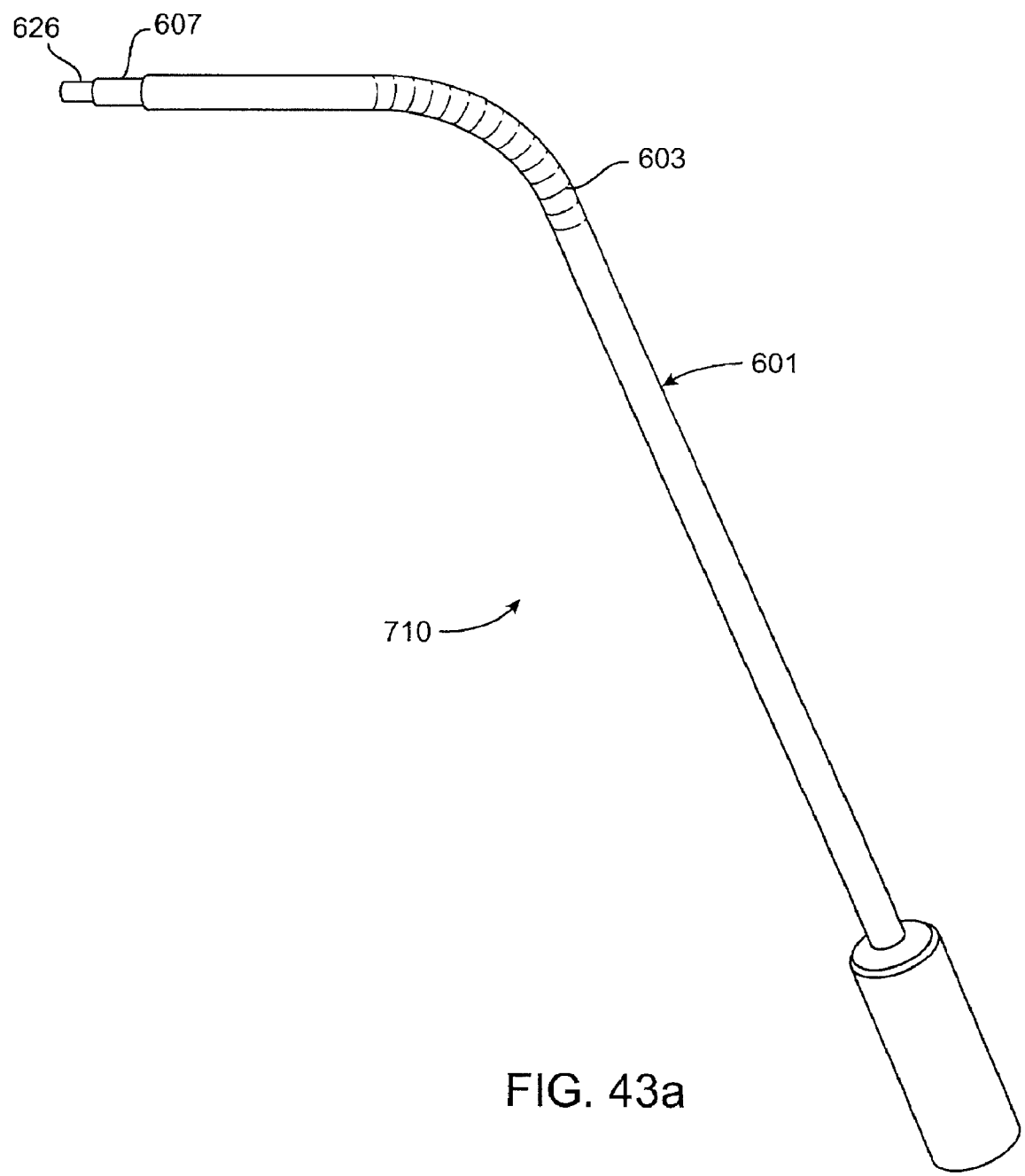
FIG. 43a is a side view of another embodiment of an anastomosis tool having an articulated end effector, where the end effector is the distal end of a shaft.

Referring to FIG. 43a, a holder tube 601 includes a flexible joint 603 made by cutting kerfs in the holder tube 601, where that holder tube 601 has substantially the same diameter as the end effector 600 and the shaft 602. The crown tube 607 and the expander 626 are slidably disposed at the distal end of the holder tube 601. The crown tube 607 and the expander 626 arc substantially rigid, and are short enough such that neither substantially enters the flexible joint 603. Alternately, the crown tube 607 and the expander 626 are both flexible, and are configured to slide within the flexible joint 603. The end effector 600 can then be moved relative to the shaft 602 manually, by adjusting the end effector 600 by hand to plastically deform the holder tube 601. Alternately, the end effector 600 can be moved by the use of cables or other structures or mechanisms connected to the end effector 600 that extend out of the patient.

Figure 44:
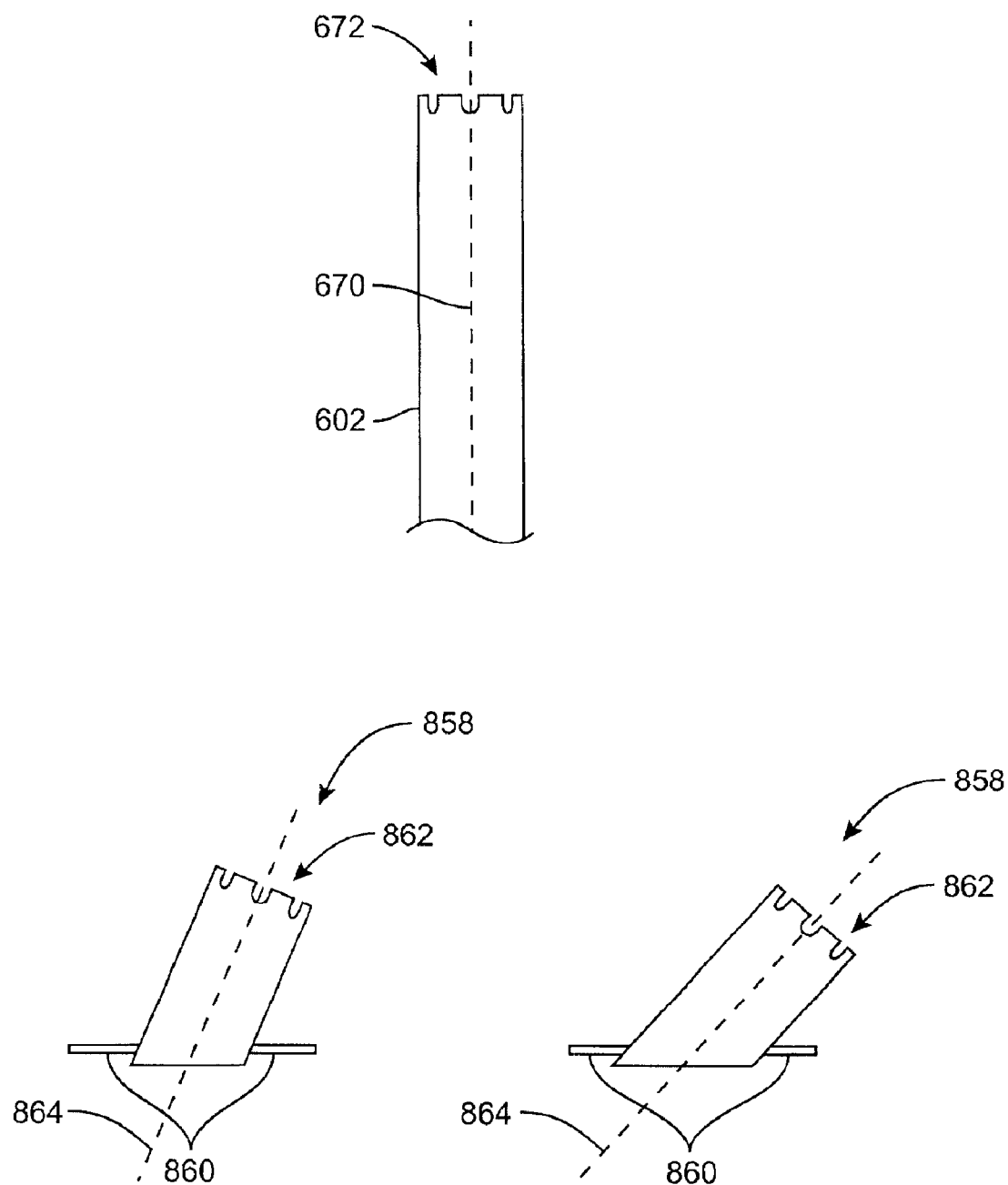
FIG. 44 is a side view of another embodiment of an anastomosis tool having an articulated end effector.

Referring to FIG. 44, in another embodiment, the distal tip of the shaft 602 is a castellated cam 672, as described above with respect to FIG. 41. The cam 672 is perpendicular to the axis 670 of the shaft 602. Alternately, the cam 672 has another angle relative to the axis 670 of the shaft 602. One or more spacers 858 are provided for use in conjunction with the shaft 602. A spacer 858 fits between the shaft 602 and the end effector 600, where each spacer 858 is configured to produce a different angle between the shaft 602 and the end effector 600. In this way, the angle between the shaft 602 and the end effector 600 can be adjusted manually by changing the spacer 858 used between them.

Each spacer 858 has a substantially cylindrical cross-section with a diameter substantially the same as the end effector 600 and the shaft 602. Each spacer 858 includes a spacer cam follower 860 configured to interface with the cam 672. The spacer cam follower 860 is configured relative to the spacer 858 in the same manner as described above in FIG. 41 with regard to the cam follower on the crown. Each spacer 858 has a castellated spacer cam 862 at its distal tip. The cam follower 678 on the end effector 600 seats in the castellations on the spacer cam 862. Each spacer 858 is angled differently relative to its cam follower 678. That is, the angle between the axis 864 of each spacer 858 and its cam follower 860 is different for each spacer. A range of different possible angles between the end effector 600 and the shaft 602 is thereby provided, depending on the spacer 858 selected. If no spacer 858 is utilized, the angle between the end effector 600 and the shaft 602 is defined by the angle of the cam 672 at the distal end of the shaft 602. Other types of spacer 858 may be used between the end effector 600 and the shaft 602 to adjust the angle between them.

Referring back to FIG. 41, another embodiment of an articulation structure is shown. A ball-tipped tower 606 extends distally from the distal end of the shaft 602. The ball of the tower 606 seats in a socket 866 at the proximal end of the end effector 600. The tower 606 is positioned at the edge of the shaft 602, rather than its center, to allow a clear axial path through the shaft 602. Hence, a second tower 606 (not shown) may be provided on the other side of the distal tip of the shaft 602 for stability, where that second tower 606 interfaces with a second socket 866 on the end effector 600. The ball-and-socket joint formed by the ball of the tower 606 and the socket 866 allows for angular motion between the end effector 600 and shaft 602. Alternately, the tower 606 may extend axially from the distal end of the shaft 602, where the tower 606 and socket 866 are substantially coaxial with the axis 670 of the shaft 602. Alternately, the tower 606 extends proximally from the proximal end of the end effector 600, and the socket 866 is provided in the shaft 602.

Figure 45:
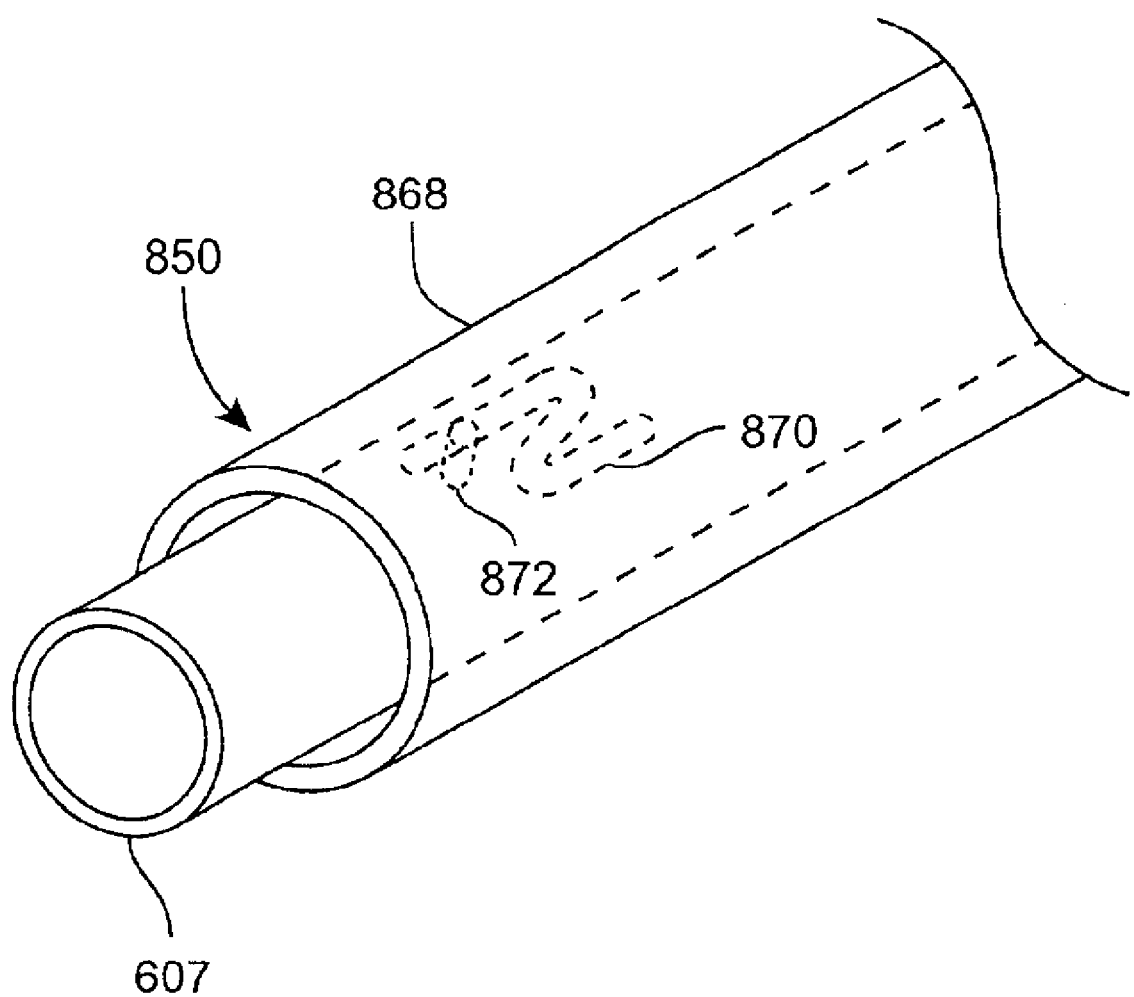
FIG. 45 is a perspective view of an another embodiment of an articulated anastomosis tool.

Referring to FIG. 45, another embodiment is shown. The end effector 600 is the crown tube 607, and a separate shaft 602 is not utilized. The crown tube 607 is slidably positioned within an introducer tube 868. Both the crown tube 607 and the introducer tube 868 are substantially rigid. The crown tube 607 has a smaller diameter than, and is spaced apart from, the introducer tube 868. Two or more cam paths 870 are defined in the inner surface of the introducer tube 868. A corresponding number of cam followers 872 extend from the outer surface of the crown tube 607. Each cam follower 872 extends into a corresponding cam path 870. The length of the cam followers 872 separates the crown tube 600 from the introducer tube 868. The cam paths 870 are offset from one another and/or asymmetrical, such that axial motion of the crown tube 607 relative to the introducer 868 moves the cam followers 872 along these offset paths. That is, the cam paths 870 are offset from one another and/or asymmetrical such that motion of the cam followers 872 along them results in angling of the crown tube 607 relative to the introducer 868. That is, by allowing one or more cam followers 872 to proceed further forward than one or more other cam followers 872, the crown tube 607 tilts relative to the introducer tube 602. The space between the crown tube 607 and the introducer 602 provides room for this tilting motion.

Figure 46:
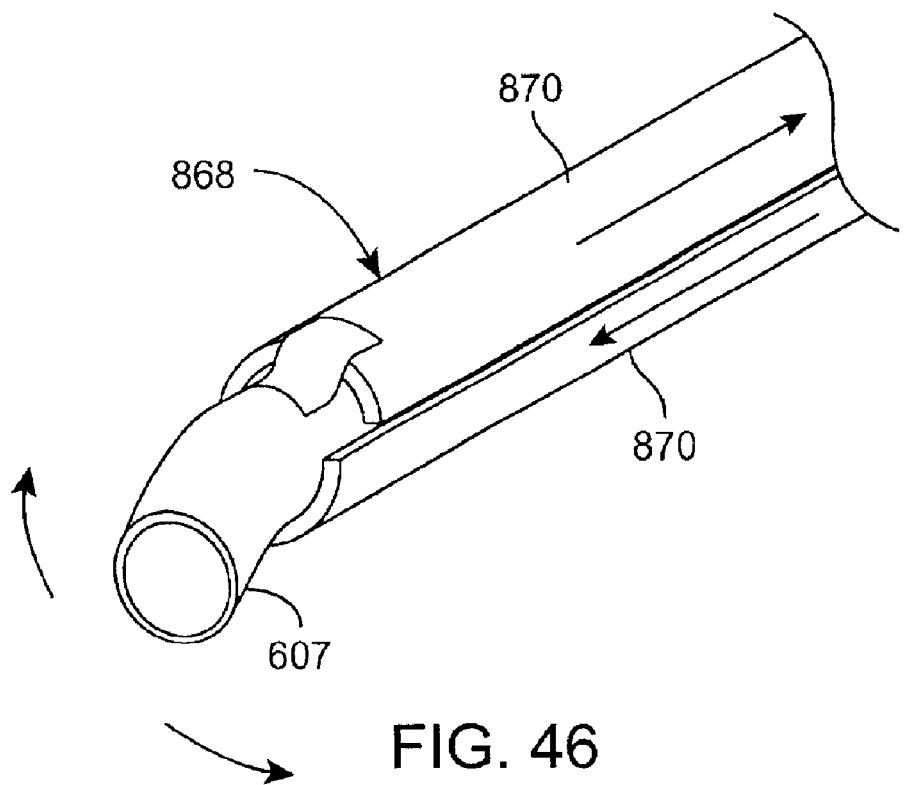
FIG. 46 is a perspective view of another embodiment of an articulated anastomosis tool.

Referring to FIG. 46, another embodiment is shown. As in FIG. 50, the end effector 600 is the crown tube 607, and a separate shaft 602 is not utilized. The crown tube 607 is positioned within an introducer tube 868. The introducer tube 868 is substantially rigid, and the crown tube 607 is substantially flexible. Alternately, the crown tube 607 is substantially flexible at and near its distal end, and substantially rigid otherwise. The introducer tube 868 is formed from two or more introducer segments 870 which are slidable relative to one another. The crown tube 607 is affixed to the distal end of the introducer tube 868. Consequently, as the introducer segments 870 are slid relative to one another, portions of the crown tube 607 are tensioned, causing the distal end of the crown tube 607 to move relative to the axis of the introducer. In this way, the angle of the distal end of the crown tube 607 can be controlled.

Other structures or mechanisms may be used to articulate the end effector 600. For example, a peristaltic system may be used, in which water, saline or other biocompatible fluid is pumped into selected passages in the end effector 600, causing them to expand relative to other passages, and thereby changing the angle of the end effector 600.

Figure 47:
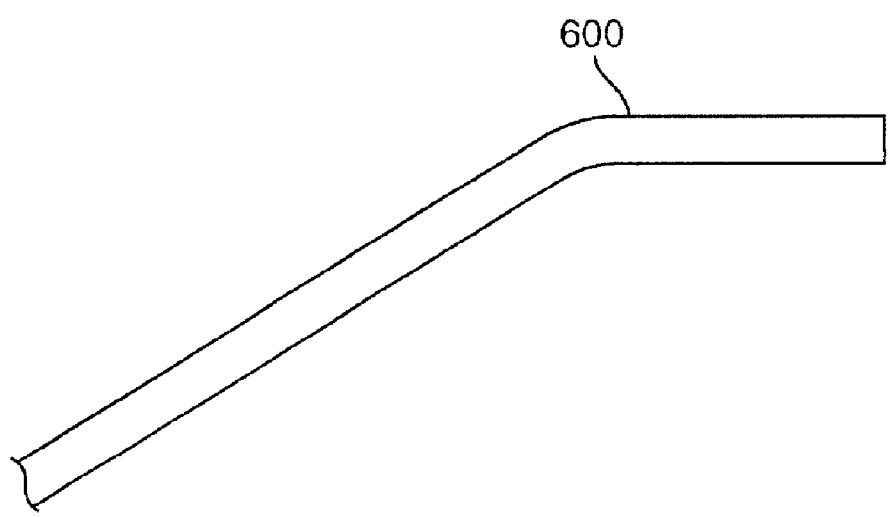
FIG. 47 is a side view of an anastomosis tool having an angled end.

Referring to FIG. 47, another embodiment is shown. The end effector 600 is bent near its tip. This configuration of the end effector 600 may be used with a tool that utilizes a separate end effector 600 and shaft 602, or one that utilizes a unitary crown tube 607, such as described above with regard to FIGS. 45–46. Further, this configuration may be used in conjunction with any of the articulation mechanisms or structures described above, or with other mechanisms or structures. The end effector 600 is bent to an angle substantially in the middle of the range of angular motion desired, reducing the amount of articulation required. Alternately, the end effector 600 may be bent to a selected angle based on an x-ray or angiogram for a particular patient, or based on other considerations.

Figure 48:
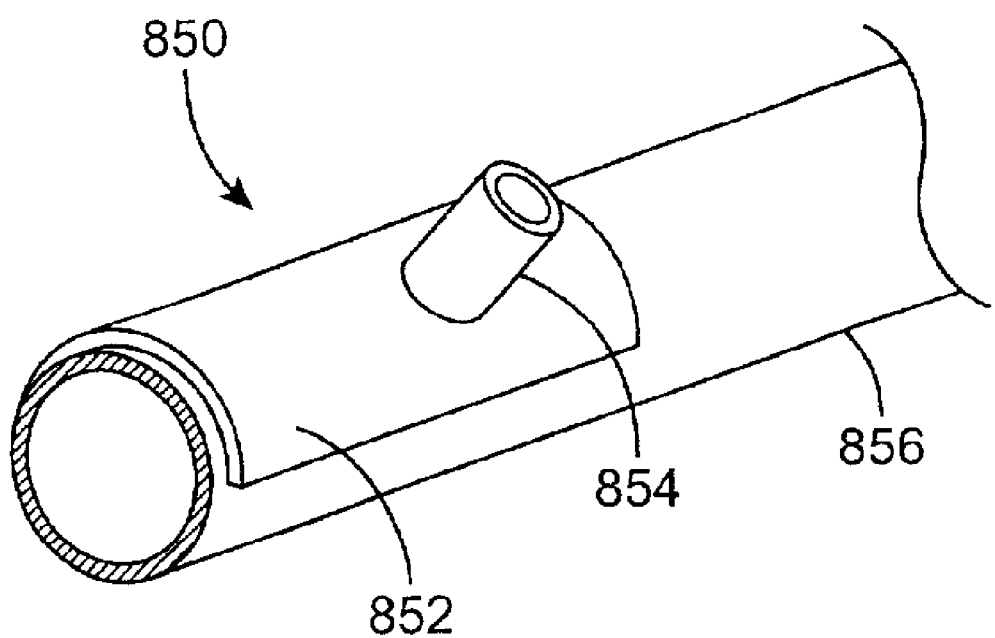
FIG. 48 is a side view of a fitting optionally placed on the target vessel.

Determining whether the distal tip of the implant applicator tool is substantially normal to the target vessel may be performed visually, by looking at the proximal anastomosis site through an endoscope or other visualization tool. In another embodiment, referring to FIG. 48, a tee fitting 850 maybe used to establish normalcy between the distal tip of a tool and the surface of the aorta 856. The tee fitting 850 has a curved base 852 that is placed on the aorta 856. The tee fitting 850 may be attached to the aorta 856 temporarily by an adhesive, a clamp or other structure or mechanism. Alternately, the tee fitting 850 may be held against the aorta 856 with a forceps or other tool inserted into the thoracic cavity through a trocar port 64, 66. The tee fitting 850 includes a hollow guide 854 that is positioned to extend substantially normal to the surface of the aorta 856. Thus, to slide the tip of a tool onto the guide 854, the distal tip of that tool has to be substantially normal to the surface of the aorta 856. In this way, normalcy between the distal tip of the tool and the aorta 856 is established. The tee fitting 850 may be used with any of the embodiments of the application tool described above, or with any other application tool. The tee fitting 850 is also useful in maintaining registration between the opening created in the aorta and the tool used to deploy the anastomosis device into that opening.

One or more of the embodiments of the end effector 600 described above may be combined in whole or in part to produce a end effector 600 that is articulated to reach the site of the proximal anastomosis. Once the end effector 600 is placed at the proximal anastomosis site, the implant 204 is deployed into the patient's aorta Once the proximal anastomosis device has been deployed, the proximal deployment tool can be removed. In the case where the graft vessel clamp is attached after the proximal anastomosis has been performed, removal of the proximal tool would result in blood leakage from the end of the graft vessel. Therefore, upon removal of the non-splittable proximal tool, a standard bulldog clamp or similar device is deployed to clamp the graft vessel. The bulldog clamp can be deployed automatically within the chest cavity upon removal of the non-splittable proximal tool. The bulldog clamp can be placed on the graft vessel before the deployment of the proximal device, because the splittable tool allows the graft vessel to pass out of the tool.

Referring to FIG. 49, an integrated stabilizer 704 is then placed at the distal anastomotic site. Alternately, the integrated stabilizer 704 may be placed at the distal anastomotic site before performing the proximal anastomosis. The integrated stabilizer 704 includes a head 712 connected to a distal anastomotic tool 41 and an epicardial dissector 716. The epicardial dissector 716 may be provided separately, as described in more detail below. The structure and operation of the distal anastomotic tool 41 and of the epicardial dissector 716 are discussed in greater detail below. The head 712 is substantially oval in shape, thereby minimizing the amount of heart surface held beneath it. The head 712 is open in the center to allow access to the distal anastomotic site by the distal anastomotic tool 712 and the epicardial dissector. In one embodiment, the head 712 is substantially 20 mm in width by 50 mm in length. However, other dimensions of the head 712 may be used. Further, the head 712 may take another shape, such as a circle or an open U-shape. The head 712 is substantially in contact with the surface of the heart around its periphery in order to minimize tissue motion. The combination of the head 712, the distal anastomotic tool 41 and the epicardial dissector 716 are substantially no more than 25 mm thick to allow for insertion into the patient at the distal anastomotic site. Alternately, the head 712 and its associated components 41, 716 may be thicker, depending on the size of the large trocar port 66 through which the head 712 and associated components 41, 716 are inserted. The head 712 includes a lower edge 713 that contacts the heart, where that lower edge 713 may be chamfered. The lower edge 713 is a long arc that forms the majority of an ellipse. An opening 715 in the ellipse allows the graft vessel to be freed after anastomosis is performed. The lower edge 713 may be shaped differently, if desired. Alternately, a separate head 712 is not used, and the distal anastomotic tool 41 and the epicardial dissector 716 are connected directly to the linkage 706. Alternately, the distal anastomotic tool 41 is directly connected to the epicardial dissector 716, and one of the two is connected directly to the linkage 706.

Integrated endoscopes 734 and light sources 736 may also be included on the integrated stabilizer 704. The cables (not shown) associated with the endoscopes 734 and the light sources 736 may run through the passage 724 within the linkage 706, which is described in greater detail below. For example, fiber optic cables for carrying photons to the light sources 736 may run through the passage 724, in addition to fiber optic cables for carrying images from the endoscopes 734 to the operator of the tool 710. Alternately, these cables may run outside the linkage 706. By providing integrated endoscopes 734 and light sources 736, the tool 710 is simpler and more convenient to use. Additional components may be included on the integrated stabilizer 704. For example, a carbon dioxide blower (not shown) and a blood suction device (not shown) may also be provided as part of the integrated stabilizer 704, in order to keep the surgical field clear for visualization.

The integrated stabilizer 704 is connected to a linkage 706, which in turn is connected to a handle 708. The linkage 706 is connected to one side of the head 712. Alternately, the linkage 706 may be connected to another part of the head 712. For example, the linkage 706 may be connected to the rear of the head 712, where the head 712 is to be used through a sub-xyphoid approach. The combination of these components 704, 706, 708 may be referred to as the stabilizer tool 710. The integrated stabilizer 704 is moved to the distal anastomotic site by moving the stabilizer tool 710 as a whole. The integrated stabilizer 704 is navigated to the distal anastomotic site by utilizing one or more endoscopes, as well as the mark or marks previously made on the heart at the distal anastomotic site.

Figure 50:
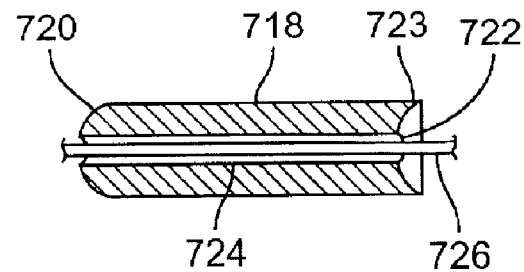
FIG. 50 is a cross-section view of a link in a selectively compliant linkage utilized in a surgical tool.
Figure 51:
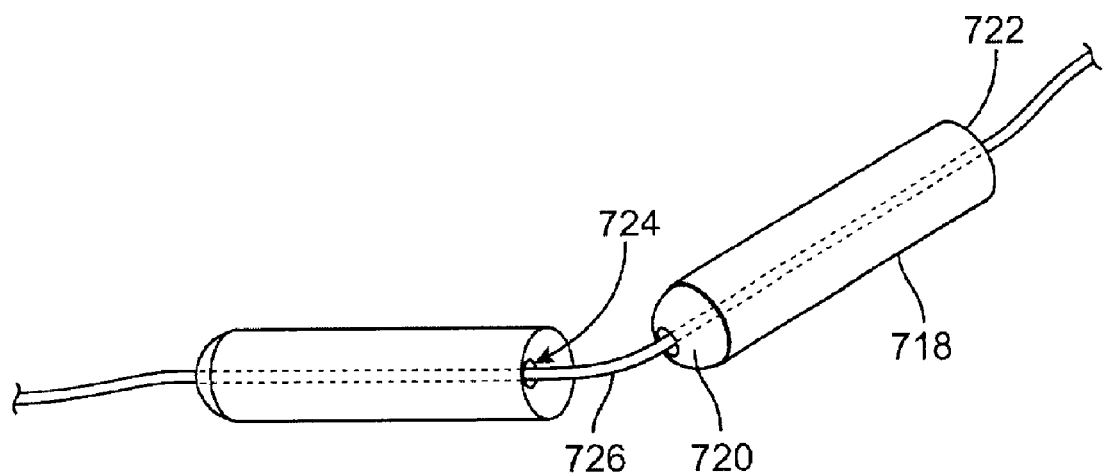
FIG. 51 is a perspective exploded view of a link in a selectively compliant linkage utilized in a surgical tool.

Referring as well to FIGS. 50-51, in one embodiment the linkage 706 includes a number of linkage segments 718; Each linkage segment 718 has a convex hemispherical distal end 720 and a concave hemispherical proximal end 722. Thus, the distal end 720 of one linkage segment 718 can fit within the proximal end 722 of the neighboring linkage segment 718 and allow an amount of angular motion relative to it. The linkage segments 718 are constructed from a material having little stiction and a low coefficient of friction, to enhance the compliance of the linkage 706. The concave proximal end 722 of each joint includes a circumferential flange 723 that functions as a stop to prevent over-rotation of the corresponding convex distal end 720 and allow only a predetermined maximum amount of angular motion per joint. The use of the flanges 723 provides stability to the tool 710. The linkage segment 718 at the distal end of the linkage 706 and the linkage segment 718 at the proximal end of the linkage 706 may be constructed differently to interface with, or may be built into, the integrated stabilizer 704 and the handle 708 respectively. Advantageously, the number of linkage segments 718 is minimized, to enhance the stability of the tool 710 and simplify its construction. Alternately, the distal end 720 and the proximal end 722 of each linkage segment 718 may be sections of an ovoid or other shape, where that shape allows the linkage segments 718 to move relative to one another.

The linkage 706 is constructed to be long enough to allow the integrated stabilizer 704 to reach all of the potential distal anastomotic sites on each side of the heart from the corresponding large trocar port 66. That is, when the tool 710 is inserted into the thoracic cavity through the large trocar port 66 on the left side of the heart, the linkage 706 is long enough to allow the integrated stabilizer 704 to access all of the distal anastomotic sites on the left side of the heart. Alternately, linkage 706 may be long enough to allow the integrated stabilizer 704 to access all of the distal anastomotic sites on both sides of the heart from either side of the chest or from a sub-xyphoid approach. Similarly, when the tool 710 is inserted into the thoracic cavity through the large trocar port 66 on the right side of the heart, the linkage 706 is long enough to allow the integrated stabilizer 704 to access all of the distal anastomotic sites on the right side of the heart. In one embodiment, two separate tools 710 may be provided, one configured for use with the distal anastomotic sites on the left side of the heart, and one configured for use with the distal anastomotic sites on the right side of the heart.

A substantially cylindrical passage 724 is defined through each linkage segment 718. Alternately, the passage 724 may take another shape. An actuator 606 is a cable that extends through the passages 724 of the linkage segments 718. Alternately, the actuator 606 may be another structure, such as a strip of spring steel, one or more cables, pushrods, or any other mechanism or mechanisms configured to transmit force from the handle 830 to the distal anastomotic tool 41. The actuator 606 is connected to the handle 708 at its proximal end and to the integrated stabilizer 704 at its distal end. When the actuator 606 is loose relative to the linkage 706, the linkage segments 718 are free to move relative to one another. This freedom to move results in the linkage 706 being compliant. When the actuator 606 is tightened relative to the linkage 706, as by causing it to shorten, the actuator 606 exerts a substantially axial force along each linkage segment 718, pushing the linkage segments 718 together and increasing the friction between them. By tightening the actuator 606 a predetermined amount, the linkage segments 718 can be substantially locked together, such that the linkage 706 becomes noncompliant. The actuator 606 may be tightened and loosened by any appropriate mechanism, such as a knob 728 or lever connected to its proximal end. To simplify use, the actuator 606 may be switchable between two discrete states, one resulting in a compliant linkage 706 and the other resulting in a noncompliant linkage 706. For example, the actuator 606 may be connected to the knob 728, where the knob 728 is rotatable between a first discrete position in which the actuator 606 is loose and the linkage 706 is compliant and a second discrete position in which the actuator 606 is tight and the linkage 706 is noncompliant. However, the actuator 606 may be adjusted through a range of states, if desired. Further, other types of actuator 606 and linkage 706 may be used. In use, the linkage 706 is substantially rigid when entering the thoracic cavity, then is changed to be compliant once the integrated stabilizer 704 is in position on the heart at the distal anastomotic site. The compliant linkage 706 allows the integrated stabilizer 704 to move with the heart when it is in position at the distal anastomotic site, in order to compensate for respiratory and cardiac motion. The integrated stabilizer 704 is also articulated relative to the linkage 706 to adjust its pitch and roll angles in order to seat properly at the distal anastomotic site. That is, three degrees of freedom are provided for the integrated stabilizer 704, such that at least a portion of the inner edge 713 of the stabilizer head 712 can be positioned firmly on the heart at the distal anastomotic site.

Figure 52:
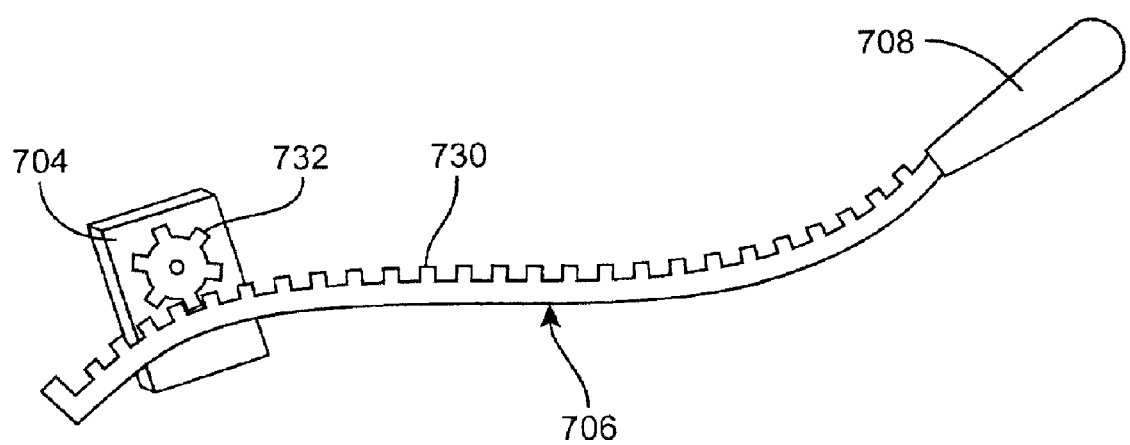
FIG. 52 is a perspective view of an alternate embodiment of a surgical tool.

Referring to FIG. 52, in another embodiment, the linkage 706 is substantially non-compliant at all times. This type of linkage 706 may be advantageously used with certain integrated stabilizers 704 described below that do not track the heart, but instead position themselves between the heart and the chest wall to stabilize a region of the heart at the distal anastomotic site relative to the chest wall. In one embodiment, a non-compliant linkage includes a rack 730 of gear teeth adapted to engage a pinion 732. The pinion 732 is connected to the integrated stabilizer 704, which is shown as a block for clarity in describing the linkage 706. Motion of the pinion 732 against the rack 730 results in motion of the integrated stabilizer 704. The pinion 732 may be held against the rack 732 by any appropriate mechanism or structure. For example, a second rack (not shown) may be provided opposite the rack 730 to trap the pinion 732 between them. As another example, the pinion 732 may be biased against the rack 730 by a spring clip, retainer or other device adapted to hold the pinion 732 onto the rack 730. The pinion 732 may be moved relative to the rack 730 by any appropriate mechanism or structure as well. For example, the integrated stabilizer 704 may be connected to a push rod (not shown), where motion of the push rod into or out of the thoracic cavity induces the integrated stabilizer 704 to move along the rack 730. As another example, the pinion 732 may be biased toward the distal end of the linkage 706, such that release of a button or other retainer on or near the handle 708 causes the pinion 732 to move toward the distal end of the linkage 706. As another example, the pinion 732 may be connected to a drive motor (not shown) that urges the pinion 732 along the rack 730. A different type of noncompliant linkage 706 may be utilized if desired. The integrated stabilizer 704 may be articulated relative to the noncompliant linkage 706 to allow the pitch and roll angles to be adjusted as needed to allow the integrated stabilizer 704 to seat properly at the distal anastomotic site. The pitch and roll angles may be adjusted outside the patient by hand, or inside the patient via a remotely-controlled mechanism. Such articulation may be performed in a manner analogous to that described above with regard to articulating the end effector 600 of the proximal tool 500 relative to the shaft 602, or may be performed in a different way. As another example of a noncompliant linkage, the linkage may be constructed from a material that is plastically deformed by hand to a desired shape before insertion into the patient.

Figure 53:
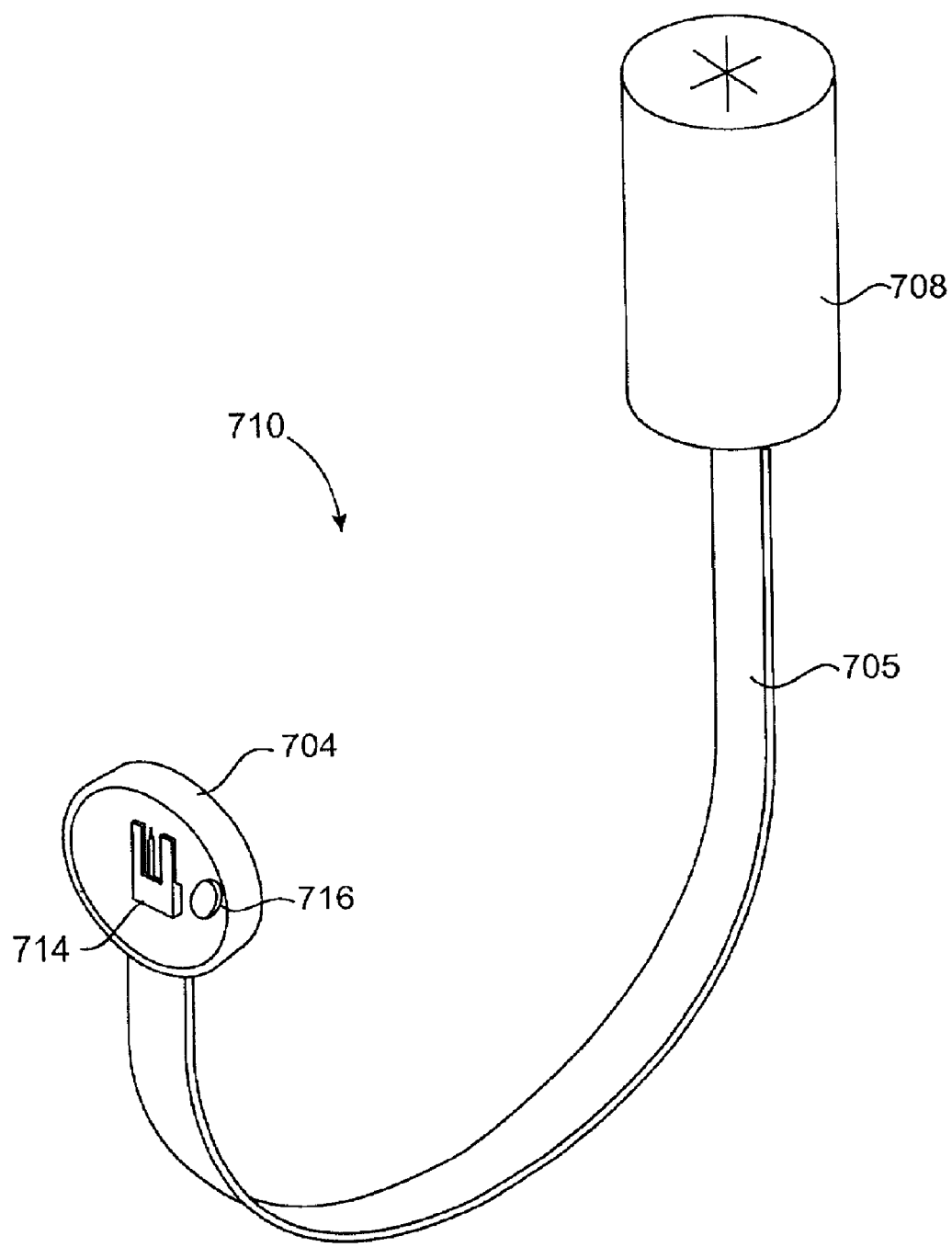
FIG. 53 is a side view of an alternate embodiment of a surgical tool.

Referring to FIG. 53, in another embodiment, the tool 710 includes an integrated stabilizer 704 connected to a flexible strip 705 that in turn is connected to a handle 708. The strip 705 is a ribbon of spring steel or other compliant material that is strong enough to support the integrated stabilizer 704 and transmit force to it. This tool 710 is compliant at all times. Cables (not shown) or other control mechanisms attached to the distal anastomotic tool 714 and/or the epicardial dissector 716 on the integrated stabilizer 704 may run along the strip 705, or may independently extend out of the patient through one or more trocar ports 64, 66. Actuators (not shown) may also be connected to cables or other control mechanisms, for fine control over the positioning of the integrated stabilizer 704 as a whole.

Figure 54:
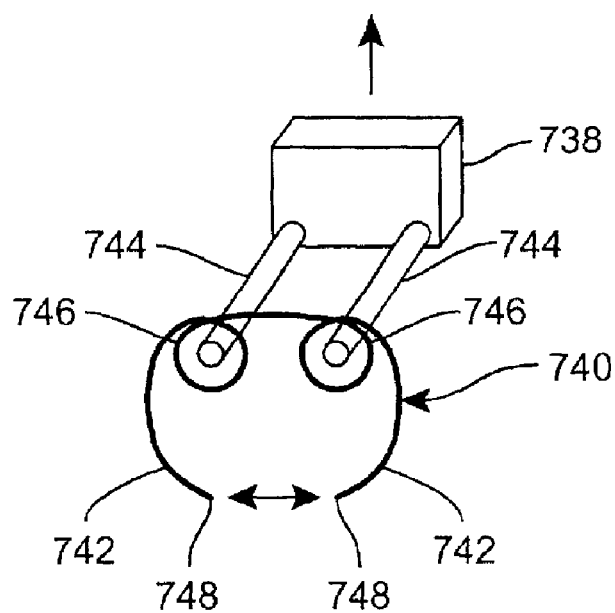
FIG. 54 is a perspective view of a clip deployer utilized with an embodiment of the integrated stabilizer.

Once the integrated stabilizer 704 is placed on the heart at the distal anastomotic site, it is secured relative to the heart. The integrated stabilizer 704 is secured to the heart utilizing myocardium clips placed around the periphery of the head 712. Alternately, the integrated stabilizer 704 may be secured to the heart in another way. For example, suction devices may be placed on the integrated stabilizer 704 to generate suction that holds the integrated stabilizer 704 to the heart. Referring to FIGS. 49 and 54, in one embodiment, a number of clip deployers 738 are positioned around the periphery of the head 712. One or more of the clip deployers 738 may be movable relative to the head 712. At least one clip 740 is deployed from each clip deployer 738, and held by the clip deployer 738 after deployment. In this way, the clips 740 grip the heart, and maintain registration between the integrated stabilizer 704 and the heart.

In one embodiment, three clip deployers 738 are utilized on the integrated stabilizer 704. Most branches of the left anterior descending (LAD) artery on the surface of the heart travel to the left. Thus, to minimize potential contact between a clip 740 and a coronary artery, one of the clip deployers 738 is located on the left of the head 712 and two of the clip deployers 738 are located on the right of the head 712. At least one clip 740 is used to secure the integrated stabilizer 740 to the heart. Advantageously, three clips 740 are used to secure the integrated stabilizer 740 against the heart. At least 5 mm of space is provided between each clip deployer 738 and any vessel on the surface of the heart. To provide this space, the clip deployers 738 may be configured to move relative to the head 712 to provide adequate clearance for vessels on the surface of the heart. Alternately, the clip deployers 738 are fixed and the head 712 is manipulated to provide clearance. Alternately, more than three clip deployers 738 are provided, and only clip deployers 738 having sufficient distance from vessels on the surface of the heart are activated. The maximum penetration of the clips 740 into the heart is substantially 3.5 mm. By penetrating to this shallow depth, the likelihood of puncturing a submyocardial coronary artery is minimized.

Each clip deployer 738 is activated by moving it upward. The clip deployer 738 includes two rods 744 extending outward from it, substantially normal to the direction in which the clip 740 is moved. The clip 740 held by the clip deployer 738 includes two loops 746, where each rod 744 extends through one of the loops 746. The clip 740 has a complex shape, having two ends 748 that move downward and toward one another when the clip 740 is pulled upward by the loops 746. As shown in FIG. 45, the clip 740 begins at one end 748, curves upward and leftward, then curves into a loop 746, continuing rightward to curve into a second loop 746, then curves downward and leftward. Thus, when the rods 744 pull upward on the loops 746, the ends 748 of the clip move downward and toward each other, into the epicardium and the myocardium. Conversely, when the rods 744 are moved downward, the clip 740 is pulled downward by the loops 746, and the ends 748 of the clip move upward and away from one another, releasing the heart. The clips 740 are fabricated from a superelastic alloy such as NiTi which allows the clips 740 to be self-securing when deployed into the myocardium, and still retain adequate elastic characteristics to be removable from the myocardium when the distal anastomosis is complete. Alternately, the clips 740 are formed from stainless steel, and are deformed when deployed into the myocardium and deformed to withdraw from the myocardium.

Figure 55:
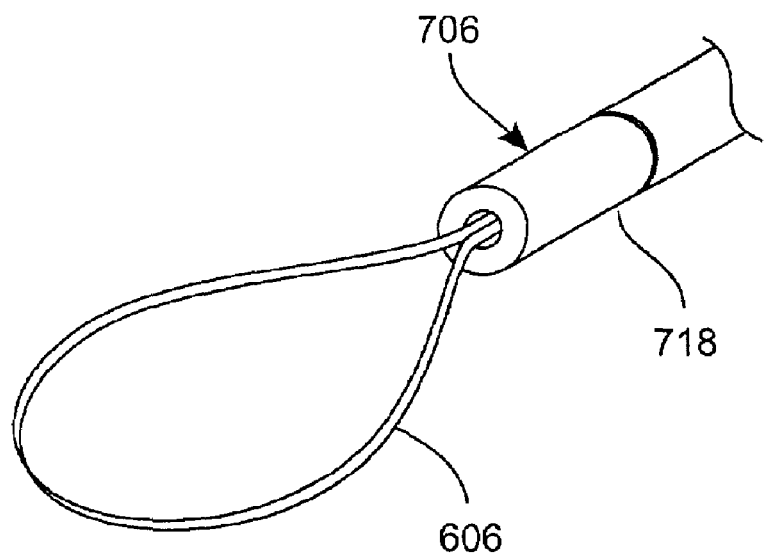
FIG. 55 is a perspective view of an actuator utilized with an embodiment of the integrated stabilizer.

Referring as well to FIG. 55, the actuator 606 is a ribbon of nitinol, other elastic material, or plastically deformable material extending out of the linkage 706 and around the inner edge 713 of the head 712. The head 712 is not shown, for clarity. When the linkage 706 is rigid upon insertion of the integrated stabilizer 704 into the thoracic cavity of a patient, the actuator 606 is tightly tensioned. The clip deployers 738 may interface with the actuator 606 such that, upon the release of a preselected amount of tension from the actuator 606, the clip deployers 738 move upward to deploy the clips 740 and grip the heart. This preselected amount of tension is more than the amount of tension in the actuator 606 when the linkage 706 is compliant and moving along with the beating heart. Conversion of the amount of tension in the actuator 606 to motion of the clip deployers 738 may be accomplished with any appropriate mechanism. Alternately, the clip deployers 738 deploy the clips 740 when tension in the actuator 606 is increased. Alternately, the actuator 606 slips relative to the head 712, where that slippage is converted to motion of the clip deployers 738. Alternately, the clip deployers 738 and/or clips 740 may operate in a different manner or be activated in another manner.

Figure 56:
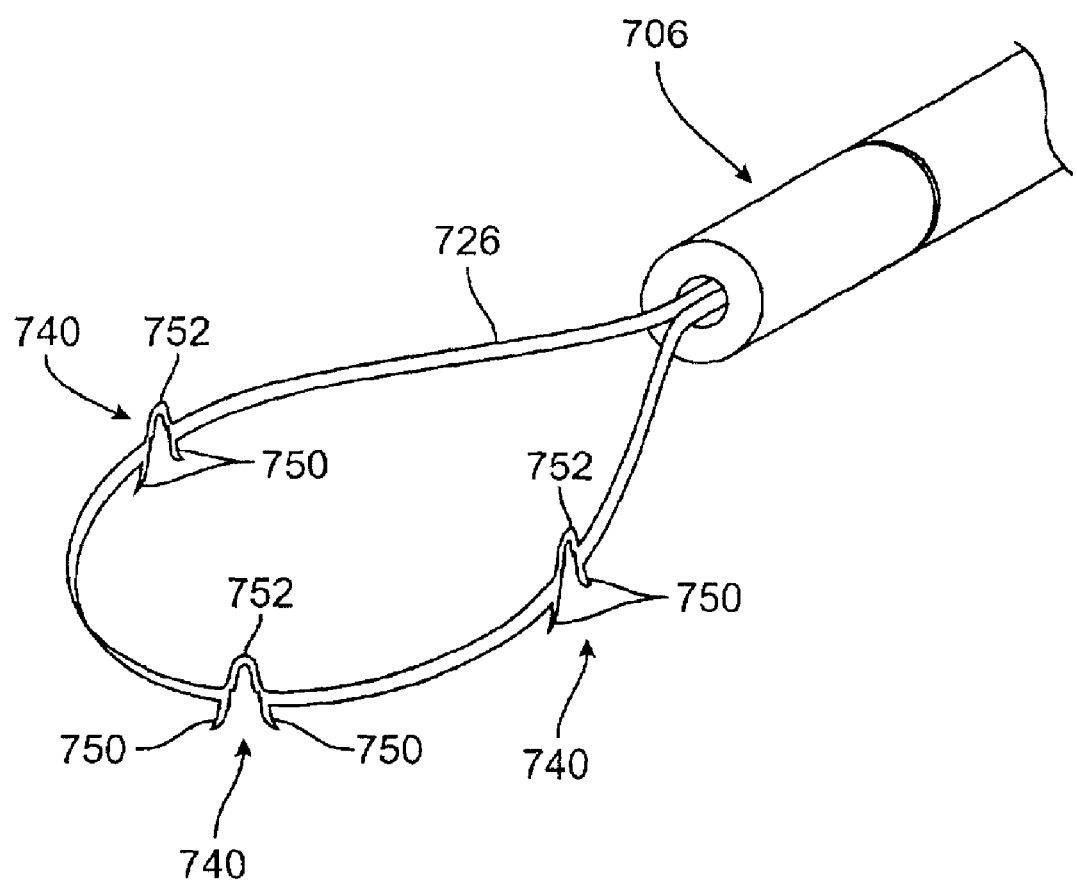
FIG. 56 is a perspective view of another embodiment of an actuator utilized with the integrated stabilizer.

Referring to FIG. 56, in another embodiment, the actuator 606 is a ribbon of nitinol or other elastic alloy extending out of the linkage 706 and around the head 712, as in FIG. 55. The head 712 is not shown, for clarity. In this embodiment, the clips 740 are formed directly in the actuator 606 around the periphery of the head 712. That is, the clips 740 and the actuator 606 are unitary. Three clips 740 are positioned around the actuator 606 in the same manner in which the three clip deployers 738 are positioned around the head 712, as described above, in order to maximize clearance between the clips 740 and vessels on the surface of the heart.

Each clip 740 includes at least one tine 750, where each tine 750 extends downward from the actuator 606. Each tine 750 in a clip 740 angles at least partially away from the other. Each tine 750 may also include a bending feature 752 that allows enough deformation of the actuator 606 to allow the tines 750 to move as needed. The tines 750 may be configured differently and/or the bending feature 752 may be omitted, if desired. When the linkage 706 is rigid upon insertion of the integrated stabilizer 704 into the thoracic cavity of a patient, the actuator 606 is tightly tensioned. The clips 740 are configured such that, upon the release of a preselected amount of tension from the actuator 606, the tines 750 move downward and outward away from one another, penetrating the epicardium and myocardium and gripping the heart. The bending feature 752 allows the actuator 606 to flex at the location of the clip 740, thereby allowing the tines 750 to move in this manner. This preselected amount of tension is more than the amount of tension in the actuator 606 when the linkage 706 is compliant and moving along with the beating heart. Conversely, when tension greater than the preselected amount of tension is once again applied to the actuator 606, the tines 750 move upward and inward, releasing the heart. Other unitary configurations of clips 740 and the actuator 606 may be used.

Other structures or mechanisms may be used to secure the integrated stabilizer 704 relative to the heart. One set of such structures and/or mechanisms rigidly supports a section of the myocardium from the chest wall. That is, a structure is positioned between and engages both the chest wall and the heart, thereby stabilizing a portion of the myocardium by restricting its motion relative to the chest wall.

Figure 57:
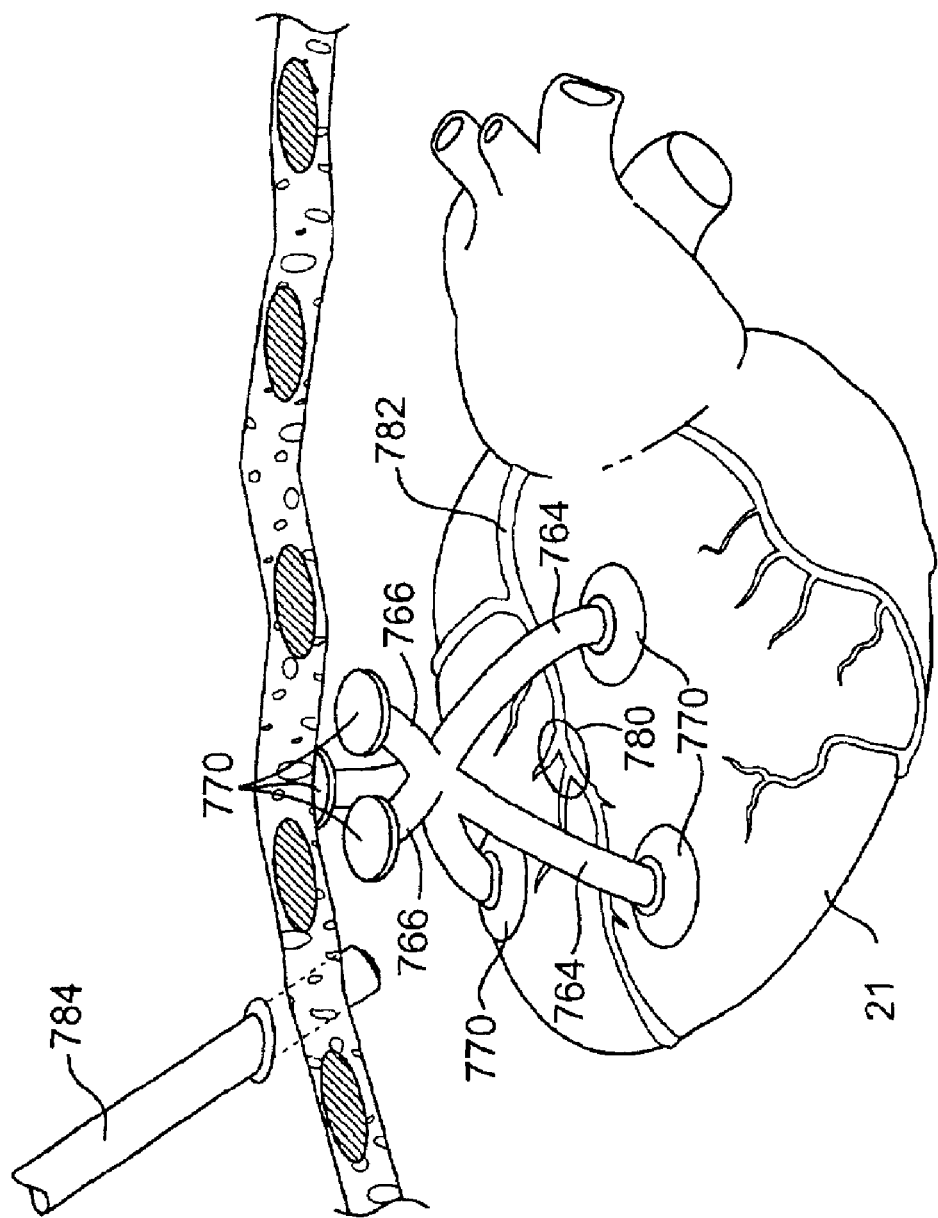
FIG. 57 is a perspective view of another embodiment of the integrated stabilizer.

Referring to FIG. 57, in one embodiment, the integrated stabilizer 704 includes a tower 762. The tower 762 includes three substantially rigid downward-extending supports 764 and three substantially rigid upward-extending supports 766, meeting at a central junction 768. Additional supports 764, 766 may be provided. Further, the supports 764, 766 need not all meet at a single junction 768. A pad 770 may be formed into or connected to the end of one or more of the supports 764, 766. Each pad 770 has a larger surface area than the cross-sectional area of the support 764, 766 to which it is connected in order to spread the load transmitted through the associated support 764, 766 over a larger surface area. Alternately, pads 770 are not provided, and the supports 764, 766 themselves have adequate cross-sectional area to spread the load transmitted through the tower 762 into the patient without transmitting excessive load to the heart 21 or the chest wall. Alternately, the pads 770, the upper supports 766 and/or the lower supports 764 are compliant.

The distal anastomotic tool and the epicardial dissector are connected to the central junction 768 of the tower 762 to provide for flexibility in motion. For clarity in illustrating the tower 762, the distal anastomotic tool and the epicardial dissector are not shown. The distal anastomotic tool and epicardial dissector can move laterally, up and down, and rotate within the space between the lower supports 764 in order to access the distal anastomotic site 780. Alternately, the distal anastomotic tool and epicardial dissector may be connected to one or more of the lower supports 764 and/or upper supports 766, as long as they have adequate freedom of motion to reach the distal anastomotic site 780.

The integrated stabilizer 704 is inserted into the patient via the large trocar port 66. In one embodiment, the integrated stabilizer 704 is moved to the distal anastomotic site with a rigid tool 710 as described above with regard to FIG. 52, where the integrated stabilizer 704 is connected to the pinion 732. At least one tether 786 is connected to the distal anastomotic tool 41 and/or the epicardial dissector 716 in order to control them from outside the thoracic cavity. The tether 786 may be secured to the rack 730 out of the way of the pinion 732, or may be independent of the rack 730. An endoscope 784 is inserted into the patient through a separate small trocar port 64, or through the large trocar port 66. The separation between the lower supports 764 provides for broad endoscopic viewing access to the distal anastomotic site 780. An endoscope (not shown) and fiber optic lights (not shown) may be mounted on the tower 762, to provide for added convenience.

When in place on the heart 21, the tower 762 is lodged between the heart 21 and the chest wall (not shown). That is, the substantially rigid tower 762 moves a portion of the heart 21 away from the chest wall to make room for itself in the thoracic cavity. The pads 770 on the upper supports 766 engage the chest wall, and the pads 770 on the lower supports 764 engage the heart 21. Thus, the tower 762 stabilizes a portion of the myocardium located substantially in the area having a perimeter defined by the pads 770 on the lower supports 764. The tower 762 is positioned such that the distal anastomotic site is located within that area, in order to stabilize that site. As shown in FIG. 57, the distal anastomotic site 780 is located on the left anterior descending artery 782. However, the distal anastomotic site 780 may be located on any other appropriate coronary artery. The integrated stabilizer 704 is produces tension, also referred to as countertraction, on the epicardium. The target vessel at the distal anastomotic site is thus tensioned as well. This tension is advantageous for performing the distal anastomosis. The tower 762 also may be anchored to the heart using clips, suction ports, or other mechanisms, as described above with regard to FIGS. 56–58.

Figure 58:
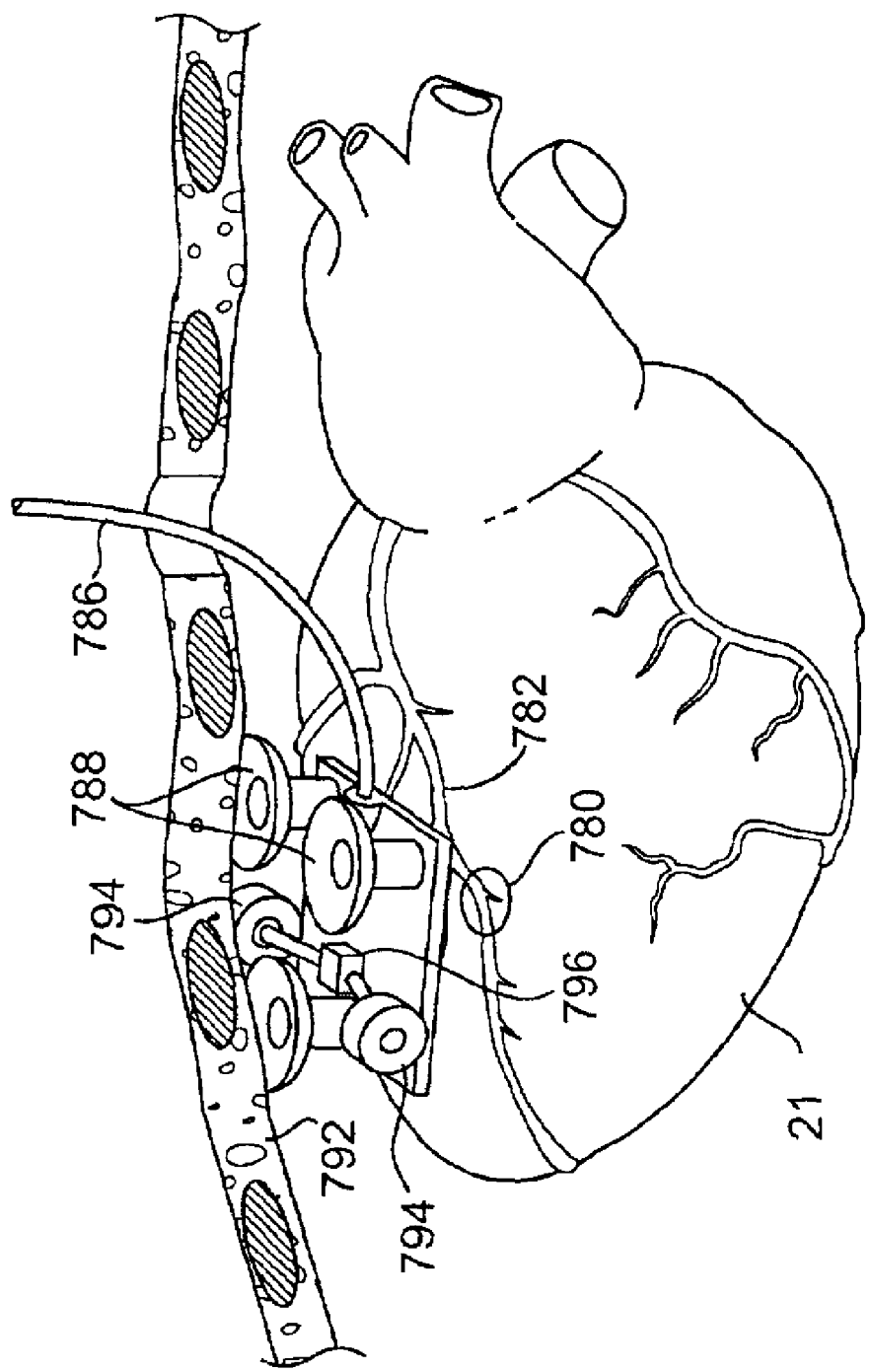
FIG. 58 is a perspective view of another embodiment of the integrated stabilizer.

Referring to FIG. 58, in another embodiment, the integrated stabilizer 704 crawls against the chest wall 792 within the thoracic cavity. The integrated stabilizer 704 includes at least one suction device 788 and a drive system 790. The suction device or devices 788 are positioned on the upper portion of the integrated stabilizer 704, and are configured to engage the chest wall 792. The suction device or devices 788 are connected to a source of low pressure or vacuum via one or more tubes or plenums (not shown) extending from the integrated stabilizer 704 out of the thoracic cavity. The suction device or devices 788 may be one or more suction cups, ports, or other structures adapted to generate suction against the chest wall 792 when a source of lower pressure or vacuum is applied to them. The drive system 790 includes one or more wheels 794 configured to engage the chest wall 792. These wheels 794 have a high coefficient of friction in order to move the integrated stabilizer 704 through contact with the chest wall 794. Alternately, tracks or other mechanisms for delivering motive power may be used instead of wheels 794. The wheels 794 are connected to a motor 796 or other source of motive power via axles 798. The motor 796 may be an electric motor, pneumatic motor, or any other type of motor. For safety, if the motor 796 is electric, it is a low-voltage DC motor. A wire, pneumatic tube or other structure (not shown) extends out of the thoracic cavity to a power source that provides energy to the motor 796. For convenience, such a wire or other structure may be connected to a tether 786 and/or to the tube or plenum through which low pressure or vacuum is communicated to the suction device or devices 788. Alternately, a separate drive system 790 is not used. Rather, a number of suction devices 788 are articulated and configured for individual actuation. By selectively applying suction to the devices 788 and selectively articulating them, the integrated stabilizer 704 can "walk" across the chest wall 792 toward the distal anastomotic site 780.

The linkage 706 is not used in this embodiment. Rather, a tether 786 is connected to the integrated stabilizer 704. However, the linkage 706 or a similar mechanism may be used to place the integrated stabilizer in an initial position within the thoracic cavity. The integrated stabilizer 704 is inserted through the large trocar port 66 with the suction device or devices 788 and the drive system 790 facing upward. This insertion is performed in the direction of the heart 21. The drive system 790 engages the chest wall 792, causing the integrated stabilizer 704 to move relative to the chest wall 792. The operator can then move the integrated stabilizer 704 to the distal anastomotic site 780. The suction device or devices 788 are then actuated, engaging the chest wall 792 and securing the integrated stabilizer 704. Alternately, the suction device or devices 788 are at least partially actuated while the integrated stabilizer 704 is in motion, to assist in holding the drive system 790 against the chest wall 792.

The integrated stabilizer 704 may be sized and shaped to fit securely between the chest wall 792 and the heart 21, such that the integrated stabilizer 704 presses against an area of the heart 21 in which the distal anastomotic site 780 is located. In this way, the distal anastomotic site 780 is stabilized. Alternately, the integrated stabilizer 704 may be thinner, and the distal anastomotic tool and the epicardial dissector (not shown) are connected in a compliant manner to the integrated stabilizer 704 such that they can maintain substantially the same position on the heart 21 as it flexes during normal beating.

Figure 59:
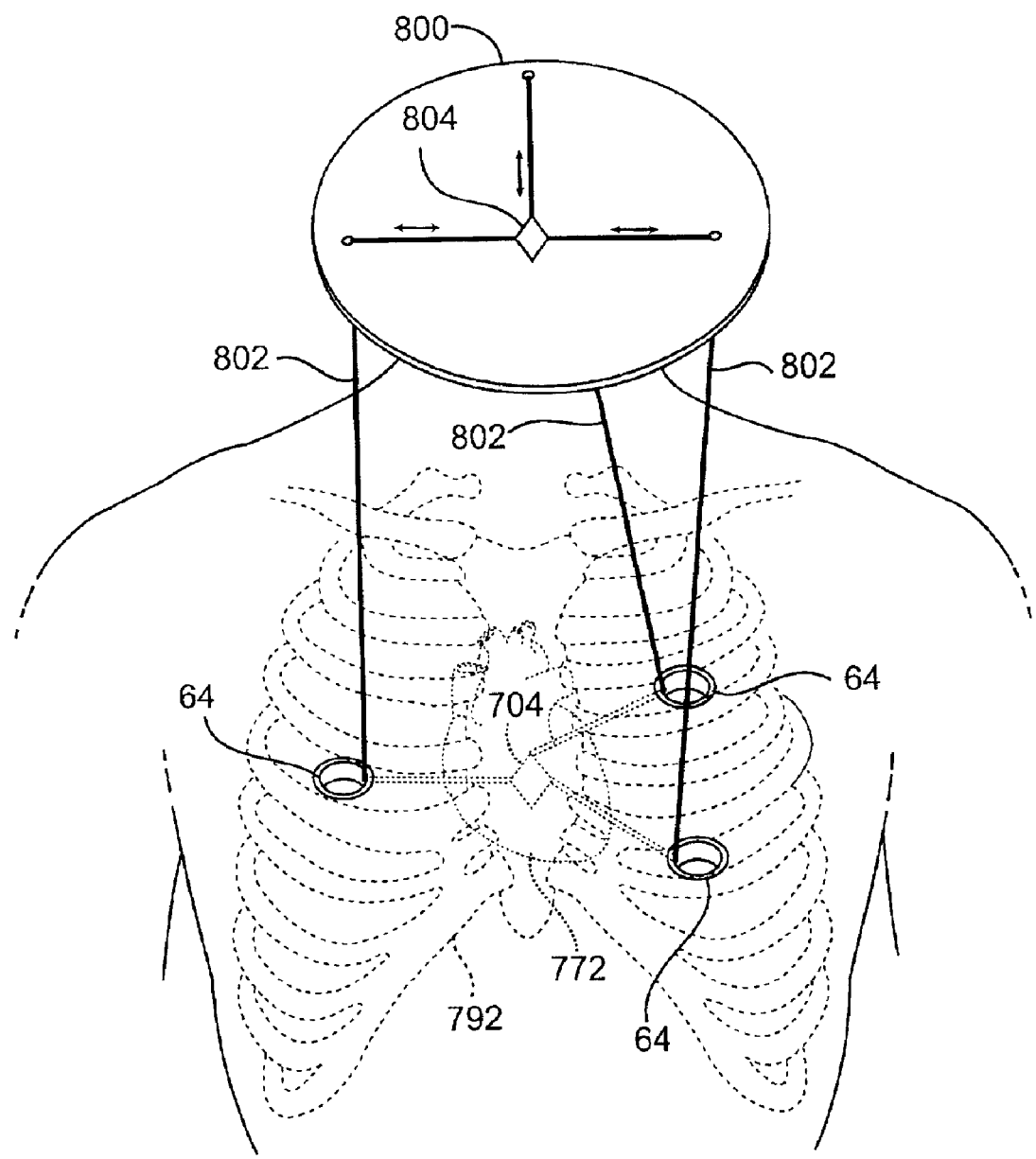
FIG. 59 is a perspective view of another embodiment of the integrated stabilizer.

In another embodiment, referring to FIG. 59, a pantograph 800 is used to adjust the position of the integrated stabilizer 704 relative to the heart 21. For clarity in describing the pantograph 800, the integrated stabilizer 704 is shown schematically. The integrated stabilizer 704 is connected to at least two cables 802, each exiting the chest through a different trocar port 64, 66. Advantageously, three cables 802 are used. The integrated stabilizer 704 is inserted through the large trocar port 66. Then, forceps or other tools are used to pull the cables 802 through the thoracic cavity to the corresponding trocar ports 64,66, and the ends of the cables 802 are pulled out of the trocar ports 64,66. The cables 802 are then connected to the periphery of the pantograph 800. The pantograph 800 is a thin disc-shaped object that may include a model 804 of the integrated stabilizer 704 on it, graspable by the operator. By using a model 804, the operator may be able to better visualize the orientation of the integrated stabilizer 704 within the patient. The pantograph 800 may take a different shape, such as a three-armed frame, each arm extending outward toward one of the trocar ports 64,66. A handle or different structure may be used to provide a place for a user to hold the pantograph 800.

The pantograph 800 is spaced apart from the chest. By tilting the pantograph 800, moving the pantograph 800 toward or away from the chest, and/or by pulling or releasing one or more cables 802 relative to the pantograph 800, the integrated stabilizer 704 can be moved adjacent to the heart 722 and adjusted in the roll and pitch angles as needed to properly interface with the heart 21. The integrated stabilizer 704 may then be secured relative to the heart 21 using clips, suction ports, or any other appropriate structures or mechanisms, such as those described above and below. Alternately, the pantograph 800 can be pulled upward and secured outside the thoracic cavity, in order to hold the integrated stabilizer 704 against the chest wall 792. Alternately, the integrated stabilizer 704 may exert force between the heart 21 and the chest wall 792 to stabilize the myocardium.

Figure 60:
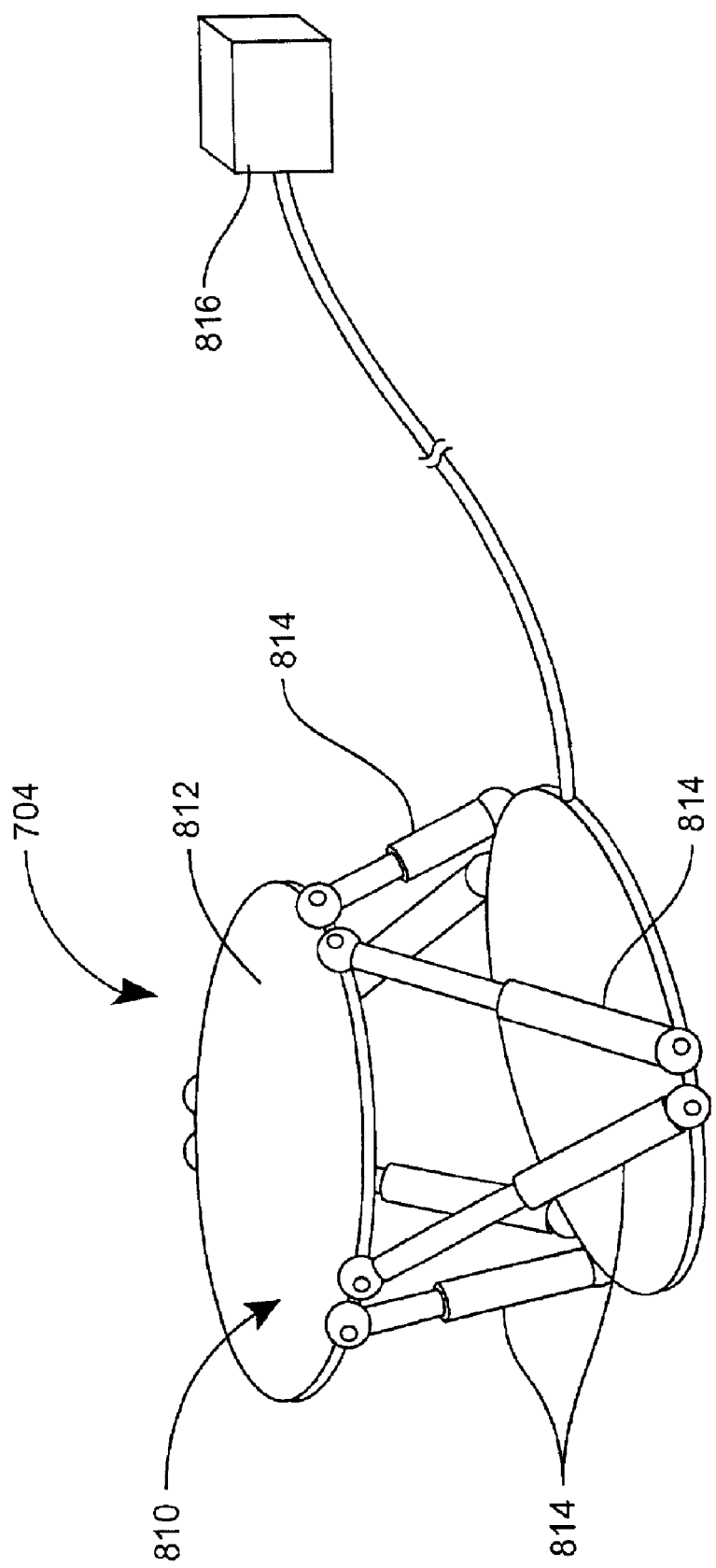
FIG. 60 is a perspective view of another embodiment of the integrated stabilizer.

Referring to FIG. 60, the integrated stabilizer 704 includes a frame 810, where the frame 810 is a Stewart platform. The distal anastomotic tool and epicardial dissector are not shown, for clarity in describing the frame 810. A Stewart platform has six degrees of freedom, and is standard to one skilled in the art. The head 712 of the integrated stabilizer 704 is at the bottom of the frame 810. An upper surface 812 is also part of the frame 810. Instead of a planar upper surface 812, an open structure may be used, analogous to the head 712. The head 712 and the upper surface 812 are connected by struts 814, which are parts of the frame 810. The Stewart platform has two surfaces 712, 812 connected by stiff struts having lengths that can be changed, where the struts 814 connect to the surfaces 712, 812 at flexible joints. The struts 814 are configured to expand and contract axially. If all of the struts 814 expand at once, the head 712 and the upper surface 812 move apart, and the integrated stabilizer 704 expands. If some of the struts 814 expand and others contract or do not move, then the upper surface 812 and the head 712 tilt relative to one another. The struts 814 can be actuated to expand and/or contract based on the pressure of a biocompatible working fluid, such as saline, sealed within them. The struts 814 may be actuated in another manner, if desired. The frame 810 is connected to a controller 816, which itself may be a Stewart platform. The controller 816 allows the operator control over the six degrees of freedom of the frame 810 by actuating the struts 814.

The frame 810 may be positioned over the heart 21 by a tool 710 such as described above, or by another mechanism or structure. Once in place over the distal anastomotic site 780, the operator uses the controller 816 to expand the frame 810 by actuating the struts 814, such that the upper surface 812 engages the chest wall and the head 712 engages the heart 21. The controller 816 may then be used to adjust the pitch and roll angle of the frame 810 to ensure that it is positioned securely and at an appropriate orientation over the distal anastomotic site 780. This adjustment is performed by expanding one or more struts 814 and/or contracting one or more struts 814. An endoscope (not shown) inserted through a small trocar port 64 is used to view the frame 810, allowing the operator to adjust the frame 810 as needed to stabilize the distal anastomotic site 780.

Figure 61:
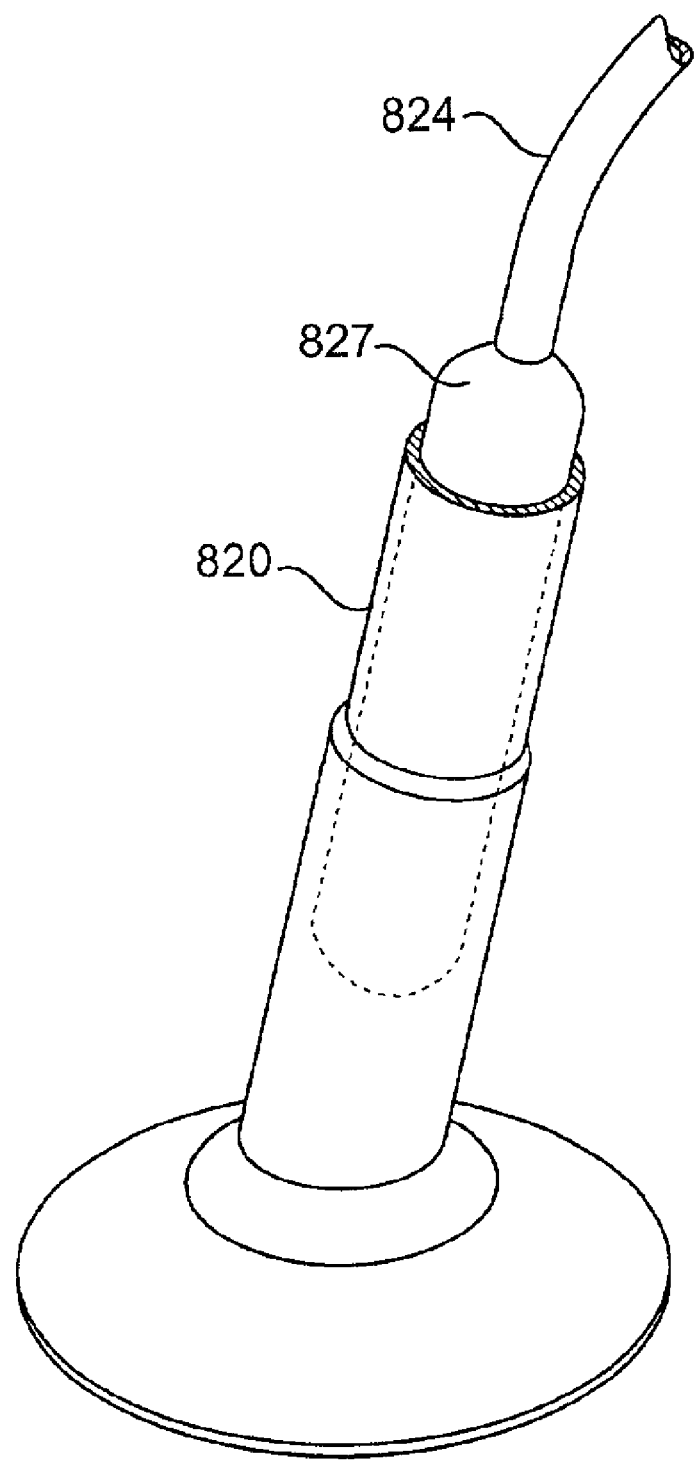
FIG. 61 is a perspective view of an embodiment of a strut that may be utilized in the integrated stabilizer.

Referring to FIG. 61, in another embodiment, the integrated stabilizer 704 includes one or more legs 820. These legs 820 may be components of any of the integrated stabilizers 704 described above, such as the struts 814 described with regard to FIG. Q or the supports 764, 766 described with regard to FIG. H. In this embodiment, each leg 820 includes a balloon 822 within. The legs 820 are substantially rigid, and contain the balloons 822. Expansion of the balloon 822 within a leg 820 causes expansion of the leg 820, and contraction of the balloon 822 within a leg causes contraction of that leg 820. Each leg 820 may be biased toward a contracted position, such that expansion of the balloon 822 acts against that bias to expand the leg 820, and deflation of the balloon 822 permits that bias to contract the leg 820. Each balloon 822 may be connected to a fluid source, such as a saline reservoir or a nitrogen tank, by a tube 824. Fluid for inflation of each balloon 822 is then provided through the tube 824, and conversely fluid is removed from each balloon 822 via the corresponding tube 824 to provide for deflation. By inflating and deflating the balloons 822, the legs 820 are caused to expand and contract, respectively, allowing for expansion and contraction of the integrated stabilizer 704, and adjustment of the angle of the integrated stabilizer 704 relative to the surface of the heart 21.

Figure 62:
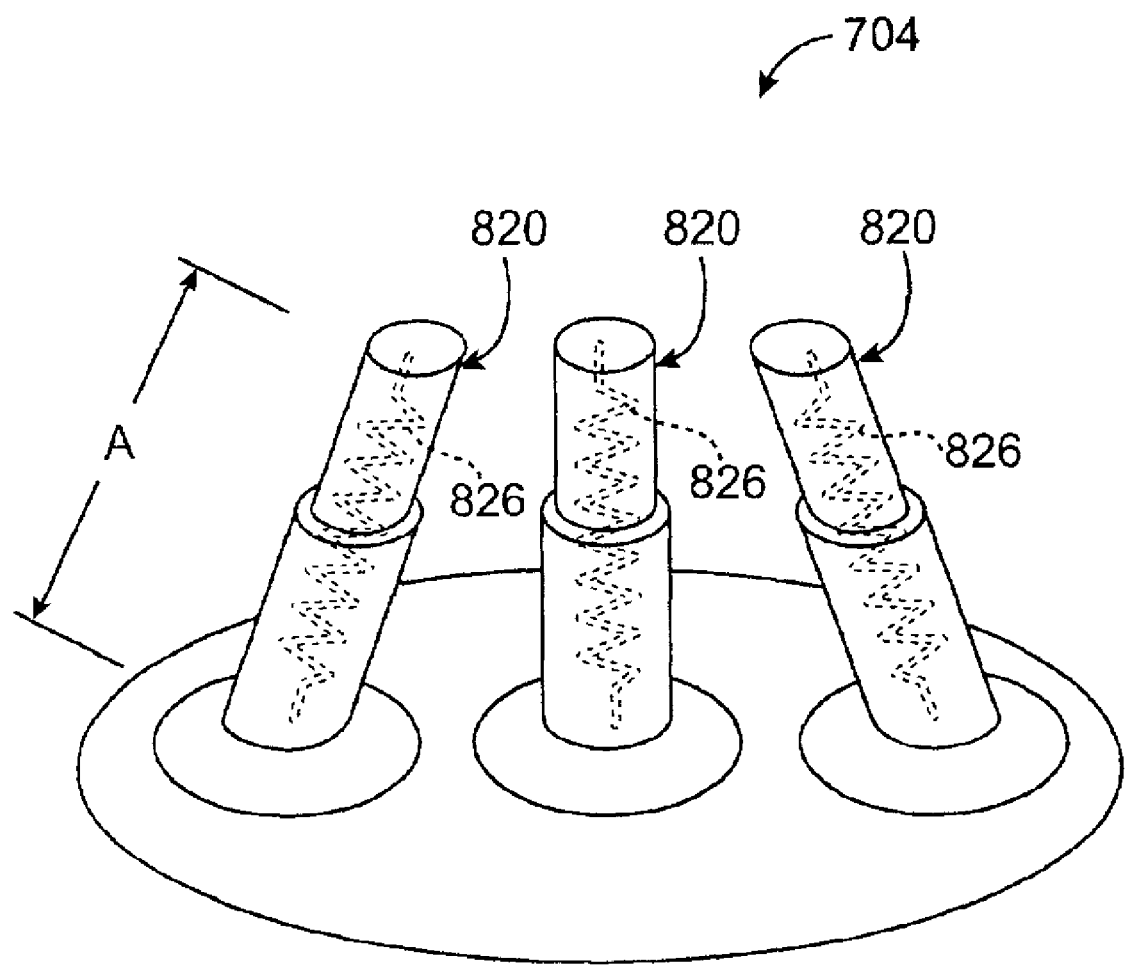
FIG. 62 is a perspective view of another embodiment of strut that may be utilized in the integrated stabilizer.

Referring to FIG. 62, in another embodiment, the integrated stabilizer 704 includes one or more legs 820. These legs 820 may be components of any of the integrated stabilizers 704 described above, such as the struts 814 described with regard to FIG. 60 or the supports 764, 766 described with regard to FIG. 57. The legs 820 are expandable. For example, the legs 820 each may be formed from two coaxial components, one having a diameter larger than the other, into which the other can slide. One or more wires 826 are present inside each leg 820. The wires 826 are constructed from a shape memory material, such as nickel titanium alloy. Other shape memory materials may be used if desired. Further, structures other than wires 826 that are formed from shape memory material may be used. The legs 810 have a first length A. Not all of the legs 810 need have the same first length. Upon application of current or heat to the wires 826, the wires 826 heat up and recover to their initial state, reducing in length and applying force to the legs 820 to shorten them to a second length B. Alternately, the wires 826 expand to their initial state. Not all of the legs 820 need have the same second length. The integrated stabilizer 704 may be inserted into the thoracic cavity when the legs 820 have a shortened second length, in order to facilitate introduction of the integrated stabilizer into the patient. Current or heat is then withdrawn from the wires 826 to allow the legs 820 to expand and position the integrated stabilizer in a desired position relative to the heart.

Figure 63:
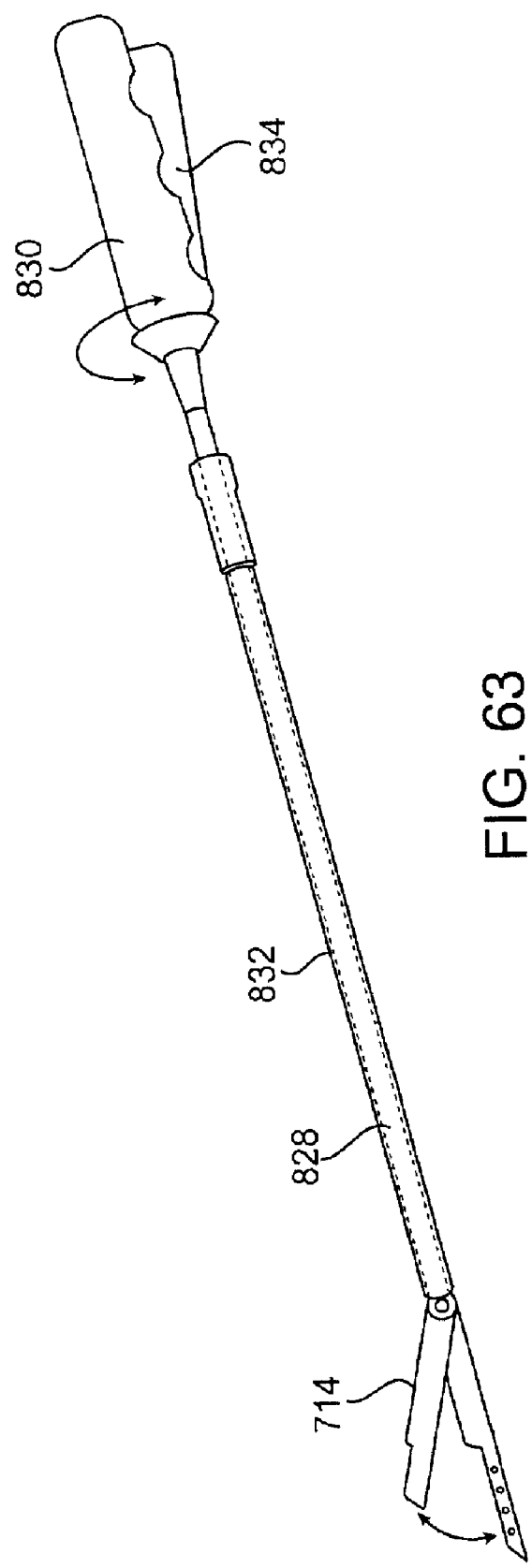
FIG. 63 is a perspective view of an embodiment of an actuator.

Referring to FIG. 63, another embodiment is shown. The distal anastomotic tool 41 is mounted on an arm 828, which in turn is connected to a handle 830. The arm 828 is slidably positioned within a cannula 832. The cannula 832 may be connected to a trocar port 66 or to a frame outside the chest of the patient, in order to provide stability. The arm 828 can slide axially inside the cannula 832, and may be rotated within the cannula 832 by rotating the handle 830. Further, the arm 828 may be configured such that motion of the handle 830 to form an angle relative to the axis of the cannula 832 causes the distal anastomotic tool 41 to form a similar angle relative to the axis of the cannula 832, to provide for precise placement of the distal anastomotic tool 41 at the distal anastomotic site. The handle 830 may include a lever 834 or other mechanism connected to an actuator (not shown) that extends through the arm 828 to the distal anastomotic tool 41. In this way, the distal anastomotic tool 41 may be operated by squeezing or otherwise actuating the lever 834. The actuator may be one or more cables, pushrods, or any other mechanism or mechanisms configured to transmit force from the handle 830 to the distal anastomotic tool 41. The epicardial dissector (not shown) may be connected to a similar arm 828 and handle 830 on a different tool, providing it with adequate freedom to reach the distal anastomotic site and perform dissection. The arm 828 may be stabilized relative to the trocar port (not shown) to provide enhanced accuracy.

Figure 64:
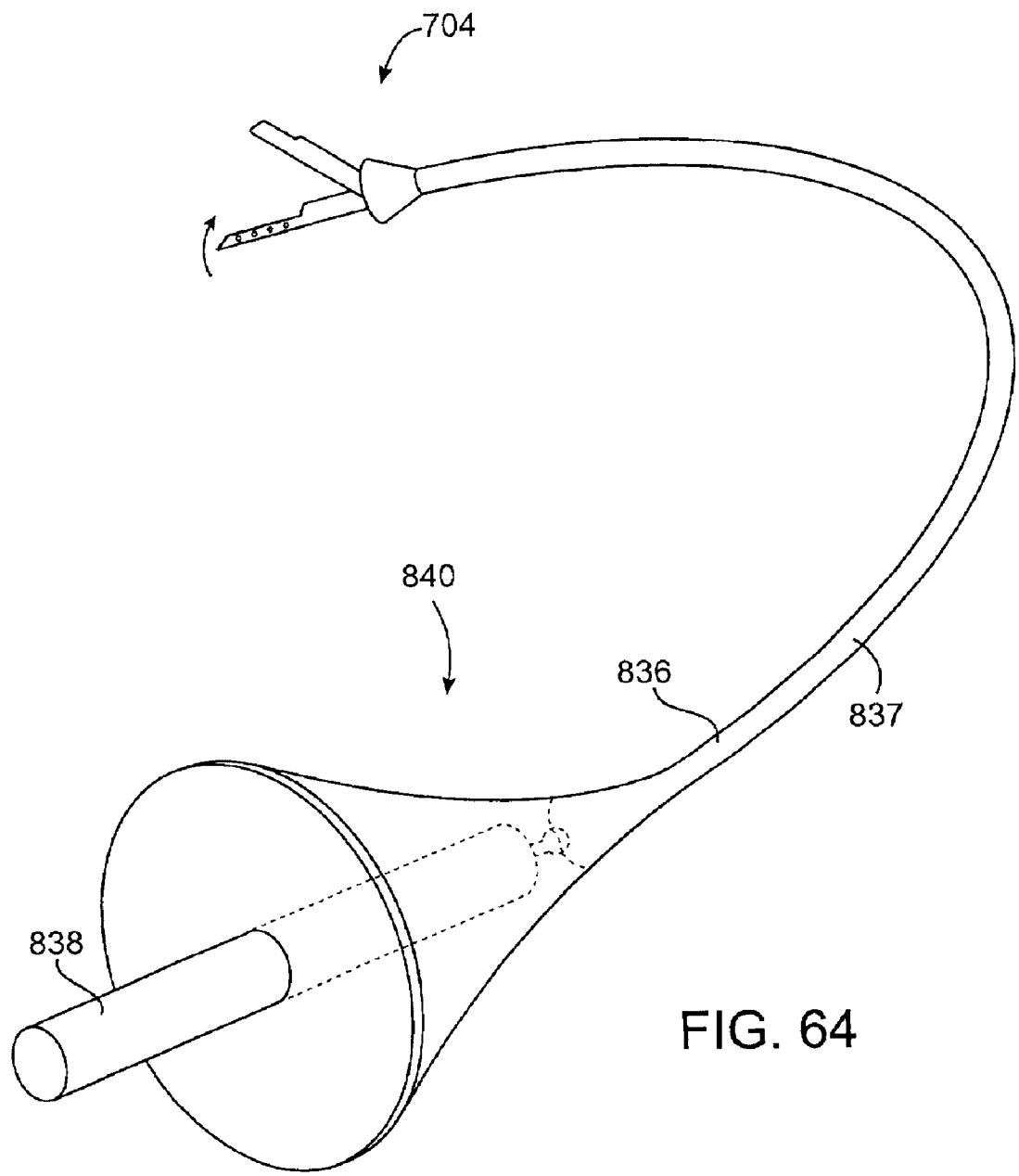
FIG. 64 is a perspective view of another embodiment of an actuator.

Referring to FIG. 64, an embodiment of an actuator 840 is shown. This actuator 840 may be utilized with any of the embodiments of the integrated stabilizer 704 described above. A tube 836 is filled with a biocompatible fluid, such as saline or distilled water. The tube 836 may have a single chamber 837 within it, or a number of different chambers sealed relative to one another. The tube 836 is constructed from a plastic sheet rolled into a tube and heat-sealed. The tube 836 may be manufactured in a different manner, if desired. A handle 838 is connected to the proximal end of the tube 836. The integrated stabilizer 704 is connected to the distal end of the tube 836. Both the handle 838 and the integrated stabilizer 704 are positioned adjacent to one chamber 837 in the tube 836. If a single chamber 837 is used, the handle 838 and the integrated stabilizer 704 are positioned at opposite ends of that chamber. The actuator 840 is operated by compressing the handle 838 into the tube 836, thereby increasing the pressure within the chamber 837. That pressure is communicated through the chamber 837 to the opposite end of the tube 836. This increase in pressure causes the chamber 837 to expand at the opposite end of the tube 836. This expansion may be used to actuate the distal anastomotic tool or epicardial dissector (not shown); to move, expand or contract the integrated stabilizer 704 itself, or to perform one or more other functions. The actuator 840 may be built into another tool, or may be a separate tool connected to the integrated stabilizer 704.

After the integrated stabilizer 704 has been secured relative to the heart, as described above, the epicardium is dissected, if necessary. Once the blockage in the target vessel is located, the surface of the target vessel at the distal anastomotic site can be exposed. In order to expose the coronary artery, the epicardium in the intrapericardial space that covers the coronary artery is incised. The epicardium is dissected away from the distal anastomotic site because it can become trapped between the end of the graft vessel and the side of the target vessel at the distal anastomosis. Current surgical practice involves the use of a beaver blade to dissect the epicardium by hand. This dissection includes two major actions. In the first action, the surgeon slices into the epicardium at and/or adjacent the distal anastomotic site with the edge of the beaver blade substantially parallel to the direction of the cut. In the second action, the surgeon rotates the beaver blade ninety degrees, then uses the beaver blade to retract the tissue from the center of the coronary artery along the incision made in the first action. This is done by moving the beaver blade along the cut with its edge substantially perpendicular to the cut to perform a scraping action. Both the slicing and scraping actions require accurate control of the depth of cut, to prevent cutting through the coronary artery itself.

Figure 65:
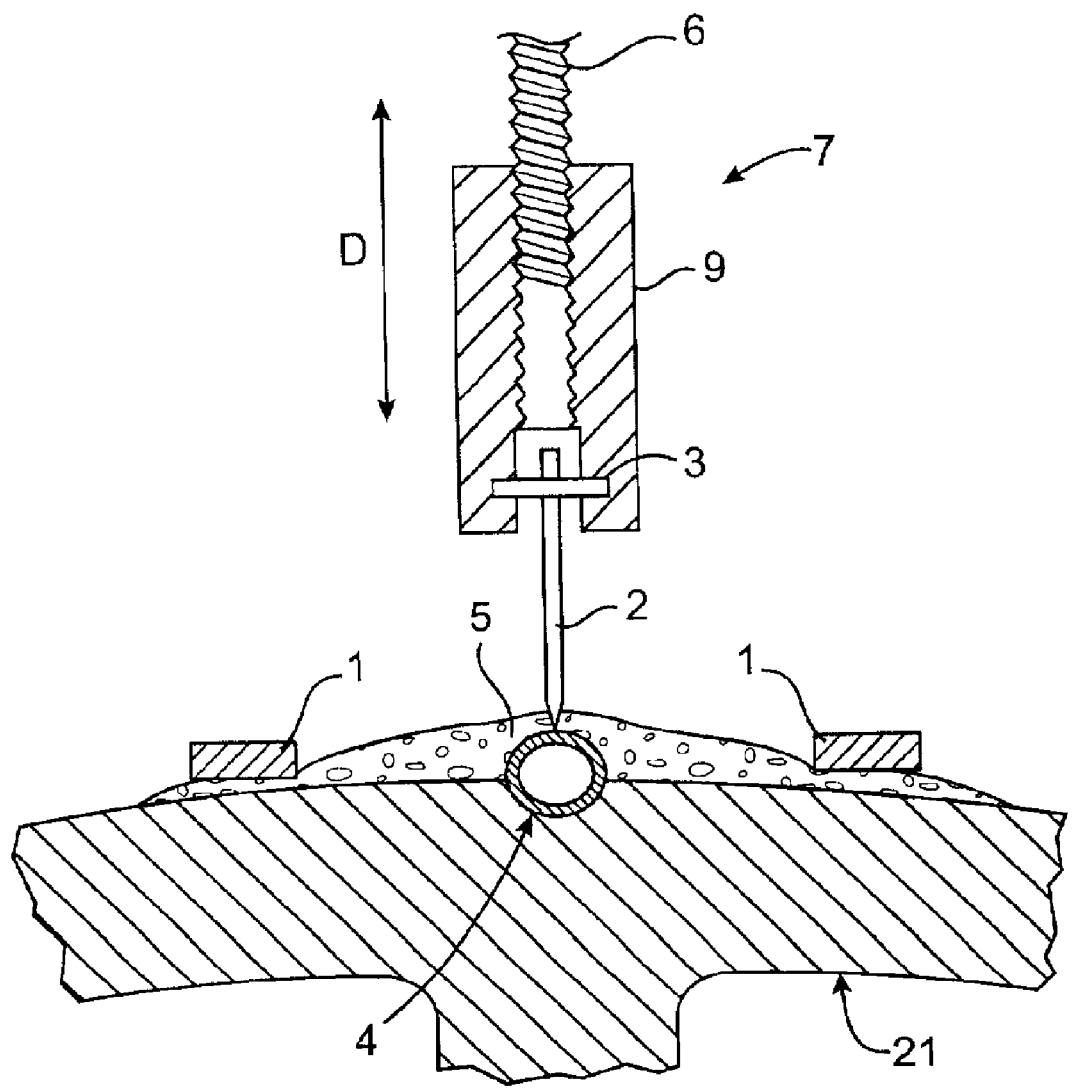
FIG. 65 is a front cross-section view of an epicardial dissector.
Figure 66:
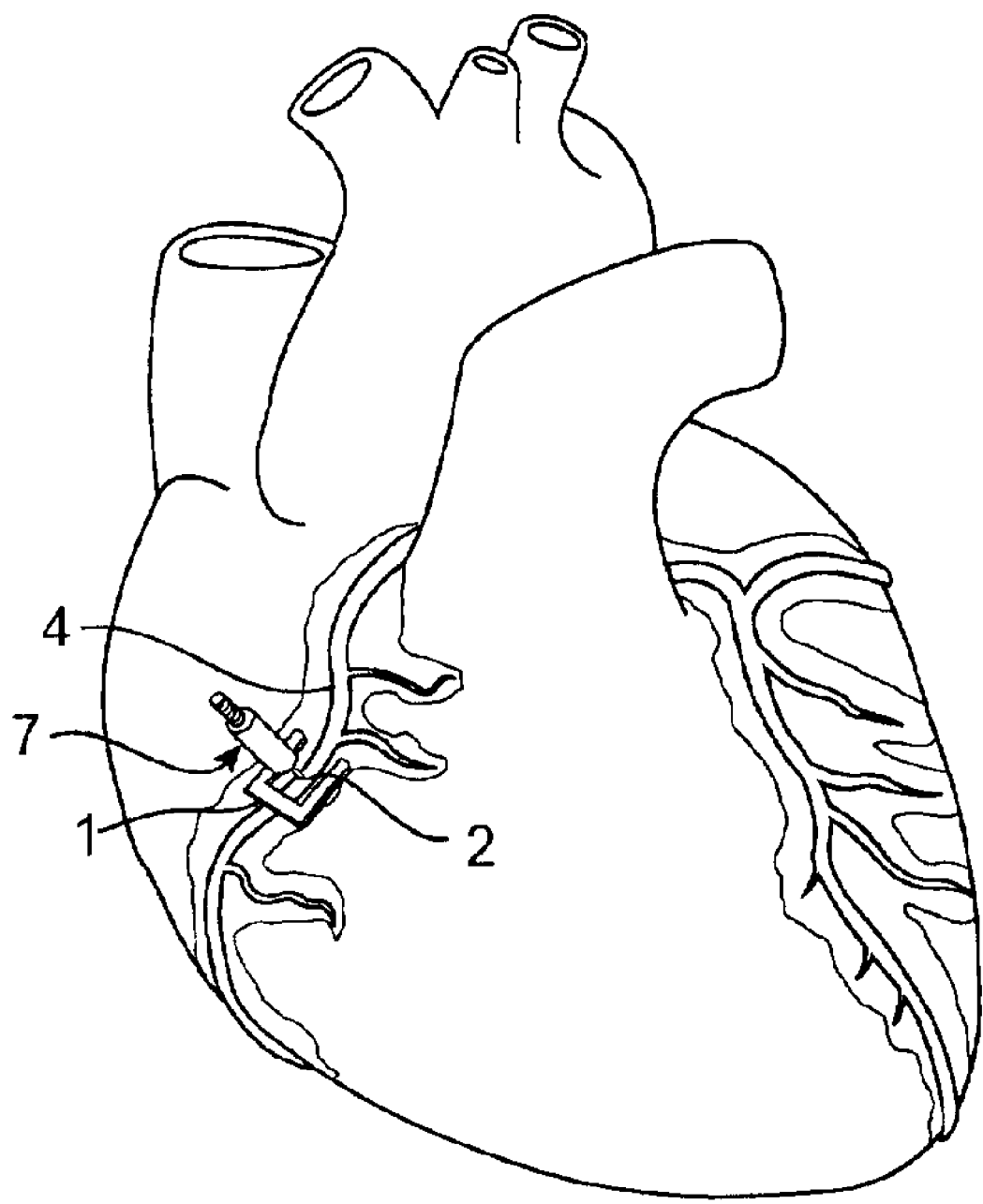
FIG. 66 is a perspective view of the epicardial dissector.

This epicardial tissue can be removed with a scraping tool 7 such the one shown in FIGS. 65–66. Removal of the epicardial tissue may be performed before or after the length of the graft vessel is determined. The scraping tool 7 includes a stabilizer fork 1 and a blade assembly 2. The blade assembly 2 pivots at a point 3 to provide a scraping motion against the myocardial tissue covering the target vessel 4. The blade assembly 2 is mounted such that the it can be moved with respect to the stabilizer fork stabilizer fork in a vertical direction D. As shown, the vertical movement of the blade may be accomplished by a threaded screw 6 that engages a frame 9, where the frame 9 in turn engages the blade assembly 2. Other suitable means may also be employed, however. The blade assembly is also capable of being rotated.

In FIG. 66, the scraping tool 7 is positioned over the target vessel on the surface of the heart, at the distal anastomotic site. As shown, the stabilizer fork 1 is placed in contact with the myocardial tissue surrounding the intended anastomosis site. In FIG. 2 the blade is shown rotated with respect to the target vessel. Initially, however, the blade 2 would be oriented to pivot back and forth in a direction approximately parallel to the direction of the target vessel. In use, the blade 2 is positioned directly above the target vessel 4 in a raised position with the blade moving approximately parallel to the direction of the target vessel. The blade 2 is then moved vertically toward the target vessel and pivoted to dissect the tissue away from the anastomosis site. The blade can be lowered and pivoted repeatedly until the target vessel surface is exposed. The blade can then be retracted, rotated 90 degrees such that the direction of motion of the blade is oriented approximately perpendicularly to the direction of the target vessel 4, and the aforementioned procedure can be repeated to fully expose the surface of the target vessel at the distal anastomotic site. Alternately, the surgeon can dissect the epicardium from the distal anastomotic site by hand using a blade or edge such as a beaver blade.

Referring to FIG. 49, an epicardial dissector 716 is part of the integrated stabilizer 704. The epicardium dissector 716 includes a retractable blade 719, connected to a drive mechanism 717, which is turn is connected to the head 712. The blade 719 is a beaver blade. Alternately, another appropriate type of blade or cutting edge may be used. The drive mechanism 717 moves the blade 719. The blade 719 is positioned close to the distal anastomotic tool 714. The drive mechanism 717 provides enough travel for the blade 719 to allow it to slice through the epicardial layer above a coronary artery over a length of substantially 15 mm. The drive mechanism 717 is connected to a cable (not shown) or other structure or mechanism for receiving operational instructions from the operator. The drive mechanism 717 may be any mechanism useful for moving the blade 719 as needed.

The epicardial dissector 716 has at least three degrees of freedom. The first is in the z-axis, defined as an axis normal to the surface of the heart. Accurate control along this axis is important, to prevent the blade 719 from slicing into the coronary artery at the distal anastomotic site. The total possible travel of the blade 719 along the z-axis is at least 2 mm, substantially accurate to ±0.025 mm. The second degree of freedom is the x-axis, along the coronary artery. The total possible travel of the blade 719 along the x-axis is at least 15 mm, substantially accurate to ±0.25 mm. The third degree of freedom is rotation along the z-axis, which allows the blade 719 to be rotated from a position in which it slices the epicardium to a position in which it dissects the epicardium. The total possible angular motion is at least 90 degrees along the z-axis.

In use, the epicardial dissector 716 is adjusted to be placed over the distal anastomotic site. This adjustment may be made by adjusting the position of the head 712, or by using the drive mechanism 717 to move the blade 719 to a position above the distal anastomotic site. The drive mechanism 717 then rotates the blade 719 to a position in which its cutting edge is substantially parallel to the axis of the coronary artery. The drive mechanism 717 then moves the blade 719 downward into the epicardium, after which it moves the blade 719 in the x-axis along the coronary artery, making an incision in the epicardium. Next, the drive mechanism 717 rotates the blade 719 substantially ninety degrees, such that its cutting edge is substantially perpendicular to the axis of the coronary artery. The drive mechanism 717 then moves the blade 719 along the axis of the coronary artery as needed, to dissect the epicardium above the coronary artery. The blade 719 may be moved slightly toward the coronary artery during the scraping action. Visual observation of the distal anastomotic site through an endoscope is used to control the epicardial dissector 716 and ensure that the coronary artery is not damaged. Optionally, force feedback control may be used.

Figure 67:
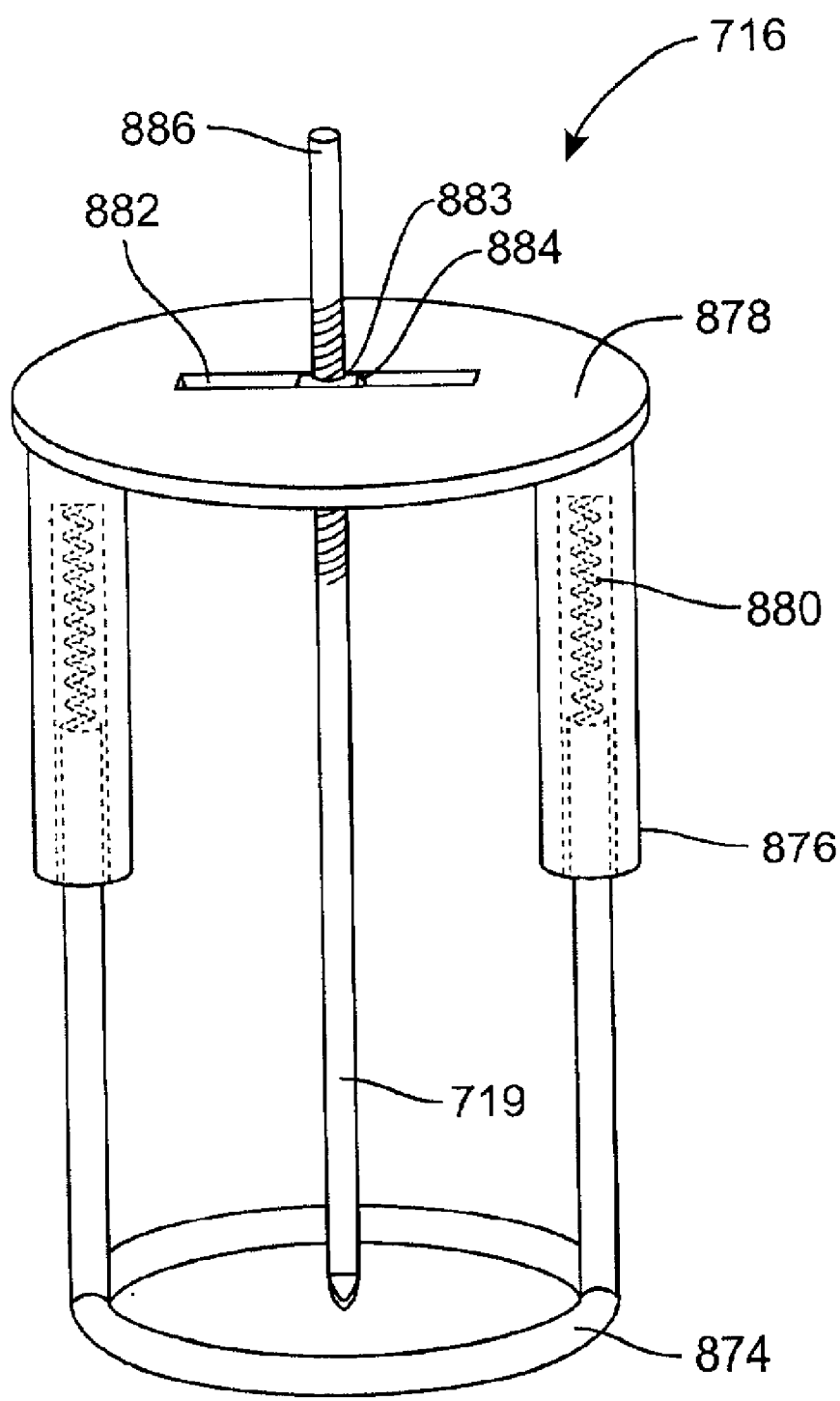
FIG. 67 is a side cross-section view of another embodiment of the epicardial dissector.

Referring to FIG. 67, an embodiment of the epicardial dissector 716 is shown. The epicardial dissector 716 includes a base 874 positioned on the heart at the distal anastomotic site. The base 874 is open in the center, to provide clearance for the blade 719 to access the epicardium. The base 874 is connected to a top 878 via springs 880. The springs 880 bias the base 874 away from the top 878. The springs 880 may be any structure or mechanism configured to bias the base 874 away from the top 878. A slot 882 is defined in the top 878 of the epicardial dissector 716. The blade 719 is connected to a handle 886, which translates through the slot 882 in order to slice open the epicardium. The handle 886 includes a slider 884 that slides within the slot 882. The slider 884 is a substantially cylindrical structure with its axis substantially parallel to the direction of the slot 882, having a threaded hole 883 through it in a direction substantially perpendicular to the axis of the slider 884. The slot 882 has curved walls that are configured both to hold the slider 884 within the slot 882 and allow the slider 884 to translate along the slot 882. The curvature of the walls of the slot 882 holds the slider 884 into the slot, and allows the slider 884 to rotate along its axis. The handle 886 is threaded, such that rotation of the handle 886 in the threaded hole 883 moves the blade 719 up or down relative to the base 874 and thus relative to the heart. Thus, a combination of translation and rotation of the slider 884, and up or down motion of the handle 886, allows the blade 719 to reach a number of positions. In operation, the epicardial dissector 716 is inserted into the patient between the heart and the chest wall before the introduction of the distal anastomotic tool 716. The springs 880 bias the base 874 and top 878 apart, thereby pressing the base 874 onto the surface of the heart and the top 878 onto the inner surface of the chest wall, thereby stabilizing the heart. The surgeon then operates the handle 886 through one of the trocar ports 64, 66. The handle 886 may be grasped with an endoscopic forceps or other tool. If the epicardial dissector 716 is under a trocar port 64, 66, it may extend out of the patient through it, allowing the surgeon to handle it directly. Alternately, the epicardial dissector 716 may be integrated into the integrated stabilizer 704.

Figure 68:
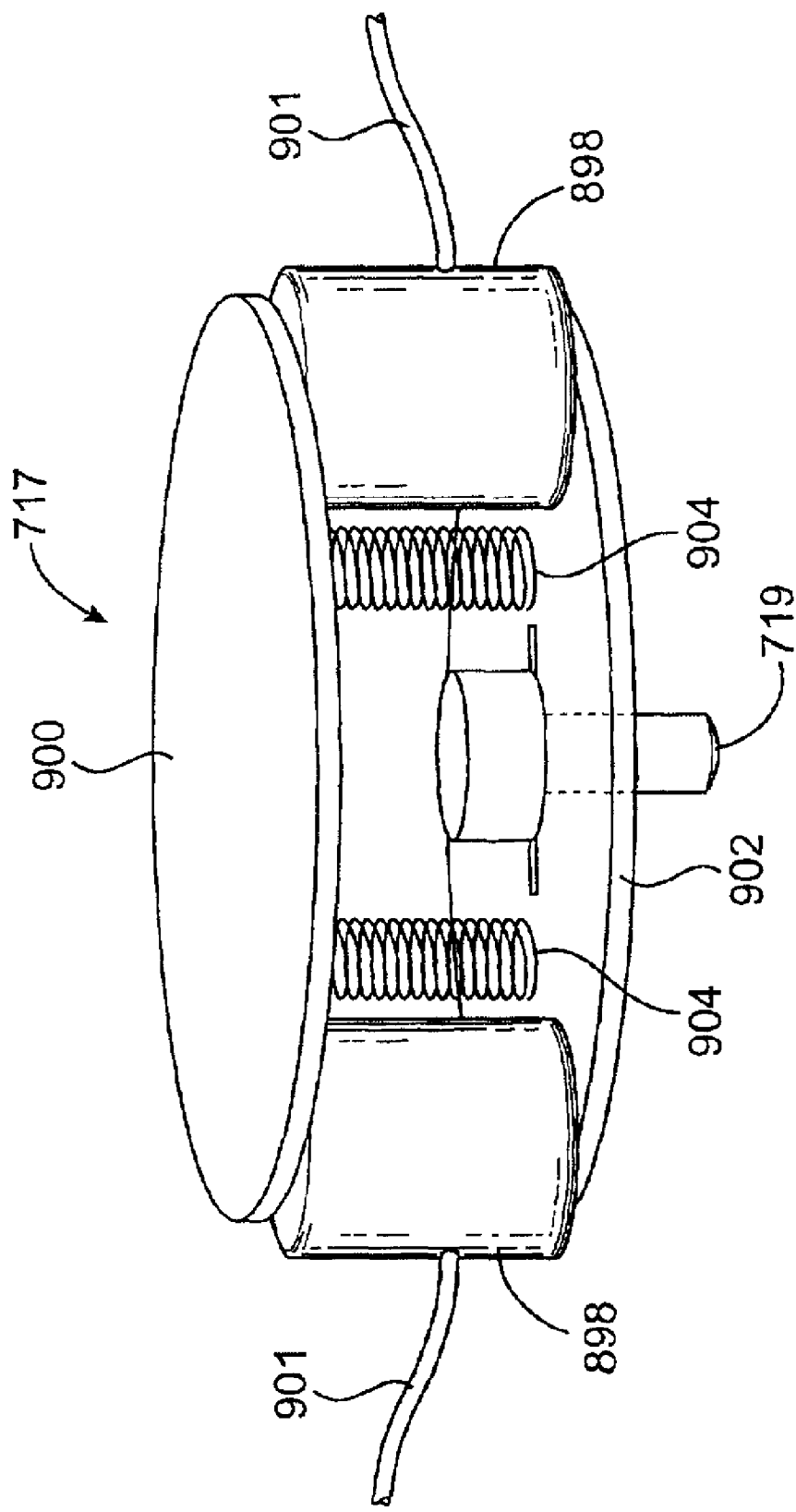
FIG. 68 is a perspective view of another embodiment of the epicardial dissector.

Referring to FIG. 68, another embodiment of the drive mechanism is shown. Control over the height of the blade 719 relative to the heart is performed by inflating and deflating one or more balloons 898. The balloons 898 are connected to a supply of fluid via tubes 901 extending away from the drive mechanism 717 and out of the patient. The balloons 898 are positioned between two surfaces 900, 902 that are connected by springs 904 or other mechanisms that bias the surfaces 900, 902 together. Inflation of the balloons 898 causes the surfaces 900, 902 to separate against the compressive force of the springs 904, and deflation of the balloons 898 causes the surfaces 900, 902 to move closer together under the influence of the compressive force of the springs 904. The blade 719 is mounted to the lower surface 902. Thus, inflating and deflating the balloons 898 causes the blade 719 to move up and down. Further, the selective inflation of different balloons 898 to different levels can tilt the blade 719 as required. The blade 719 is rotatably mounted to the lower surface 719, such that it can be rotated from a slicing position to a scraping position. To slice the myocardium, the drive mechanism 717 can move as a unit along the coronary artery.

Figure 69:
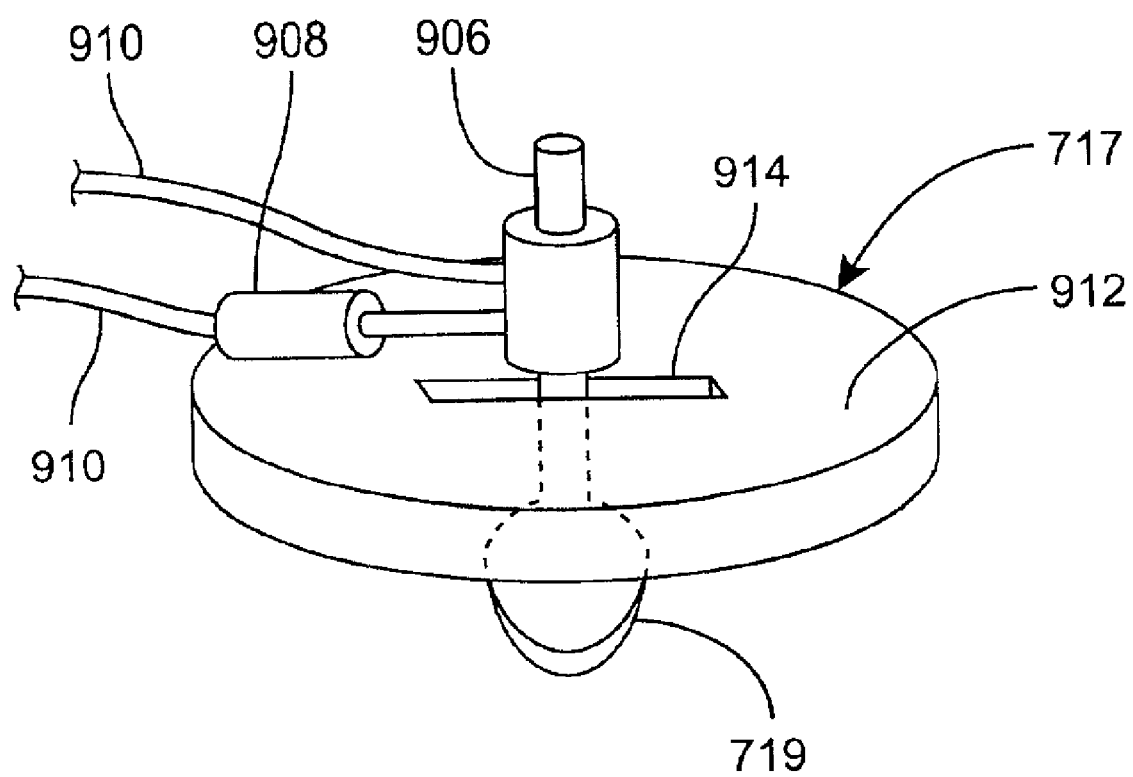
FIG. 69 is a perspective view of another embodiment of the epicardial dissector.

Referring to FIG. 69, another embodiment of the epicardial dissector 716 is shown. The blade 719 is mounted on a first hydraulic cylinder 906, which is positioned to move the blade 719 up and down relative to the heart. The first hydraulic cylinder 906 is also configured to rotate the blade 719, either directly, or via a rotary mechanism (not shown) to which the first hydraulic cylinder 906 is mounted. The blade 719 extends through a slot 914 in a platform 912, where the platform 912 supports the first hydraulic cylinder 906. The second hydraulic cylinder 908 is connected to the first hydraulic cylinder 906, and moves the first hydraulic cylinder 906 itself. Alternately, the blade 719 is also connected to a second hydraulic cylinder 908, which is positioned to move the blade 719 back and forth along the slot. The hydraulic cylinders 906, 908 may be push-pull type, or single-acting with opposing springs. Each hydraulic cylinder 906, 908 is connected to a control device (not shown) outside the patient via hydraulic lines 910 filled with biocompatible fluid. The actuation and control of the hydraulic cylinders 906, 908 is standard. Input to the control device can be stepped down at the epicardial dissector 716 to provide for precise control over the position of the blade 719. For example, 1 cm of movement at the control device can be stepped down to 1 mm of movement at the blade 719, using standard hydraulic techniques.

Figure 70:
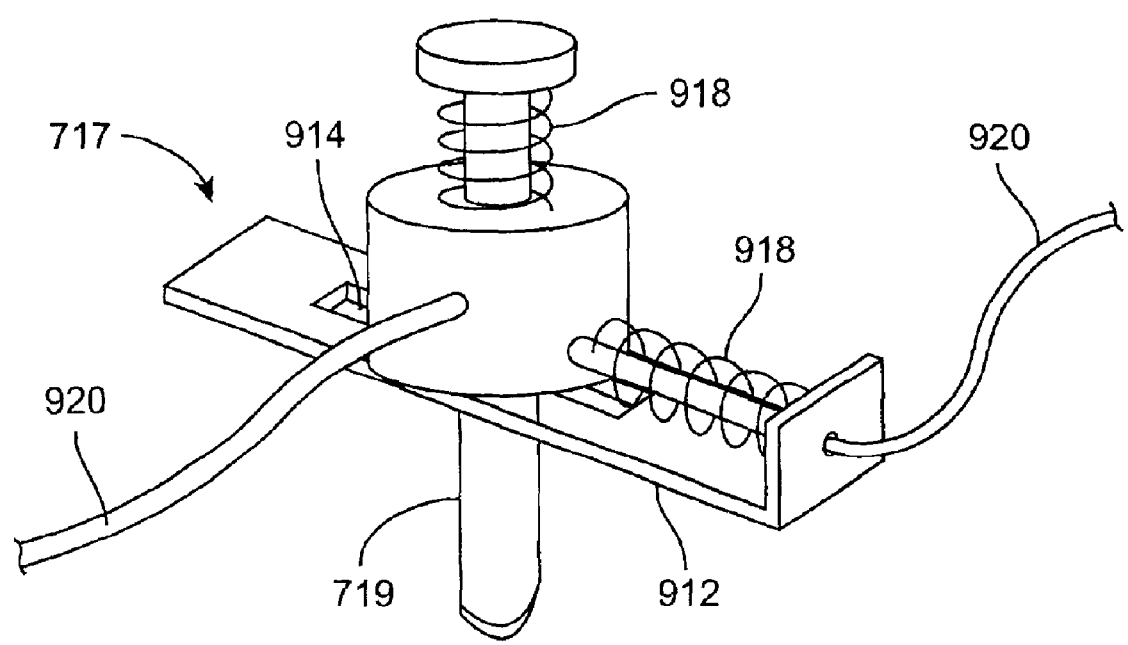
FIG. 70 is a perspective view of another embodiment of the epicardial dissector.

Referring to FIG. 70, another embodiment of the epicardial dissector 716 is shown. This embodiment is similar to that of FIG. 69, where the hydraulic cylinders 906, 908 of that embodiment are replaced by springs 918 and cables 920. The springs 918 may be covered with Dacron or other appropriate material. The spring 918 taking the place of the first hydraulic cylinder 906 is biased upward, and is moved downward along with the blade 719 by tensioning the associated cable 920. In this way, the blade 719 is biased away from the surface of the heart for safety. The spring 918 taking the place of the first hydraulic cylinder 906 is also configured to rotate the blade 719, either directly, or via a rotary mechanism (not shown) to which the spring 918 is mounted. The spring 718 taking the place of the second hydraulic cylinder 908 is biased along one direction of travel along the X-axis, and is moved in the opposite direction along the X-axis by tensioning the associated cable 920. The cables 920 extend out of the patient through one or more trocar ports 64, 66, and may be geared down inside or outside the patient to step down the input to the epicardial dissector 716. In this way, a larger motion of the cable 920 can be converted to a smaller motion of the blade 719. Alternately, the springs 718 are replaced with low-voltage DC solenoids, and the cables 920 are used to transmit low-voltage DC power to them for actuation.

Figure 71:
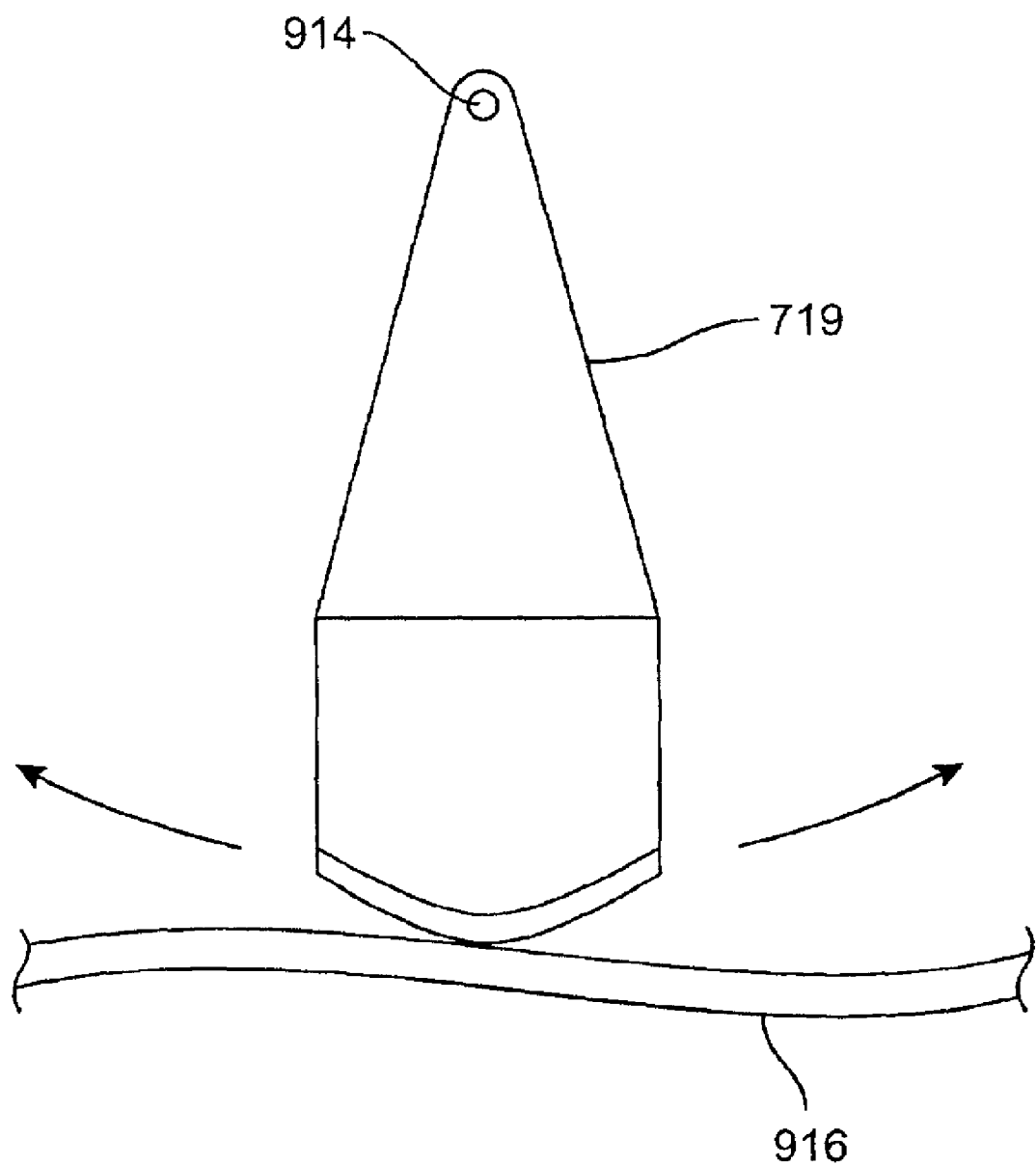
FIG. 71 is a side view of an embodiment of a dissector blade.

Referring to FIG. 71, another embodiment of the epicardial dissector 716 is shown. The blade 719 is connected to a rod 914, where the rod 914 is connected to and driven by the drive mechanism (not shown). The blade 719 is moved into position at the distal anastomotic site over the epicardium 916, and moved downward so that its tip begins to slice the epicardium. The blade 719 is then rotated back and forth about the axis of the rod 914. The blade 719 is shaped such that this rotation slices an appropriate length of the epicardium to the desired depth. The rod 914 is then rotated substantially ninety degrees, and the blade 719 is moved along the incision it created to dissect it further open. The rod 914 may be moved by a linkage (not shown) during or between its motion to perform the slicing and/or scraping actions. Alternately, the rod 914 is not used, and another mechanism is connected to the blade 719 to move it in the appropriate directions.

Figure 72:
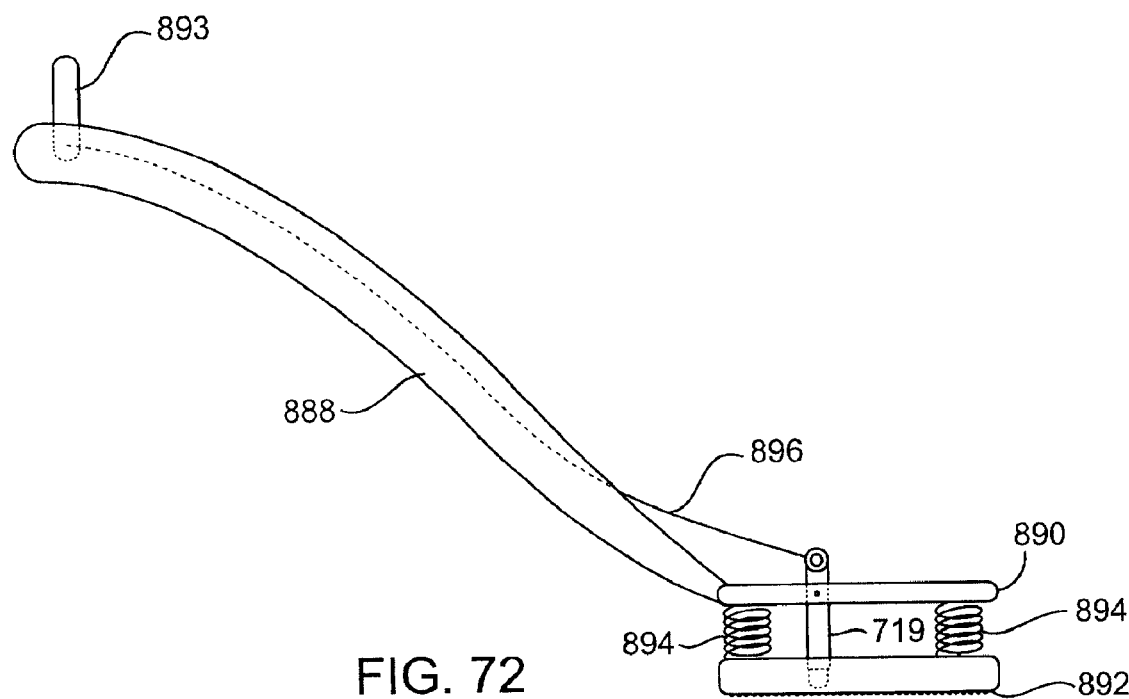
FIG. 72 is a side view of another embodiment of the epicardial dissector.
Figure 73:
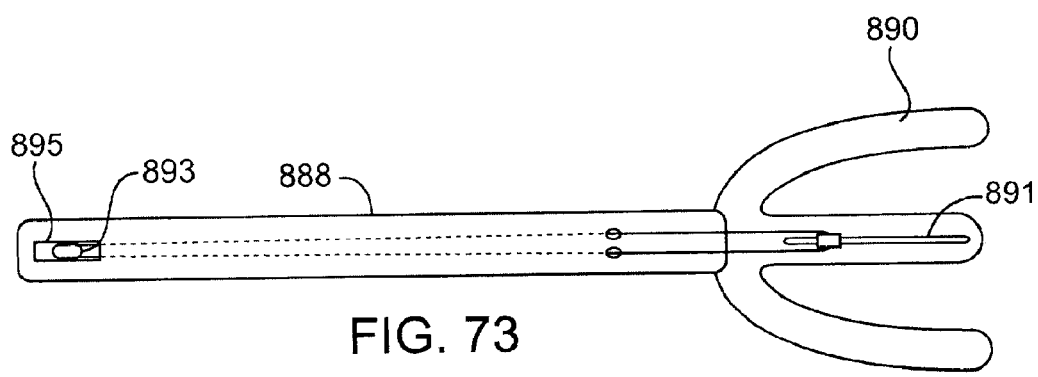
FIG. 73 is a top view of the epicardial dissector of FIG. 72.

Referring to FIGS. 72–73, another embodiment of the epicardial dissector 716 is shown. This epicardial dissector 716 is separate from the integrated stabilizer 704. A handle 888 is connected to a platform 890, and two feet 892 are connected to the underside of the platform 890 via springs 894. The platform 890 is substantially U-shaped, although another shape may be used if desired. The feet 892 extend along both sides of the platform 890, underneath it. The feet 892 may be combined into a single structure, shaped similarly to the platform 890. The underside of the feet 892 may be abrasive, to facilitate steady contact between the feet 892 and the surface of the heart. The feet 892 are placed on the heart such that the distal anastomotic site is between them. The blade 719 is mounted to the platform 890, and extends downward through the platform 890 through a slot 891. The blade 719 may be mounted to the platform 890 in any manner that allows it to move relative to the platform 890 to slice and dissect the epicardium. The springs 894 allow the platform 890 to move up and down relative to the feet 892 and the surface of the heart. Thus, control over the height of the blade 719 is performed manually via controlling the handle 888. Two cables 896 are connected to the blade 719 and/or to a mechanism holding the blade 719. Each cable 896 is substantially the same length, and is connected to a different side of the blade 719. Alternately, the cables 896 may be connected to the blade 719 in another manner. Each cable 896 is connected at its opposite end to a manipulator 893, which is movable within a slot 795. By pulling or tensioning one cable 896, the blade 719 is rotated. Thus, the orientation of the blade 719 can be changed between slicing and scraping operations. By pulling or tensioning both cables 896, such as by moving the manipulator 893 along the slot 895, the blade 719 is moved relative to the platform 890. Depending on the manner in which the blade 719 is connected to the platform 890, the blade 719 may rotate about a fixed point in order to slice the epicardium, or may translate along at least a portion of the slot 891 in the platform 890. In another embodiment, the handle 888 is eliminated, and the remaining components of the epicardial dissector 716 are mounted to the head 712. In such an embodiment, the cables 896 are threaded through the linkage 706 connected to the head 712, or otherwise routed out of the patient through a trocar port 64, 66.

Figure 74:
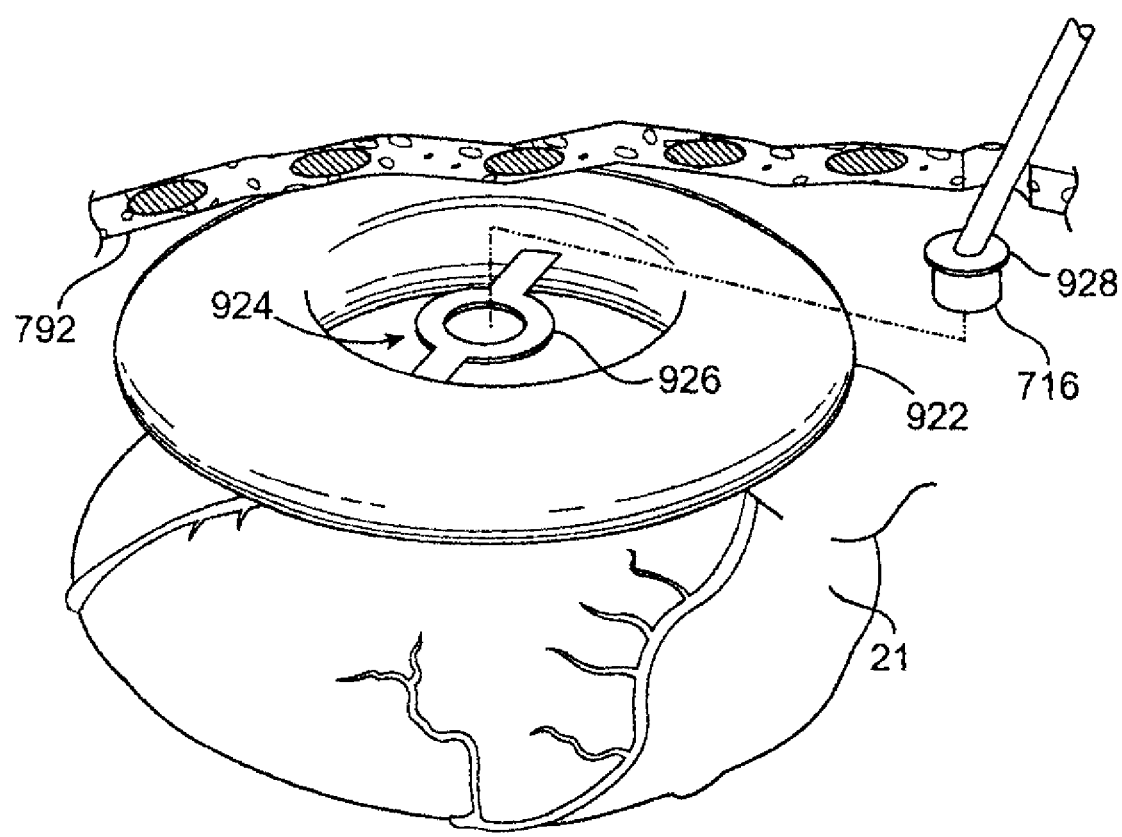
FIG. 74 is a perspective view of an epicardial dissector and a tool for placing it at the distal anastomotic site.

Referring to FIG. 74, a balloon 922 for holding an epicardial dissector 716 is shown. The balloon 922 may be a part of, or separate from, the integrated stabilizer 704. The balloon 922 is inflated between the heart 21 and the chest wall 792. The balloon 922 is toroidal, and includes a dissector receiver 924 in its center. The dissector receiver 924 may be fixed relative to the balloon 922, or slidable relative to the balloon 922 through ports (not shown) in its walls. The dissector receiver 924 includes a center piece 926 having a hollow center, through which the epicardial dissector 716 is slid after the distal anastomotic site is stabilized. The hollow center of the center piece 926 is substantially circular. Alternately, the hollow center of the center piece 926 may take a different shape, such as a circular shape having a registration feature, or an oval shape. A collar 928 extends outward from the upper portion of the epicardial dissector 716. The collar 928 is sized to be larger than the hollow center in the center piece 926, such that contact between the collar 928 and the center piece 926 stops the downward motion of the epicardial dissector 716. The use of this balloon 922 and center piece 926 to receive an epicardial dissector 716 is compatible with the epicardial dissectors 716 described in this document, as well as other structures and mechanisms for epicardial dissection.

Once the distal end of the graft vessel is in position at the desired anastomosis site, the distal anastomosis procedure can be performed. The method includes inserting an anvil into a target vessel at an intended anastomosis site, supporting a wall of the target vessel at the intended anastomosis site with the anvil positioned adjacent an interior of the wall, performing an anastomosis, and removing the anvil. The distal anastomotic tool 41 and a method for performing the distal anastomosis are described below with reference to FIGS. 75–80.

Figure 75:
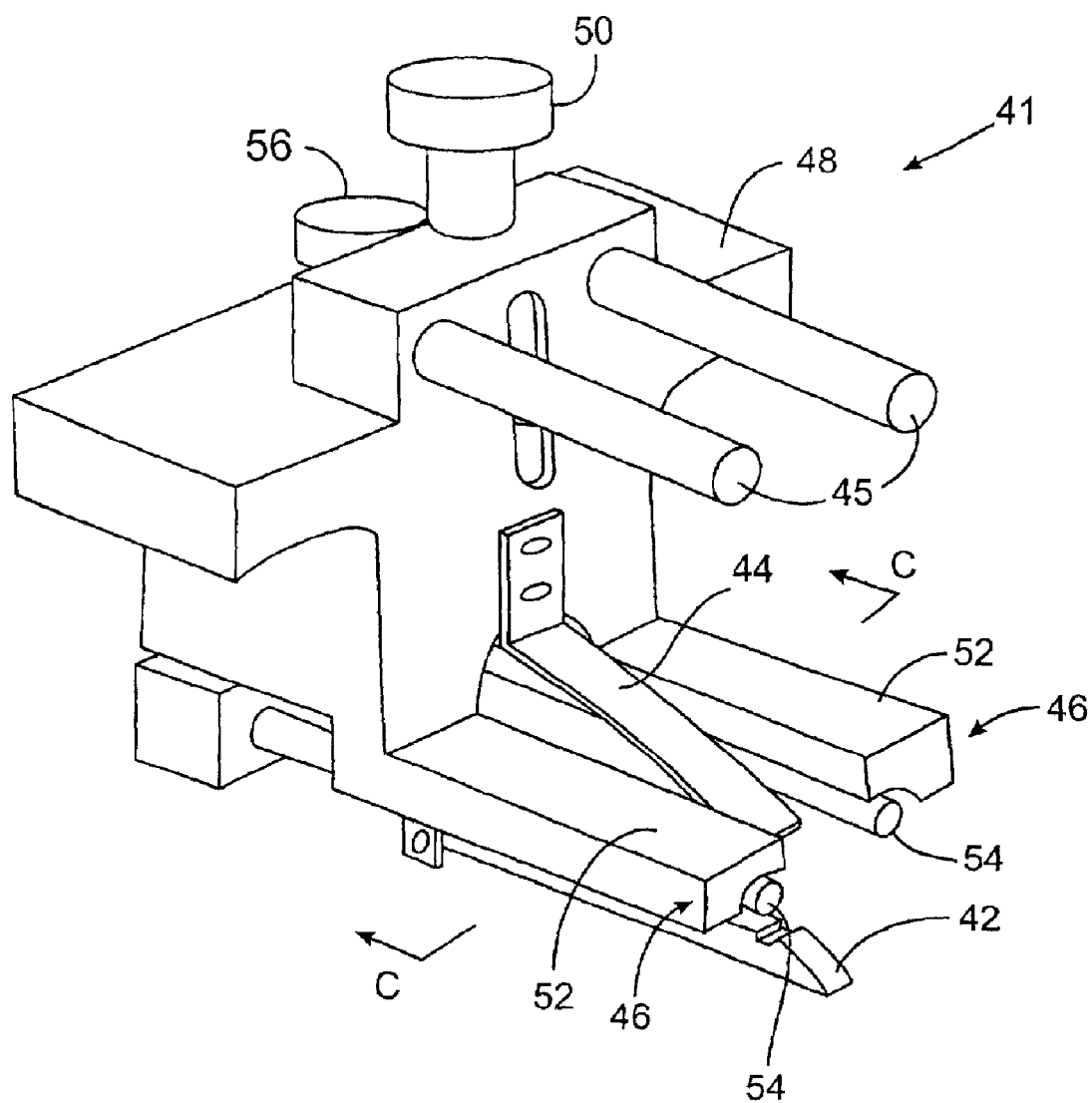
FIG. 75 is a perspective view of a distal anastomotic tool for handling the distal end of a graft vessel.

FIG. 75 shows a distal anastomotic tool 41 for controlling a tissue site and performing the distal anastomosis. The distal anastomotic tool 41 includes an anvil 42, a cutter 44, alignment pins 45, and a graft vessel holder 46 all mounted on a handle 48. The anvil 42 is connected to an actuator 50 which allows the anvil to be moved downward against the bias of a spring inside the handle 48. The cutter 44 may be spring biased or fixed and is positioned on the handle 48 directly above the anvil 42. The graft vessel holder 46 includes two fixed arms 52 and two movable arms 54. The two movable arms 54 are connected to a second actuator 56 on the handle 48. Depression of the second actuator 56 against the bias of a spring within the handle 48 causes the movable arms 54 to be moved downward away from the fixed arms 52 to receive portions of the graft vessel 46 between the movable arms 54 and the fixed arms 52. The distal anastomotic tool 41 also includes a staple holder and staples which have been omitted from FIG. 75 for purposes of clarity. The anvil 42 can be provided with several staple bending features (not shown) such as a plurality of recesses which receive the ends of staples and cause the staple ends to bend over.

One example of an anvil 42 has a height and a width of about 2 mm or less, preferably about 1 mm or less, and a length of about 2 to 15 mm, preferably 5 to 12 mm. The length of the anvil will vary depending on the diameter of the graft vessel. Preferably, a length to width ratio of the anvil arm 14 is between 2:1 and 15:1.

Figure 76:
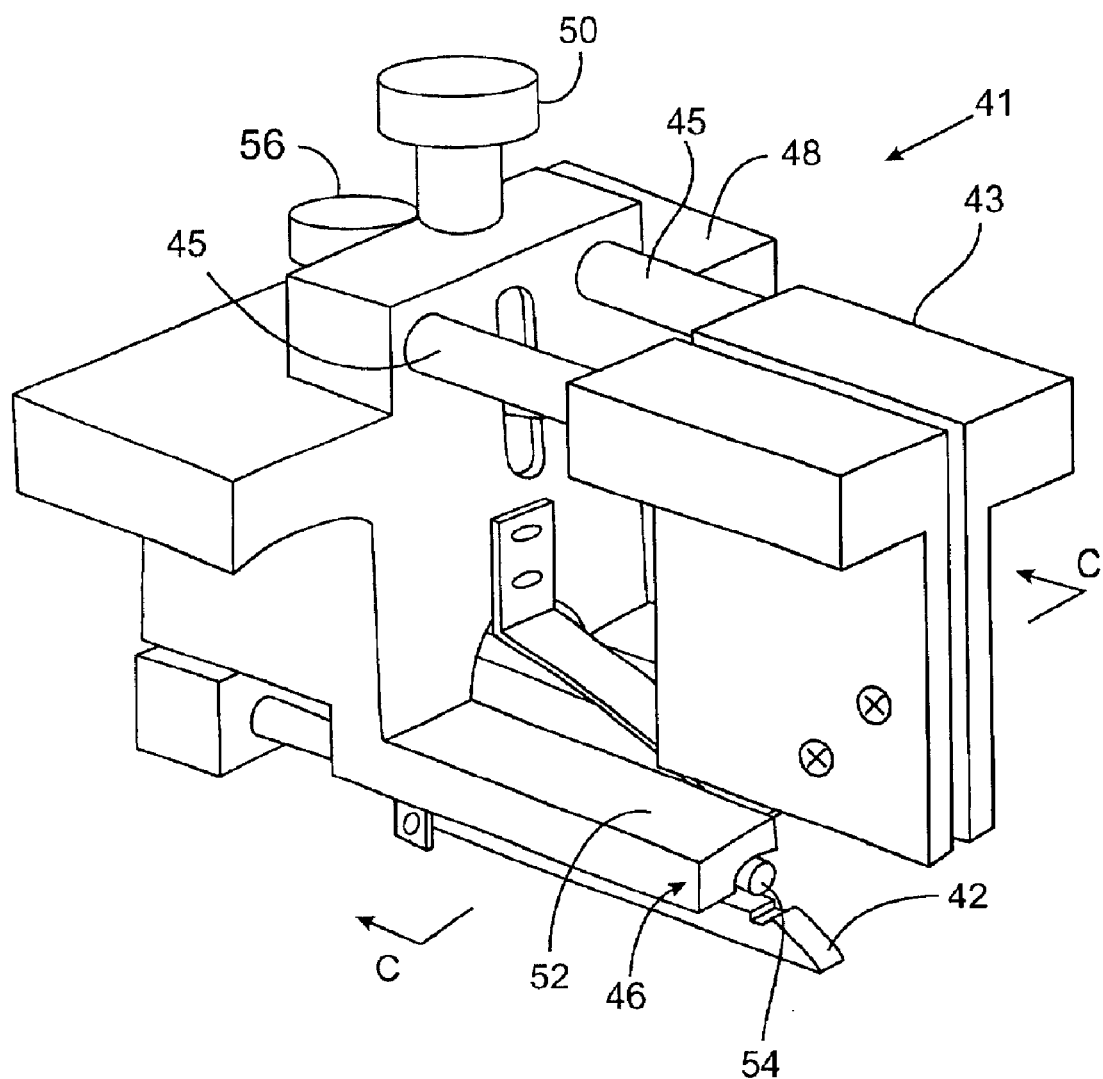
FIG. 76 is a perspective view of a graft vessel/clamp assembly being mounted on the distal anastomotic tool.
Figure 77:
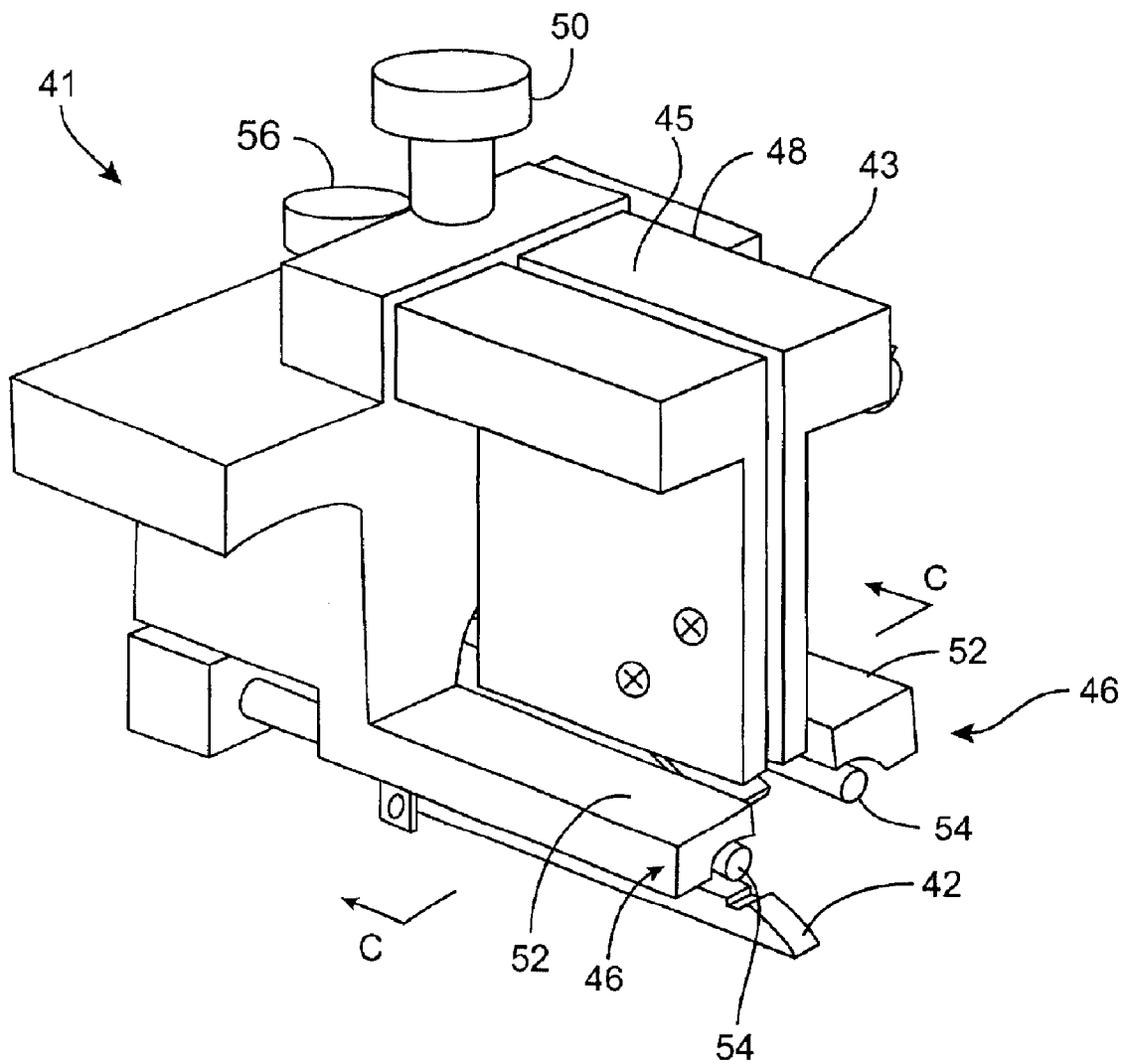
FIG. 77 is a perspective view of a graft vessel/clamp assembly mounted on the distal anastomotic tool.

As described above, the head 712 of the stabilizer produces tension, also referred to as countertraction, on the epicardium. The target vessel at the distal anastomosis site is thus tensioned as well. This tension is advantageous for performing the distal anastomosis. FIGS. 76–77 illustrate the insertion of a clamp/graft vessel assembly 43 onto the distal anastomotic tool 41. The graft vessel 30 has been omitted from FIGS. 76–77 for purposes of clarity. Referring also to FIG. 14, after the graft vessel (not shown) is sliced, the clamp/graft vessel assembly 43 is removed from the graft vessel preparation device and attached to the distal anastomotic tool 41 via alignment holes 122 that mate with the corresponding alignment pins 45 on the distal anastomotic tool 41. The pins 45 each slide into the corresponding alignment holes 122. The assembly 43 may be connected to the distal anastomotic tool 41 with endoscopic forceps. Alternately, other tools could be used to connect the assembly 43 to the distal anastomotic tool 41. For example, a guidewire connected to the assembly 43 and the distal anastomotic tool 41 may draw them together. As another example, one or more magnets on the assembly 43 correspond to one or more magnets on the distal anastomotic tool 41, facilitating the connection between them.

Figure 78:
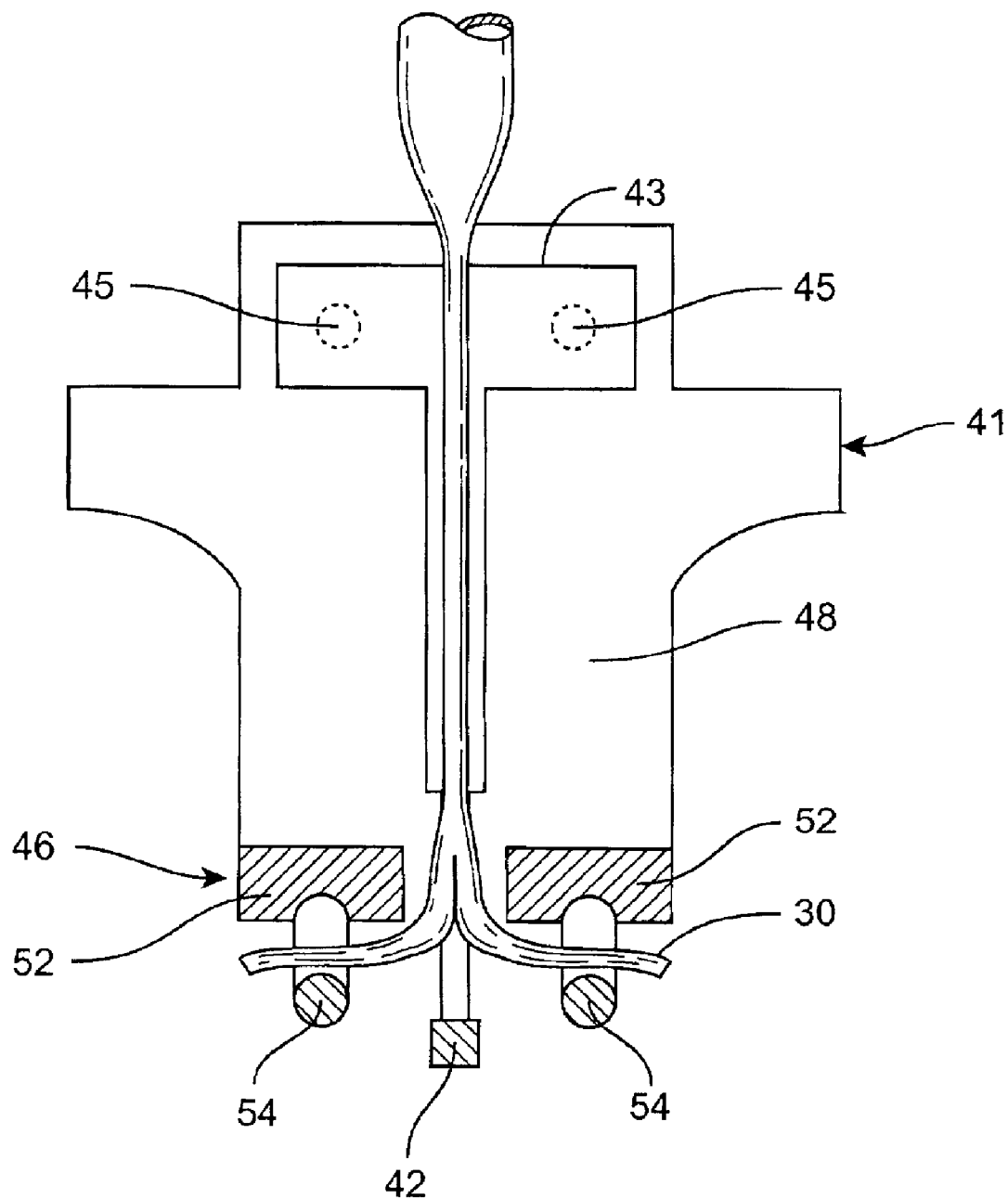
FIG. 78 is a cross sectional view taken along line C—C of FIG. 77, showing a first step of the anastomosis procedure at the distal end of a graft vessel.

As shown in FIG. 78, the free end of the graft vessel 30 has been split to form two flaps which can be held by the graft vessel holder 46. In order to mount the clamp/graft vessel assembly 43 on the distal anastomotic tool 41, the first actuator 50 and the second actuator 56 are depressed to move the anvil 42 and the movable arms 54 downward. The clamp/graft vessel assembly 43 is then attached to the distal anastomotic tool 41 such that the graft vessel flaps are inserted between the fixed and movable arms 52 and 54. Once the clamp/graft vessel assembly 43 is attached to the distal anastomotic tool 41, the vascular anastomosis procedure can be performed. The clamp/graft vessel assembly 43 may be attached to the distal anastomotic tool 41 before dissecting the myocardium, if desired.

Figure 79:
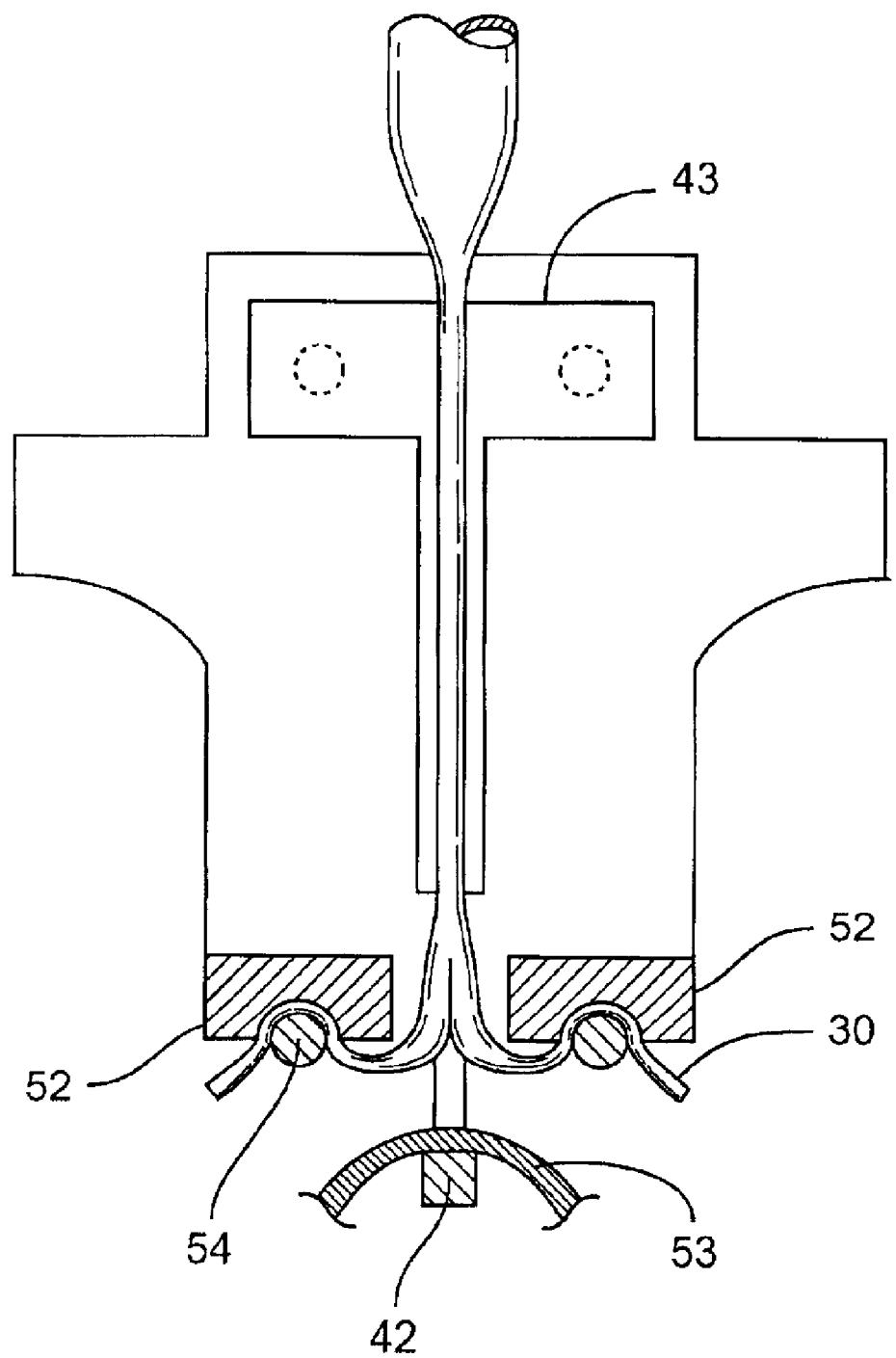
FIG. 79 is a cross sectional view taken along line C—C of FIG. 77, showing a second step of the anastomosis procedure.
Figure 80:
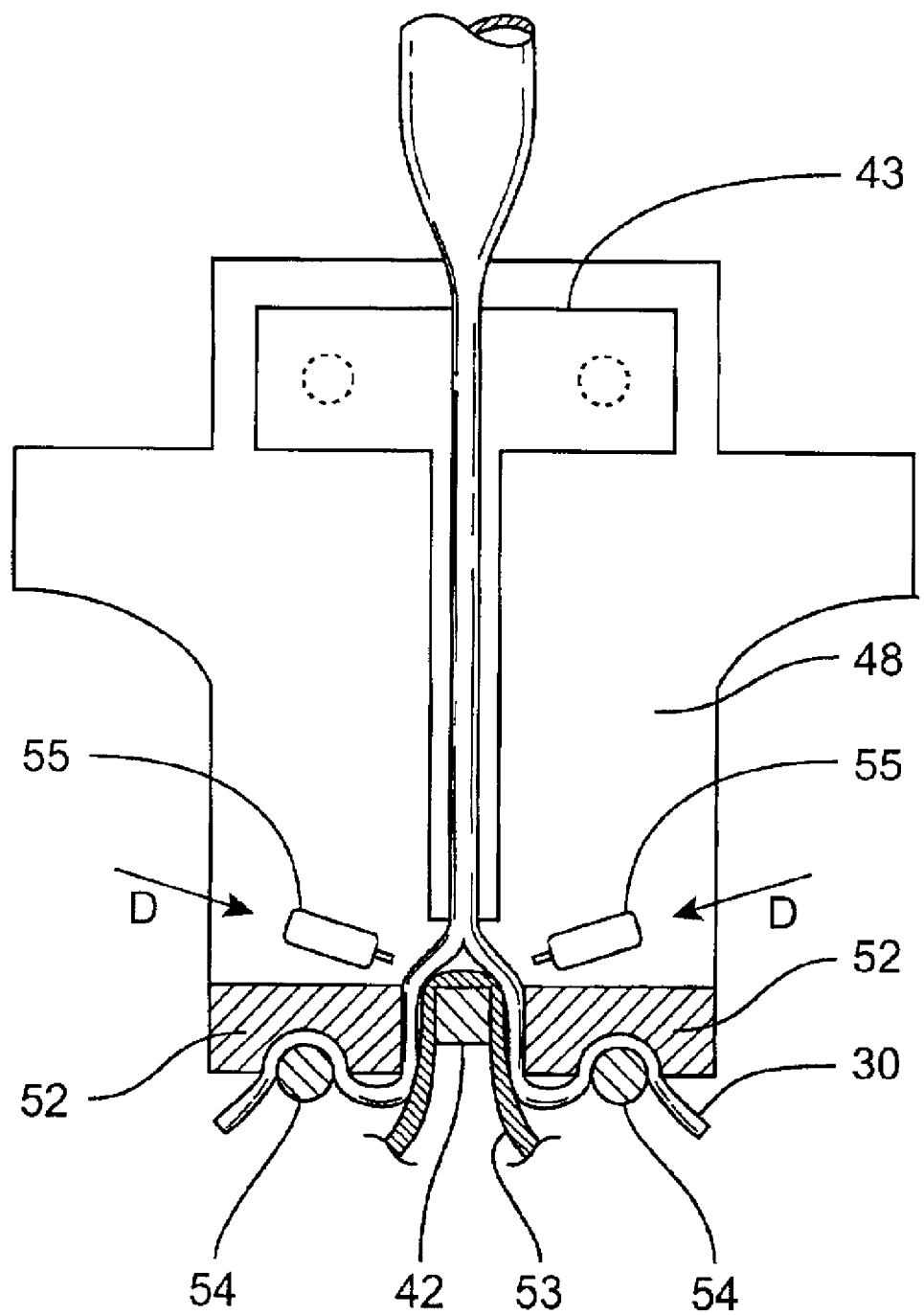
FIG. 80 is a cross sectional view taken along line C—C of FIG. 77, showing a third step of the anastomosis procedure.

The second actuator 56 is then released to trap flaps of the graft vessel, as shown in FIG. 79. The anvil 42 is then inserted into the target vessel 53. Once the anvil has been inserted in the target vessel 53, the actuator 50 is released to allow the anvil 42 and the clamp/graft vessel assembly 43 to move closer to one another to tension the wall of the target vessel. FIG. 80 illustrates the tensioned target vessel 53 positioned adjacent the split and trapped graft vessel 30 in a position for performing anastomosis. The tensioned target vessel 53 is stabilized by the anvil 42. The staple holders 55 are then advanced in the direction of the arrows D toward opposite sides of the anvil 42 to staple the graft vessel 30 and target vessel 53 together. Once the staples have been placed, the anvil 42 is withdrawn from the target vessel 53 between adjacent staples. The withdrawal of the anvil 42 leaves a gap which is approximately the same as the spacing between adjacent staples. Accordingly, minimal blood leakage occurs at the location where the anvil arm has been withdrawn. After stapling is complete, an incision is formed in the wall of the target vessel 53 to allow blood flow between the target vessel and the graft vessel 30. The incision can be made either before or during removal of the anvil 42. The graft and target vessels can also be secured together using a plurality of clips or other mechanical fastening means rather than staples.

In one embodiment, referring as well to FIG. 49, at least one cam path 846 is defined in an inner surface 848 of the head 712. A corresponding at least one cam follower (not shown) extends out of the distal anastomotic tool 41 into the cam path 846. The pathway of the distal anastomotic tool 41, and hence the anvil 402, is controlled by this cam path 846. Thus, the cam path 846 is shaped to control the approach, penetration, and insertion of the anvil 42 relative to the target vessel, by controlling its orientation and position. The cam path 846 may also be constructed to control the removal of the anvil 402 from the target vessel. Alternately, the anvil 402 is removed from the target vessel by sliding the head 712 relative to the target vessel. Where two or more cam paths 846 are used, a cam follower extends from the distal anastomotic tool 41 into each cam path 846. Where a single cam path 846 is used, the distal anastomotic tool 41 is biased toward the cam path 846 by a spring or other mechanism, to ensure that the cam follower remains within the cam path 846 throughout the travel of the distal anastomotic tool. The anvil 402 may be inserted into the target vessel before or after the graft vessel/clamp assembly 43 is placed on the distal anastomotic tool 41.

Figure 81:
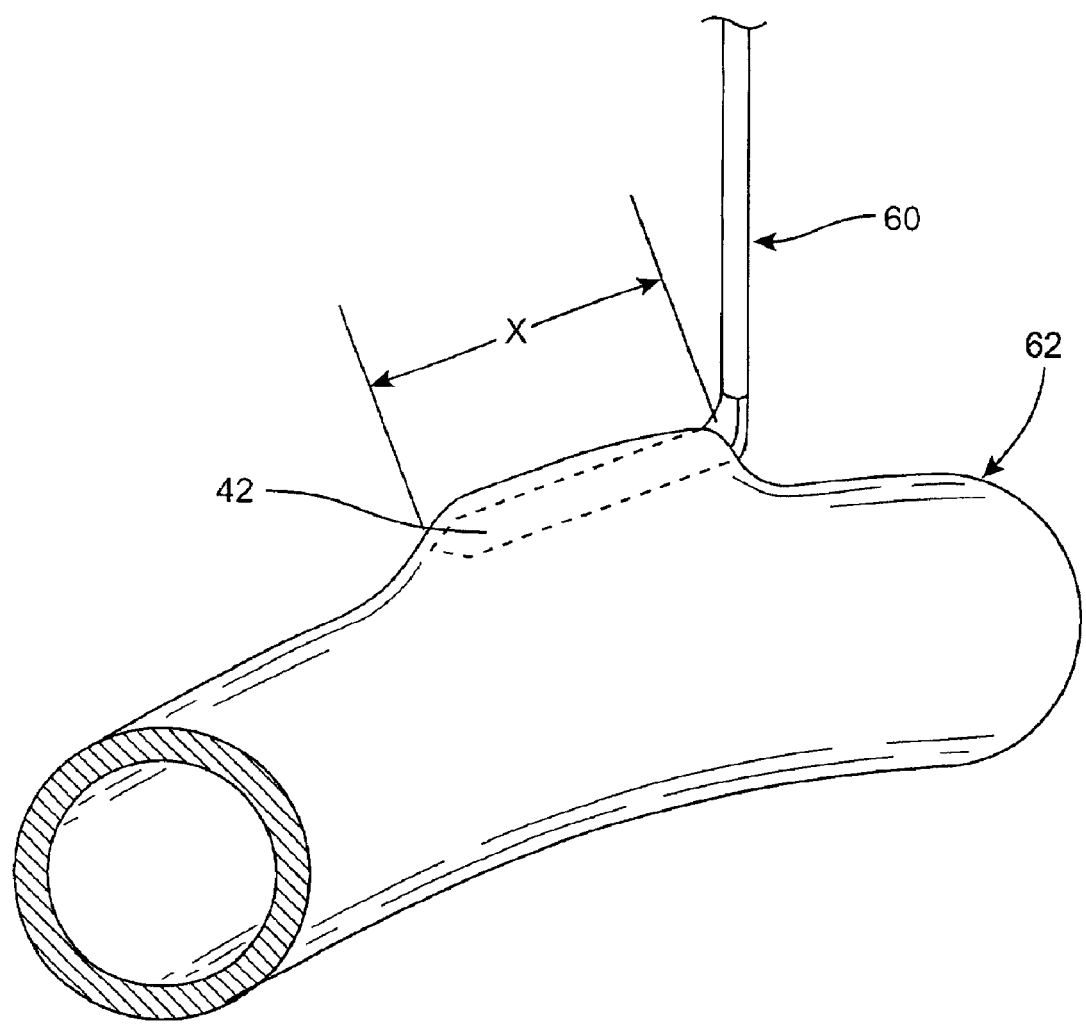
FIG. 81 is a perspective view of the target vessel showing the stabilization of target vessel after an anvil is inserted into the target vessel.

FIG. 81 shows the target vessel tensioned by the anvil 42. The other parts of the anastomosis tool are not shown for purposes of clarity. The anvil 42 establishes a critical dimension X along the target vessel 53 which corresponds to the length of the anvil 42 along which the graft vessel 30 will be stapled. Referring also to FIG. 13, the critical dimension Y of the graft vessel defined during preparation of the graft vessel is substantially equal to the critical dimension X formed by the anvil 42 on the target vessel. The length of the incision made in the target vessel 53 can also be substantially the same as the critical dimension X as defined by the anvil.

One or more cables (not shown) may be connected to the first actuator 50 and/or second actuator 56. The cable or cables extend from the distal anastomotic tool 704 to the linkage 706 or other shaft of the tool 710. The cable or cables may extend through the passage 724 within each link 718, or may extend along the tool 710 outside of the linkage 706. The cable or cables may terminate at the handle 708 of the tool 710, or at a separate device or location. Thus, the cable or cables extend out of the thoracic cavity through one of the trocar ports 64,66. In this way, the surgeon may use the cable or cables to actuate the actuators 50, 56. The cable or cables also may be used to move the distal anastomotic tool along the cam path in the head (not shown). In another embodiment, one or more cables replace the first actuator 50 and/or the second actuator 56. In such an embodiment, the anvil 402 is connected directly to a cable rather than to the first actuator 50, and/or the movable arms 54 are connected directly to a cable rather than to a second actuator 56. Thus, the surgeon can manipulate the movable arms 54 and the anvil 402 at the appropriate times by applying tension to the cables.

Figure 82:
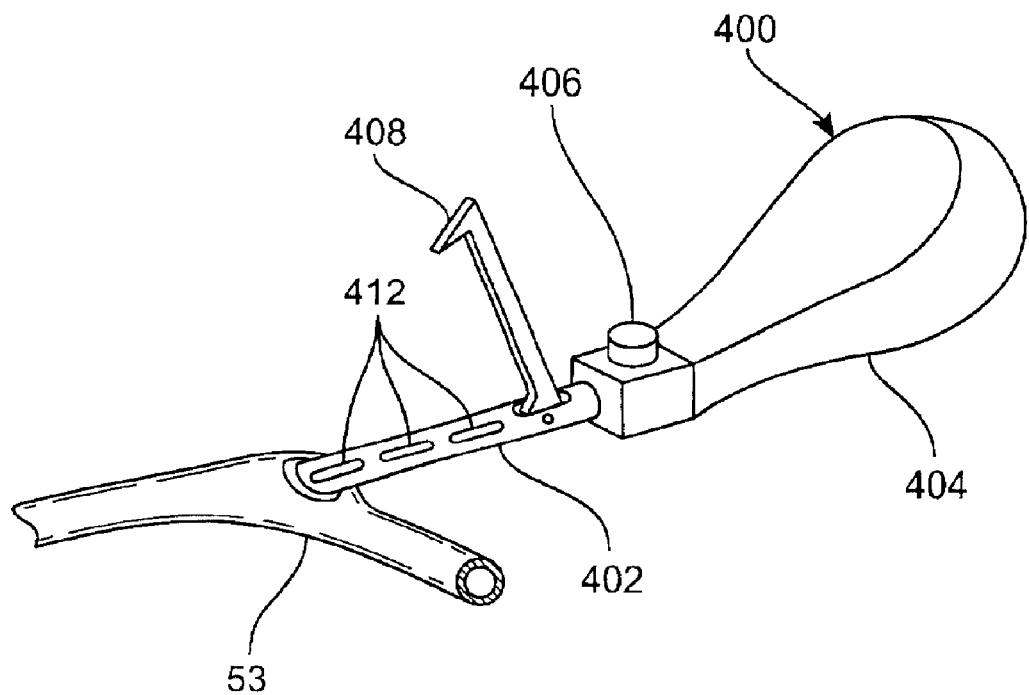
FIG. 82 is a perspective view of an anvil with a removable handle being inserted into a target vessel.

Another embodiment of a distal anastomotic tool 41 having a modular configuration is depicted in FIGS. 82-86. As shown in FIG. 82, the tool 400 comprises an anvil 402 having a removable handle 404. In FIG. 82, the anvil 402 is shown being inserted into the target vessel 53. The handle 404 is attached to the anvil 402 using a set screw 406 or other attachment means. A cutter 408 is also shown for forming an opening in the target vessel 53 after the anastomosis has been performed. Staple bending features 412 are also shown.

Figure 83:
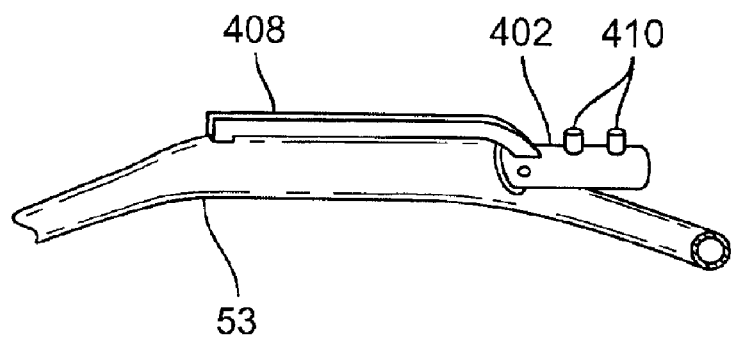
FIG. 83 is a perspective view of the target vessel of FIG. 82 showing the anvil inserted in the target vessel with the handle removed.

FIG. 83 shows the anvil 402 inserted in the target vessel 53 with the handle 404 removed. Removal of the handle 404 leaves an exposed portion of the anvil 402 projecting from the target vessel 53. The exposed portion of the anvil 402 has docking features 410 for mating with a graft vessel clamp (not shown) attached to the distal end of the graft vessel.

Figure 84:
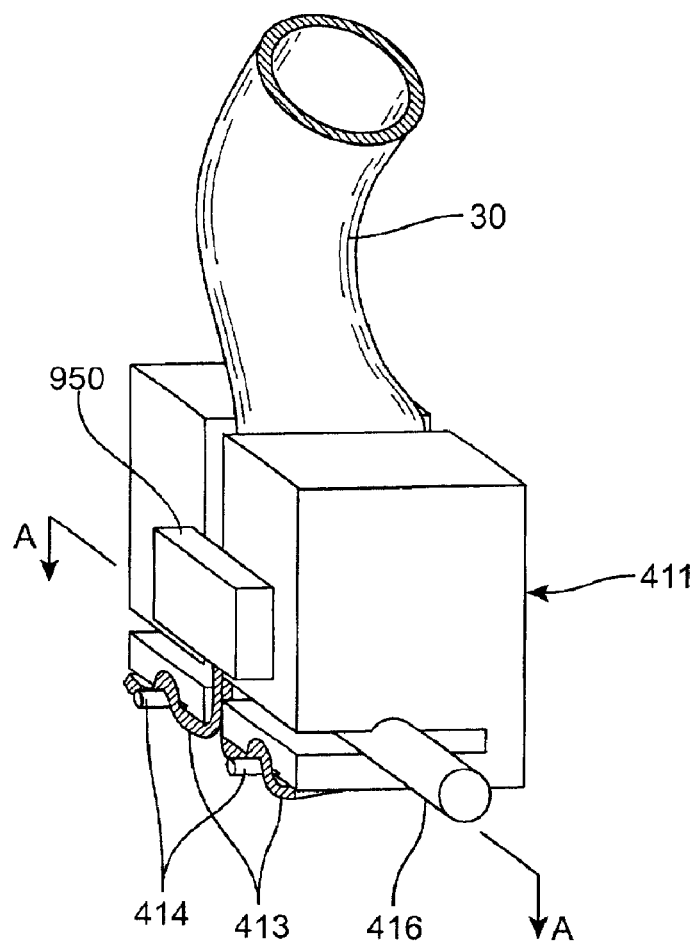
FIG. 84 is a perspective view of a graft vessel/clamp assembly including a staple deploying means for use with the system of FIG. 82.
Figure 85:
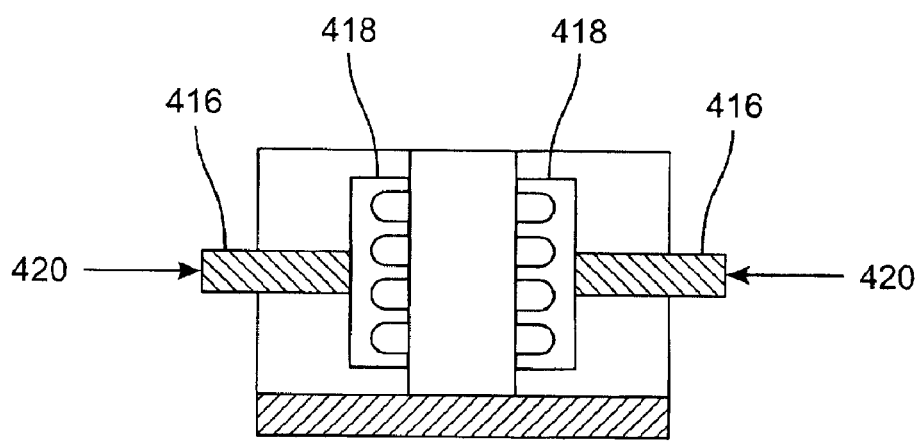
FIG. 85 is a cross-sectional view of the graft vessel/clamp assembly taken along line A–A of FIG. 84.

A graft vessel/clamp assembly suitable for use with the anvil 402 of FIG. 83 is shown in FIGS. 84–85. The graft vessel clamp 411 holds the graft vessel 30 in a configuration such that when the clamp 411 is attached to the anvil 402, the end of the graft vessel 30 is in a correct position over the target vessel 53 for anastomosis. The graft vessel clamp 411 as shown includes first pins 414 to hold graft vessel flaps 413 in place. The graft vessel clamp 411 can also include second pins 416 (one shown) for actuation of a staple or clip deploying device (not shown). A camera 950 may be provided on the clamp 411 to allow for clear viewing of the distal anastomosis process. These features can be seen more clearly in FIG. 85 which is a cross sectional view of the graft vessel/clamp assembly of FIG. 84 taken through the line A—A. FIG. 85 shows the second pins 416 for actuation of the staple or clip deploying device 418. In use, the second pins 416 are moved in the direction indicated by arrows 420 to deploy the staples or clips by a remote actuation device which is shown in FIG. 85.

Figure 86:
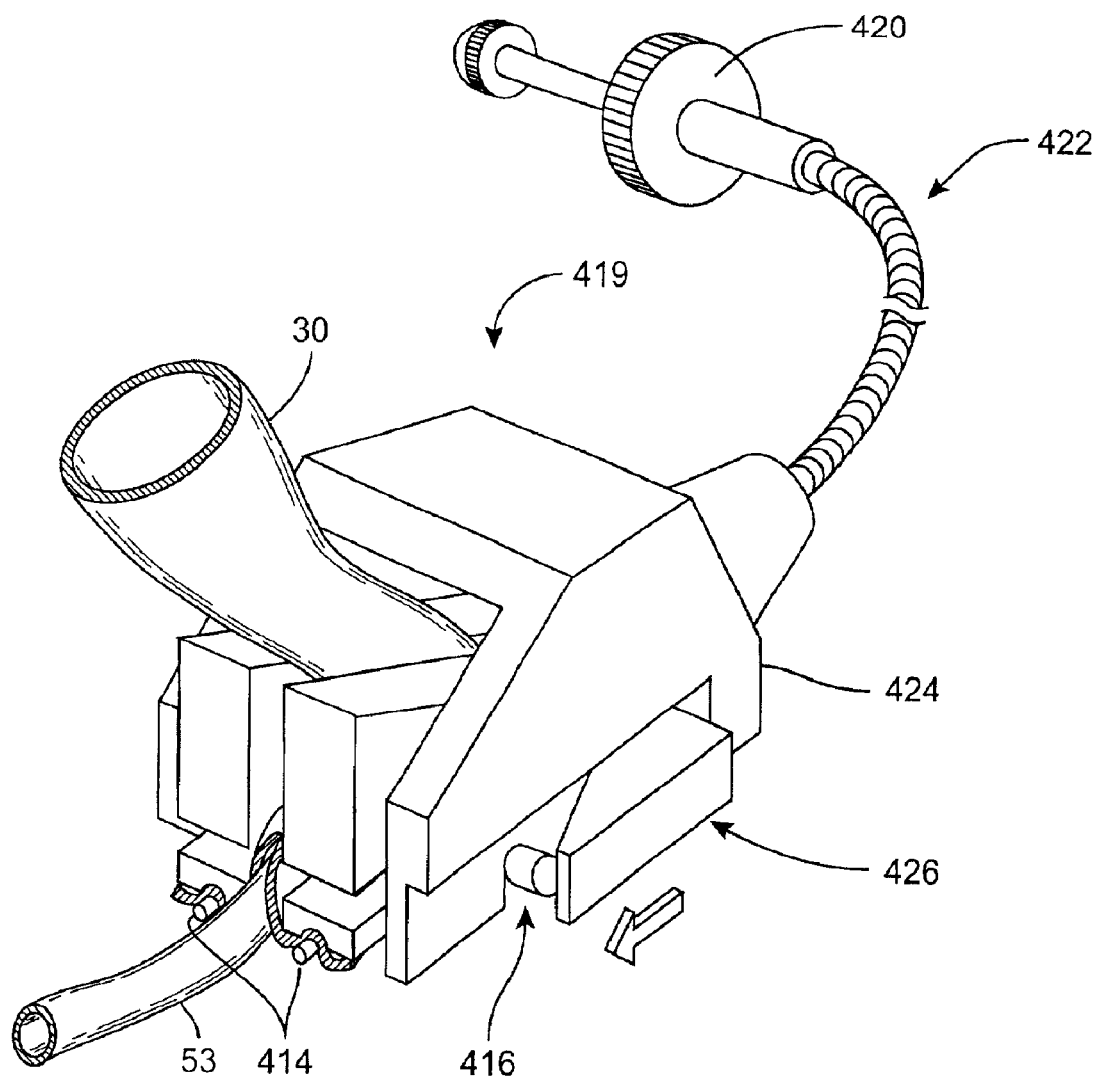
FIG. 86 is a perspective view of a remote actuation device engaged with the graft vessel/clamp assembly of FIG. 84.

FIG. 86 shows a remote actuation device 419 for use with the graft vessel clamp 411 of FIGS. 84–85. The remote actuation device 419 comprises a hand actuator 420, attached by a flexible cable 422 to a housing 424 comprising cams 426. When actuated, the cams 426 move forward to depress the second pins 416 on the graft vessel clamp assembly. When depressed, the second pins 416 drive staples or clips (not shown) into the graft vessel and target vessel tissue to connect the vessels together. When staples are used, the anvil 402 can include staple bending features on its surface.

Although stabilization of the blood receiving vessel is achieved using an anvil in the embodiments set forth above, the blood receiving vessel can also be stabilized for distal anastomosis using an inflatable balloon or by other means known in the art.

Figure 87:
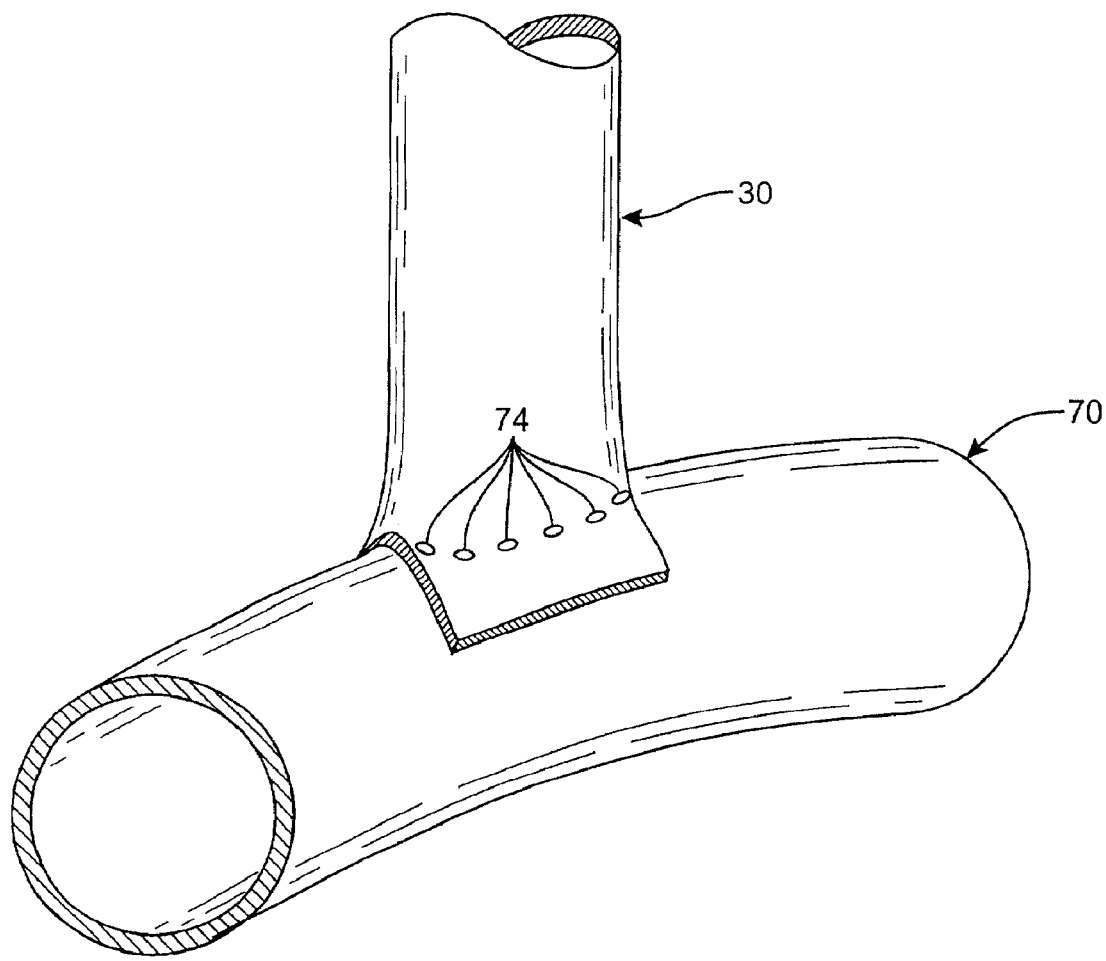
FIG. 87 is a perspective view of a completed anastomosis between a target vessel and a graft vessel performed with a plurality of staples.

FIG. 87 illustrates a completed distal anastomosis between a target vessel 70 (blood receiving artery) and a graft vessel 30 using a plurality of staples 74. A spacing between the staples 74 is preferably approximately 1 to 4 mm, which is similar to the spacing between sutures in a conventional sutured anastomosis. The anastomosis between the graft vessel and the blood receiving artery is compliant. That is, a number of individually-placed discrete elements at the anastomosis are not in contact with one another, and collectively allow the completed anastomosis to expand and contract with the blood flow.

Once the distal anastomosis has been completed and the distal tool removed, the bulldog clamp (if present) can be removed from the graft vessel. Both ends of the grafted vessel can then be checked for leaks. The integrated stabilizer 704 is then released relative to the heart, and removed from the thoracic cavity through a large trocar port 66 in the patient's chest. Additional vein grafts are then made on the left side of the heart, as needed. After placement of all of the vein grafts on the left side of the heart, the tools are removed from the thoracic cavity of the patient via the trocar ports 64, 66. The trocar ports 64,66 themselves are removed from the patient, and the incisions are closed in a standard manner. The left lung is then re-inflated. If vein grafts are to be placed on the right side of the heart, the right lung is deflated. Incisions are made in one or more intercostal spaces on the right side of the chest, and trocar ports 64, 66 are inserted into them. The RIMA may be taken down through these trocar ports 64, 66, if needed. The anastomoses on the right side of the heart are then performed as described above. Alternately, if the sub-xyphoid approach is used, no additional incisions are made; rather, the right lung is deflated and the vein grafts are placed on the right side of the heart via the sub-xyphoid opening. Alternately, if the sub-xyphoid approach is used, additional incisions may be made as needed.

The incision or incisions made in the pericardium may be clipped or sutured closed at the end of the procedure. If multiple incisions are made in the pericardium, and both the left side and the right side of the chest are opened during the procedure, the incisions made on a particular side of the pericardium may be closed before the trocar ports 64, 66 on that side of the chest are removed and the corresponding incisions closed. Alternately, the incision or incisions in the pericardium may be left open at the end of the procedure. If so, the inflated lungs prevent the heart from herniating out of the incision or incisions in the pericardium. After completion, tools are removed from the patient, the trocar ports 64, 66 are removed from the incisions, and the incisions are closed. The right lung is then re-inflated.

While the invention has been described in detail, it will be apparent to one skilled in the art that various changes and modifications can be made and equivalents employed, without departing from the present invention. For example, the method and instrumentation described above can be adapted to perform anastomosis on other blood vessels or tubular structures within a human or animal body. Therefore, the invention is not to be restricted or limited except in accordance with the following claims and their legal equivalents.

What is claimed is:

1. A method for performing beating-heart closed-chest surgery on a patient to connect a graft vessel to at least one target vessel, comprising:
   creating at least one point of entry into the thoracic cavity;
   gaining access to a distal anastomotic site;
   stabilizing the heart by inserting through at least one point of entry an integrated stabilizer connected to a tool; and
   performing a distal anastomosis between an end of the graft vessel and the side of the target vessel with said tool while the heart is beating, said performing comprising stapling the graft vessel to the target vessel and creating an opening in the target vessel.

2. The method of claim 1, further comprising
   performing a proximal anastomosis between the graft vessel and another target vessel while the heart is beating, utilizing a tool inserted through at least one point of entry.

3. The method of claim 2, wherein said performing a proximal anastomosis comprises:
   placing an end of a tool substantially normal to the target vessel, said tool holding the graft vessel; and
   deploying an anastomosis device to attach the graft vessel to the target vessel.

4. The method of claim 3, further comprising splitting said tool to release the graft vessel.

5. The method of claim 2, further comprising measuring the distance between the proximal anastomosis site and the distal anastomotic site with a vein measuring device inserted through at least one point of entry into the thoracic cavity.

6. The method of claim 2, further comprising viewing the anastomosis sites during the procedure.

7. The method of claim 1, wherein said creating comprises utilizing a sub-xyphoid approach.

8. The method of claim 1, wherein said creating comprises utilizing an intercostal approach.

9. The method of claim 1, further comprising deploying a trocar port in at least one point of entry into the thoracic cavity.

10. The method of claim 1, wherein said gaining access comprises creating an opening in the pericardium, wherein the opening extends substantially from the aorta to the apex of the heart.

11. The method of claim 1, wherein said gaining access comprises accessing the intrapericardial space.

12. The method of claim 1, wherein said performing a distal anastomosis further comprises attaching a clamp assembly to the distal end of the graft vessel.

13. The method of claim 12, further comprising slicing the distal end of the graft vessel.

14. The method of claim 12, further comprising connecting said clamp assembly to said tool.

15. The method of claim 1, further comprising performing at least one additional distal anastomosis.

16. The method of claim 1, wherein said distal anastomosis is sutureless.

17. The method of claim 1, wherein said stabilizing includes exerting a force against both the heart and the chest wall, whereby said force restricts motion of the heart.

18. A The method of claim 1, wherein said integrated stabilizer has a substantially oval perimeter configured to contact the heart.

19. The method of claim 1, further comprising a linkage connected to said integrated stabilizer, wherein said linkage extends out of at least one point of entry during said stabilizing and said performing.

20. A method for performing beating-heart closed-chest surgery on a patient to connect a graft vessel to at least one target vessel, comprising:
   creating at least one point of entry into the thoracic cavity;
   gaining access to a distal anastomotic site;
   stabilizing the heart by inserting through at least one point of entry an integrated stabilizer connected to a tool;
   performing a proximal anastomosis between the graft vessel and another target vessel while the heart is beating utilizing a tool inserted through at least one point of entry wherein said proximal anastomosis is sutureless; and
   performing a distal anastomosis between an end of the graft vessel and the side of the target vessel with said tool while the heart is beating.

21. A method for performing beating-heart closed-chest surgery on a patient to connect a graft vessel to at least one target vessel, comprising:
   creating at least one point of entry into the thoracic cavity;
   gaining access to a distal anastomotic site;
   stabilizing the heart by inserting through at least one point of entry an integrated stabilizer connected to a tool, wherein said stabilizing includes securing the integrated stabilizer to the heart by deploying at least one clip from said integrated stabilizer to engage the heart;
   performing a distal anastomosis between an end of the graft vessel and the side of the target vessel with said tool while the heart is beating; and
   removing at least one said clip after said performing.

22. A method for performing beating-heart closed-chest surgery on a patient to connect a graft vessel to at least one target vessel, comprising:
   creating at least one point of entry into the thoracic cavity;
   gaining access to a distal anastomotic site;
   stabilizing the heart by inserting through at least one point of entry an integrated stabilizer having an open space and connected to a tool; and
   performing a distal anastomosis between an end of the graft vessel and the side of the target vessel with said tool while the heart is beating, wherein said tool is positioned substantially within said open space of said integrated stabilizer during said performing wherein said integrated stabilizer comprises a shell having said open space.

23. A method for performing beating-heart closed-chest surgery on a patient to connect a graft vessel to at least one target vessel, comprising:
   creating at least one point of entry into the thoracic cavity;
   gaining access to a distal anastomotic site;
   stabilizing the heart by inserting through at least one point of entry an integrated stabilizer connected to a tool, wherein said integrated stabilizer includes an integrated endoscope; and
   performing a distal anastomosis between an end of the graft vessel and the side of the target vessel with said tool while the heart is beating.

24. A method for performing beating-heart closed-chest surgery on a patient to connect a graft vessel to at least one target vessel, comprising:

creating at least one point of entry into the thoracic cavity;

gaining access to a distal anastomotic site;

stabilizing the heart by inserting through at least one point of entry an integrated stabilizer connected to a tool, wherein said integrated stabilizer includes a shell having an open space therein and an integrated light source; and performing a distal anastomosis between an end of the graft vessel and the side of the target vessel with said tool while the heart is beating wherein said tool is positioned substantially within said open space of said shell during said performing.

25. A method for performing beating-heart closed-chest surgery on a patient to connect a graft vessel to at least one target vessel, comprising:

creating at least one point of entry into the thoracic cavity;

gaining access to a distal anastomotic site;

stabilizing the heart by inserting through at least one point of entry an integrated stabilizer connected to a tool, wherein said tool includes an anvil; and performing a distal anastomosis between an end of the graft vessel and the side of the target vessel with said tool while the heart is beating, wherein said performing comprises inserting said anvil through the wall of and into the lumen of the target vessel.

26. The method of claim 25, further comprising moving said anvil against the wall of the target vessel.

* * * * *